United States Patent
Adie et al.

(10) Patent No.: US 11,505,821 B2
(45) Date of Patent: Nov. 22, 2022

(54) CLOSED LINEAR DNA PRODUCTION

(71) Applicant: Touchlight IP Limited, London (GB)

(72) Inventors: Thomas Adie, London (GB); Neil Porter, London (GB); Paul Rothwell, London (GB)

(73) Assignee: Touchlight IP Limited, London (GB)

( * ) Notice: Subject to any disclaimer, the term of this patent is extended or adjusted under 35 U.S.C. 154(b) by 83 days.

(21) Appl. No.: 16/325,621

(22) PCT Filed: Aug. 16, 2017

(86) PCT No.: PCT/GB2017/052413
§ 371 (c)(1),
(2) Date: Feb. 14, 2019

(87) PCT Pub. No.: WO2018/033730
PCT Pub. Date: Feb. 22, 2018

(65) Prior Publication Data
US 2019/0185924 A1 Jun. 20, 2019

(30) Foreign Application Priority Data

Aug. 16, 2016 (GB) ...................... 1613994
Dec. 22, 2016 (GB) ...................... 1621954

(51) Int. Cl.
*C07H 21/00* (2006.01)
*C12Q 1/6844* (2018.01)

(52) U.S. Cl.
CPC ...... *C12Q 1/6844* (2013.01); *C12Q 2521/113* (2013.01); *C12Q 2525/151* (2013.01);
(Continued)

(58) Field of Classification Search
USPC .................. 435/6.1, 6.11, 91.1; 436/94, 501; 536/23.1, 24.3, 24.33
See application file for complete search history.

(56) References Cited

U.S. PATENT DOCUMENTS

| | | | |
|---|---|---|---|
| 2004/0110282 A1* | 6/2004 | Kanda ..................... | A61P 31/12 435/325 |
| 2013/0203123 A1* | 8/2013 | Nelson ................. | C12Q 1/6848 435/91.52 |
| 2013/0216562 A1* | 8/2013 | Porter ................. | C12Q 1/6846 424/184.1 |

FOREIGN PATENT DOCUMENTS

| | | |
|---|---|---|
| EP | 2 692 870 A1 | 2/2014 |
| WO | WO 2009/120372 A2 | 10/2009 |

(Continued)

OTHER PUBLICATIONS

"TelN protelomerase" from New England Biolab. Printed on Sep. 10, 2021.*

(Continued)

*Primary Examiner* — Frank W Lu
(74) *Attorney, Agent, or Firm* — Bookoff McAndrews, PLLC

(57) ABSTRACT

The present invention relates to improved processes for production of closed linear deoxyribonucleic acid (DNA), in particular cell-free enzymatic production of closed linear DNA molecules, preferably using a closed linear DNA as a template for DNA synthesis. The invention further relates to a novel closed linear DNA species, suitable for use as a template in the improved processes for production of closed linear DNA. Further, the invention pertains to the intermediate products of the processes, since this enables the production of larger quantities of closed linear DNA from the template than with methods known in the art.

3 Claims, 15 Drawing Sheets

Specification includes a Sequence Listing.

(52) U.S. Cl.
    CPC . *C12Q 2525/301* (2013.01); *C12Q 2525/307* (2013.01); *C12Q 2531/119* (2013.01); *C12Q 2531/125* (2013.01)

(56) References Cited

FOREIGN PATENT DOCUMENTS

| WO | WO 2010/086626 A1 | 8/2010 |
| WO | WO 2012/017210 A1 | 2/2012 |
| WO | WO 2016/034849 A1 | 3/2016 |

OTHER PUBLICATIONS

Mei, L. et al., "Self-assembled multifunctional DNA nanoflowers for the circumvention of multidrug resistance in targeted anticancer drug delivery," *Nano Research,* vol. 8, pp. 3447-3460 and Supplementary Material (2015).

Lv, Y. et al., "Preparation and biomedical applications of programmable and multifunctional DNA nanoflowers," *Nature Protocols,* vol. 10, pp. 1508-1524 (2015).

Zhu, G. et al., "Noncanonical Self-Assembly of Multifunctional DNA Nanoflowers for Biomedical Applications," *Journal of the American Chemical Society,* vol. 135, pp. 16438-16445 and Supplemental Information (2013).

International Search Report for PCT/GB2017/052413, dated Nov. 7, 2017 (2 pages).

\* cited by examiner

Fig. 4

CLOSED LINEAR DNA PRODUCTION

This application is a U.S. national stage filing under 35 U.S.C. § 371 of International Application No. PCT/GB2017/052413, filed on Aug. 16, 2017, which claims the benefit of priority to GB Application No. 1613994.1, filed on Aug. 16, 2016, and GB Application No. 1621954.5, filed on Dec. 22, 2016.

SEQUENCE LISTING

This application contains a sequence listing, submitted electronically in ASCII format under the filename Sequence_Listing.txt, which is incorporated by reference herein in its entirety. The ASCII copy of the sequence listing was created on Feb. 14, 2019, and is 58,785 bytes in size.

FIELD

The present invention relates to improved processes for production of closed linear deoxyribonucleic acid (DNA), in particular cell-free enzymatic production of closed linear DNA molecules, preferably using a closed linear DNA as a template for DNA synthesis. The invention further relates to a novel closed linear DNA species, suitable for use as a template in the improved processes for production of closed linear DNA. Further, the invention pertains to the intermediate products of the processes, since this enables the production of larger quantities of closed linear DNA from the template than with methods known in the art.

BACKGROUND

The cell-free production of closed linear DNA has previously been described by the applicant in WO2010/086626 and WO2012/017210; which are hereby incorporated by reference. The method described in these applications relates to the production of linear double stranded DNA covalently closed at each end (closed linear DNA) using a DNA template, wherein the DNA template comprises at least one protelomerase recognition sequence, and where the template is amplified using at least one DNA polymerase and processed using a protelomerase enzyme to yield closed linear DNA. The closed ends of the closed linear DNA each include a portion of a protelomerase recognition sequence. The use of a closed linear DNA as a template is envisioned in the listed applications, and the use of such a template is advantageous, since it means that the minimum amount of reagents are wasted during production. Small-scale experimental production of closed linear DNA works well with a closed linear DNA template using these methods. However, the yield is lower than expected, and not sufficient for preparation of commercially viable amounts of closed linear DNA.

When a closed linear DNA template is used in the methods described above, the closed linear DNA molecule may be viewed as a single stranded circular molecule as depicted in FIG. 5. Usually, closed linear DNA as described herein is essentially fully complementary in sequence, although some minor variations or "wobbles" may be tolerated by the structure. Thus, the closed linear DNA may be at least 95% complementary, or at least 96, 97, 98, 99 or 100% complementary in sequence. When denatured, it is effectively a circular molecule comprising both forward (sense or plus) and reverse (antisense or minus) strands adjacent to each other. This is in contrast to plasmid DNA where the complementary sequences (minus and plus) lie on separate circular strands (FIG. 5, A compared to B).

The unique structure of closed linear DNA means that it can renature more readily than a plasmid and therefore oligonucleotide priming for DNA amplification by DNA polymerase can present more of a challenge. This is particularly the case where single primers are used that bind to the palindromic sequences comprising the protelomerase recognition sequence within the hairpin. The closed linear DNA template may be amplified using a strand-displacing polymerase which initially produces concatamers comprising single strands of DNA, each concatamer comprising multiple repeat units of the DNA template, each repeat unit being complementary in sequence to the original sequence of the closed linear DNA template. However, since each template includes both the plus and minus strands, the concatameric single strand DNA produced includes alternate minus and plus strand sequences as a "repeat unit". This can be compared with amplification from a plasmid, where the single strand that is produced from the circular template (either strand) comprises multiple repeats of the same sequence in the opposite orientation (i.e. a sense strand is replicated as a concatamer comprising multiple repeat units of the antisense strand). Thus, there are distinct structural differences in the concatameric product produced as a result of strand displacement replications of a plasmid DNA template and a closed linear DNA template. It is these structural differences in the product of amplification from a closed linear DNA that may result in inefficient generation of closed linear DNA.

Since the concatamers that are initially produced from the amplification of a closed linear DNA are a single strand of DNA, they are theoretically available as a template for further primer binding and thus further replication. This step generates a concatamer with two distinct complementary strands, and then either stand may be displaced to replicate a further new strand. The "double stranded" concatamer thus comprises two distinct complementary strands of DNA. Notionally, large amounts of amplification can take place from a small amount of initial template, due to the nature of the strand-displacement polymerase used. The double stranded DNA concatamer is important, since this is ultimately the substrate for the protelomerase enzyme used in the process of manufacture of closed linear DNA, as described in previous applications, such as WO2010/086626 and WO2012/017210.

However, the inventors have established that when closed linear DNA is used as a template, some or most of the "product" is formed as DNA nanoflowers, despite the addition of a protelomerase enzyme to cleave the complete protelomerase recognition sequences in the double stranded concatamers and form closed linear DNA. This is shown on FIG. 6. The single strand of DNA comprising alternate "plus" and "minus" strands is effectively self-complementary and therefore readily folds internally to compact structures known as DNA nanoflowers. These are essentially long single strands of concatameric DNA which have self-hybridised and are no longer available for priming or processing with protelomerase, since the strands are packed tightly together. This is far from the ideal scenario. Required for standard methods of closed linear DNA production is the production of linear double stranded concatamers using the initial single strand concatameric DNA as a template, and this double stranded intermediate is processable by a protelomerase to form closed linear DNA molecules (step K of FIG. 5). The complete protelomerase recognition sequence is formed from two complementary strands of DNA, in a duplex formation.

The adjacent plus—minus nature of the initial single strand of DNA produced by a strand-displacing polymerase acting on a closed linear DNA template results in extensive internal hybridisation of the concatamers to produce DNA nanoflowers (FIG. 6, step F). This compact, folded DNA structure prevents efficient oligonucleotide primer binding (FIG. 6, step G) necessary to convert the DNA nanoflowers into protelomerase-processable linear double stranded concatamers as used in the methods current in the art.

There is therefore a need for an improved in vitro process to efficiently amplify a closed linear DNA template at high DNA yields or alternatively put, to decrease the production of impenetrable DNA nanoflowers during production of closed linear DNA, and/or to increase the conversion of already formed DNA nanoflowers into closed linear DNA

SUMMARY

The present invention relates to a process for the in vitro, cell free production of closed linear DNA from a closed linear DNA template. The process may allow for enhanced production of closed linear DNA compared to current methodologies. This significantly increases productivity whilst reducing the cost of producing closed linear DNA, particularly on a larger scale.

Accordingly there is provided a cell-free method of producing closed linear DNA molecules comprising:
   (a) contacting a template comprising linear, double stranded DNA molecule covalently closed at each end by a portion of a protelomerase recognition sequence and comprising at least one stem loop motif with a strand-displacing polymerase under conditions promoting amplification of said template in the presence of at least one primer which is capable of binding specifically to a primer binding site within said stem loop motif;
   (b) contacting the DNA produced in (a) with at least one protelomerase under conditions promoting production of closed linear DNA.

Optionally, the template may comprise further protelomerase recognition sequences, in addition to those portions of protelomerase recognition sequence located at the closed ends or caps of the closed linear DNA template. If the template comprises one or more additional or further protelomerase recognition sequences, the additional protelomerase recognition sequences may be positioned at any site in the double stranded section of the template. Preferably, these additional or further protelomerase recognition sequences are distinct to and separate from the at least one stem loop motif. The additional protelomerase recognition sequence(s) may be separated from one or both of the closed ends of the closed linear DNA by the at least one stem loop motif.

Optionally, each of the protelomerase recognition sequences or portions thereof may be the same sequence or different sequences, each independently of the other. Different recognition sequences will be acted upon by different protelomerase enzymes, and therefore the appropriate protelomerase enzymes will be required for the production of closed linear DNA.

According to a second aspect, the present invention relates to a linear, double stranded DNA molecule covalently closed at each end by a portion of a protelomerase recognition sequence, wherein the sequence of said linear, double stranded DNA molecule includes at least one stem loop motif.

According to a third aspect, the present invention relates to a concatameric DNA molecule comprising a single strand of DNA, said single strand comprising two or more identical units of DNA sequence covalently linked together in a series, each unit comprising at least one portion of a protelomerase recognition sequence and at least one stem loop structure or motif. Optionally, the concatamer is in vitro and cell-free. Optionally, the unit comprises at least one further protelomerase recognition sequence.

According to the third aspect, there may be provided concatameric DNA molecule comprising a single strand of DNA, said single strand comprising two or more identical units of DNA sequence covalently linked together in a series, each unit comprising at least one stem loop structure or motif flanked on either side by at least one portion of a protelomerase recognition sequence. Optionally, said portions are recognised by the same or different protelomerase enzymes.

According to the third aspect, the stem loop structure may comprise all or part of the sequence for a stem loop motif as hereinbefore described.

Further according to the third aspect, the units of DNA sequence are the sequence for a linear, double stranded DNA molecule as defined herein.

The single strand of concatameric DNA as described may form intra-strand base pairs, with the exception of the loop of the stem loop structure. Thus, the single strand of concatameric DNA may form a DNA nanoflower with open, single stranded loops. The invention thus extends to the single stranded concatamer as described herein, folded into a nanoflower.

According to a fourth aspect there is provided a kit, optionally suitable for performing the method of any aspect of the invention, said kit comprising:
   (a) a linear, double stranded DNA molecule covalently closed at each end by a portion of a protelomerase recognition sequence, wherein the sequence of said linear, double stranded DNA molecule includes at least one stem loop motif;
   (b) a protelomerase; and optionally;
   (c) a bridging oligonucleotide.

The kit may further comprise a DNA polymerase and optionally a primer. Additionally, the kit may include any one or more of appropriate buffers, nucleotides, pyrophosphatase and/or nucleases.

According to any aspect of the invention the stem loop motif is a sequence, which may comprise two sequences flanking a central section. The stem loop motif is designed to form a stem loop structure under conditions suitable for the formation of secondary structure, such as when the sequence is present in a single strand of DNA, i.e. without a bound complementary but distinct second strand. Distinct strands have their own 3' and 5' termini. Optionally, said conditions are the amplification conditions used in the method of the present invention, and exemplary conditions are described further below.

According to any aspect or embodiments of the invention the central section of the motif is designed to be looped out as a single stranded DNA when the flanking sequences are brought together; either by self-complementary base pairs forming a stem or by use of a bridging oligonucleotide.

According to any aspect or embodiment of the invention, the stem loop motif or stem loop structure may comprise a primer binding site. This primer binding site is within the central section of the motif or structure, and thus within the single stranded section. Optionally, the primer binding site is surrounded by 1 or 2 adjacent single stranded sequences in the central section.

According to any aspect or embodiment of the invention, the stem loop motif or structure may comprise two flanking sequences to the central section, optionally designed to be self-complementary or designed to be complementary to a bridging oligonucleotide.

According to any aspect or embodiment of the invention, the stem loop motif or structure may be adjacent to or near to a portion of the protelomerase recognition sequence, wherein said portion is within the covalently closed end of the linear DNA molecule. Optionally, the sequence for the stem loop motif or structure is separated by up to 100 bases from the end of the portion of the protelomerase recognition sequence forming the closed end of the template molecule. Where additional protelomerase target sequences are present, these may be adjacent to the stem loop motifs or separate to them.

According to any aspect of the invention, there may be included two or more stem loop motifs in the DNA template, and thus two or more stem loop structures in the concatamer as defined previously. Each stem loop motif may be adjacent or near to a closed end of the closed linear DNA molecule.

According to any aspect of the invention, there may be included one or more additional protelomerase recognition sequences within the double stranded section of the template. Said additional protelomerase recognition sequences are distinct to those present at the closed ends of the template, and further are distinct to the one or more stem loop motifs.

Further embodiments are described below and in the claims. Further advantages are described below.

BRIEF DESCRIPTION OF THE DRAWINGS

The present invention will be described further below with reference to exemplary embodiments and the accompanying drawings, in which:

FIG. 4 shows the whole native recognition sequences for a selection of protelomerase enzymes, showing the sequences of both strands of the complementary DNA. Shown are the target sequences A-H as follows: A. the sequence of SEQ ID NO: 15 (*Escherichia coli* N15 TelN protelomerase), B. the sequence of SEQ ID NO: 16 (*Klebsiella* phage Phi K02 protelomerase), C. the sequence of SEQ ID NO: 17 (*Yersinia* phage PY54 protelomerase), D. the sequence of SEQ ID NO: 1 (*Halomonas* phage PhiHAP-1), E. the sequence of SEQ ID NO: 18 (*Vibrio* phage VP882 protelomerase), F. the sequence of SEQ ID NO: 19 (*Borrelia burgdorferi* protelomerase), G. the sequence of SEQ ID NO: 21 (*Vibrio parahaemolyticus* plasmid Vp58.5 protelomerase), and H. the sequence of SEQ ID NO: 20 (*Agrobacterium tumefaciens* TelA protelomerase). Where the minimum sequence length requirement for the cognate protelomerase is known, this has been indicated by shading the sequence grey, although the enzyme may accept some variation in sequence within this core recognition sequence. Nucleotides represented in bold and underlined indicate imperfections in the palindrome sequence. The vertical line through the sequences represents the centre of the perfect inverted sequence and the point at which the protelomerase cleaves and joins its specific recognition sequence;

FIG. 9A is a closed linear DNA molecule with the ends of the molecule formed by a portion of a protelomerase target sequence. FIG. 9B is a closed linear DNA with a stem-loop motif as described in the present application. The stem loops are paired due to the complementary nature of the sequences present on the opposing sections of the DNA. FIG. 9C shows a DNA nanoflower, made from a single strand of DNA that has formed intra-strand base pairs between complementary sequences. FIG. 9D shows the same structure as 9C, with the addition of a stem loop motif to the sequence. This results in pairs of stem loops forming within the DNA nanoflower, permitting primer annealing and initiation of DNA synthesis in the direction shown.

DETAILED DESCRIPTION

The present invention relates to improved, cell-free processes for synthesising or amplifying closed linear DNA from a closed linear DNA template.

The Closed Linear DNA Template

The DNA template for use in the method of the invention has certain features which are pertinent, and these are described further below. Closed linear DNA, i.e. linear double stranded covalently closed DNA molecules; typically comprise a linear double stranded section of DNA with covalently closed ends, i.e. hairpin ends. The hairpins join the ends of the linear double DNA strands, such that if the molecule was completely denatured, a single stranded circular DNA molecule would be produced.

Figures 1, 2:
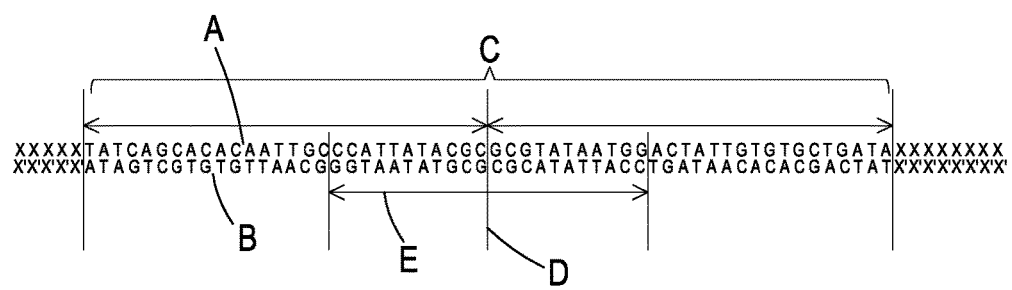
FIG. 1 shows the sequence of the protelomerase recognition sequence for protelomerase TelN in a linear format, without the hairpin structures (SEQ ID NO: 15). It can be seen that the first portion of the protelomerase recognition sequence (A) has a sequence which is complementary to the second portion of the protelomerase recognition sequence (B). At the centre (in this example) of the protelomerase recognition sequence (D) is the site at which the protelomerase will cleave the sequence, which is in the centre of the telO sequence (E). The complete protelomerase recognition sequence (C) is composed of TelRL for the enzyme TelN.
FIG. 2 shows what happens to the sequence of FIG. 1 (SEQ ID NO: 15) once protelomerase TelN catalyses the reaction at the recognition sequence. The sequence is cleaved at the point indicated (D on FIG. 1) and the each cleaved ends are re-ligated with the opposing strand to form two separate hairpin structures.
Figure 3:
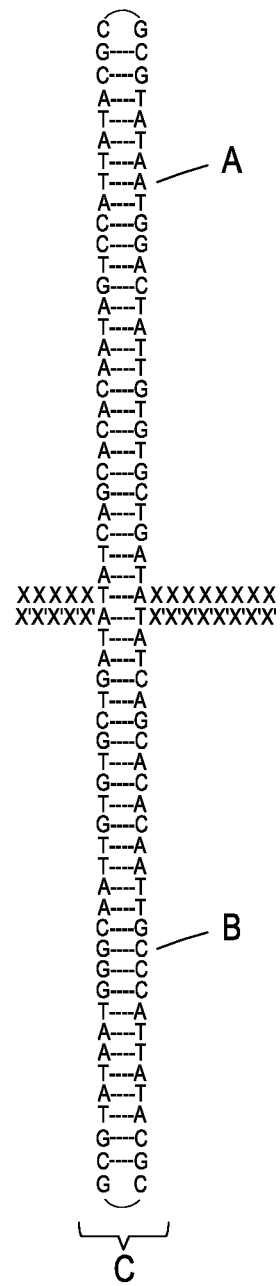
FIG. 3 depicts the same sequence as FIG. 1 (SEQ ID NO: 15), but demonstrates that the portions of the protelomerase recognition sequence (A and B) may form internal hairpins, rather than bind to the other portion of the protelomerase recognition sequence, despite being complete (C)
Figure 5:
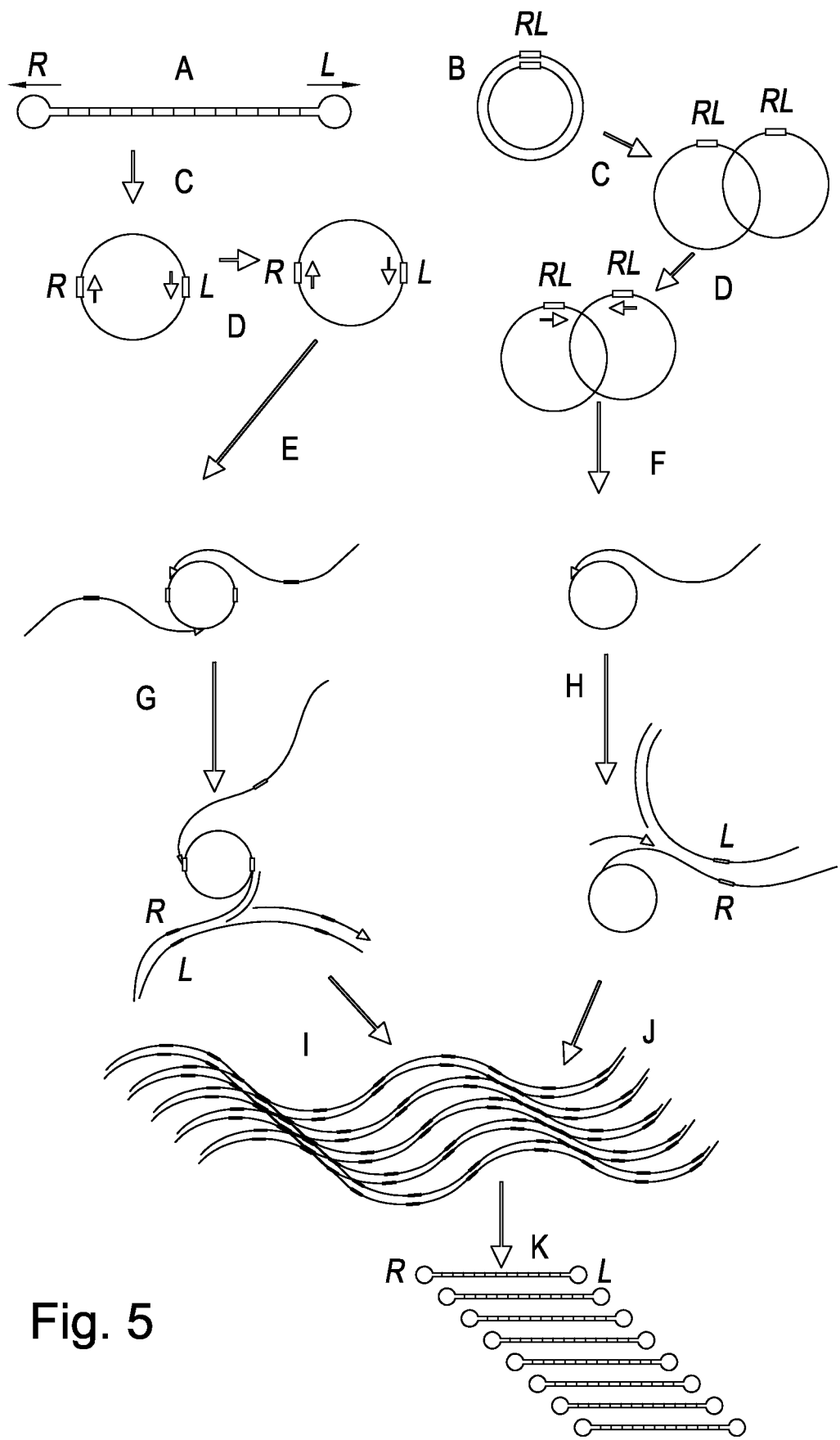
FIG. 5 shows the ideal specific process for in vitro manufacture of closed linear DNA using a single specific palindromic primer, a closed linear DNA template and a strand displacement DNA polymerase in combination with TelN protelomerase. A. Closed linear DNA template. R and L represent the DNA sequences of the right and left arms of the TelN protelomerase recognition sequence. B. Plasmid DNA template. C. Denaturation of starting template to form circular single stranded DNA. Since the plasmid DNA template is comprised of catenated rings of single stranded DNA, it will be understood that the single stranded circles cannot be separated. These 'catenanes' or topologically interlinked circles are not covalently linked, but cannot be separated because they are interwound and each is covalently closed. D. Binding of single specific primer. E-H. Amplification from single stranded DNA template by a strand displacement DNA polymerase. I-i. Formation of long concatameric double stranded DNA comprising single units of amplified template separated by protelomerase binding sequences (RL). K. Contacting with TelN protelomerase specific to RL sequence. Protelomerase cleaves concatameric DNA at RL site and ligates complementary strands to produce amplified copies of the linear covalently closed DNA template.
Figure 6:
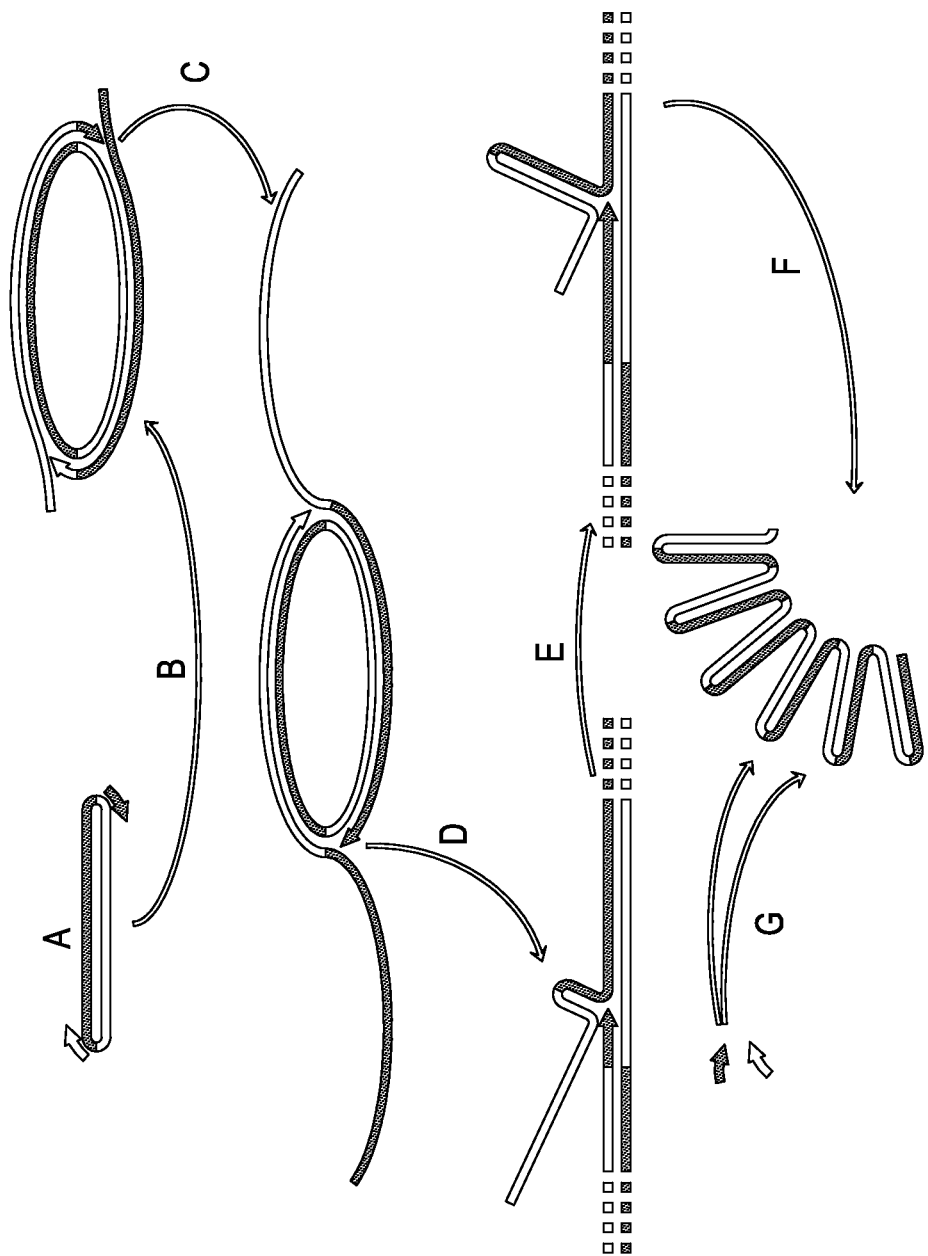
FIG. 6 shows the same process as FIG. 5, only instead of forming long concatameric double stranded DNA, the concatameric single strand of DNA folds into DNA nanoflowers; A. Closed linear DNA template; B-C. Specific primer binding and amplification from single stranded DNA template by a strand displacement DNA polymerase and formation of long concatameric single strands of DNA, although two primer species are shown in this embodiment they are identical, but the method could be performed with two or more different primer species. D-E. Specific primer binding to the concatameric single strand of DNA and replication of the same, leading to hairpin formations at the portions of the protelomerase recognition sequences. F-G. the formation of DNA nanoflowers made from concatameric single strand of DNA, to which primers are unable to bind.
Figure 7:
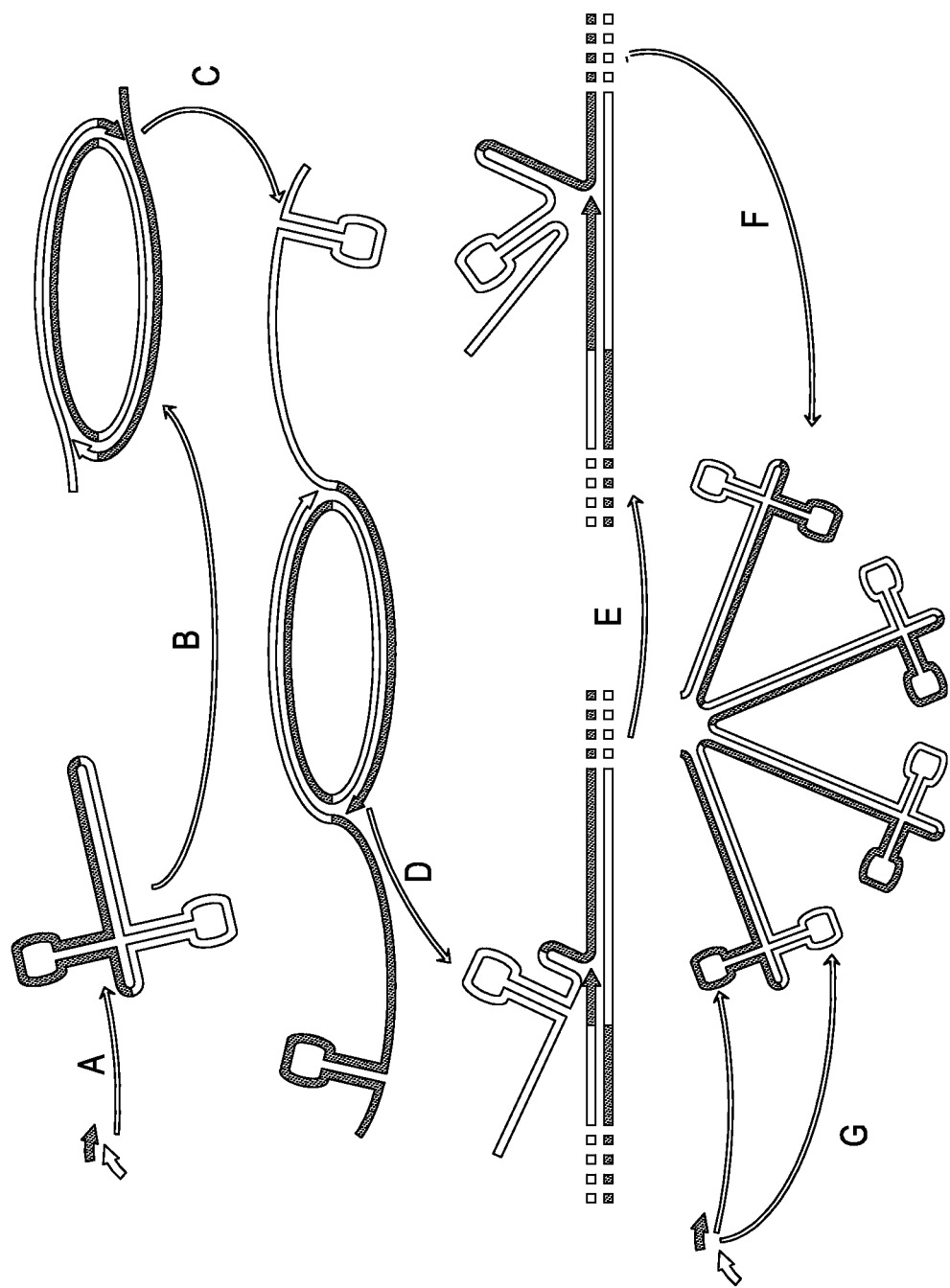
FIG. 7 shows the same general process as FIGS. 5 and 6, with the exception that the closed linear DNA template includes a stem loop motif according to the present invention. This stem loop motif includes a primer binding site, and is particularly designed so that the stem loop structure is formed when the sequence for the motif is single stranded; thus forming in the concatameric single strands of DNA. This allows the nanoflowers to have an "open loop" structure, in which a primer binding site is located. This enables the primer to anneal and the strand displacement polymerase to force open and convert the nanoflowers into linear double stranded concatameric DNA for processing into closed linear DNA. A depicts the introduction of primers to the template, B depicts the primers binding and amplification occurring, C shows the growth of the single stranded concatameric DNA, D and E show the replication of a single stranded concatamer of DNA, F shows the formation of DNA nanoflowers, except the stem loop motifs force the formation of single stranded regions in the nanoflower, enabling further primer binding (G). It should be noted that the embodiment shown involves the use of two primer species, but this method can equally be performed with one specific primer.
Figure 8:
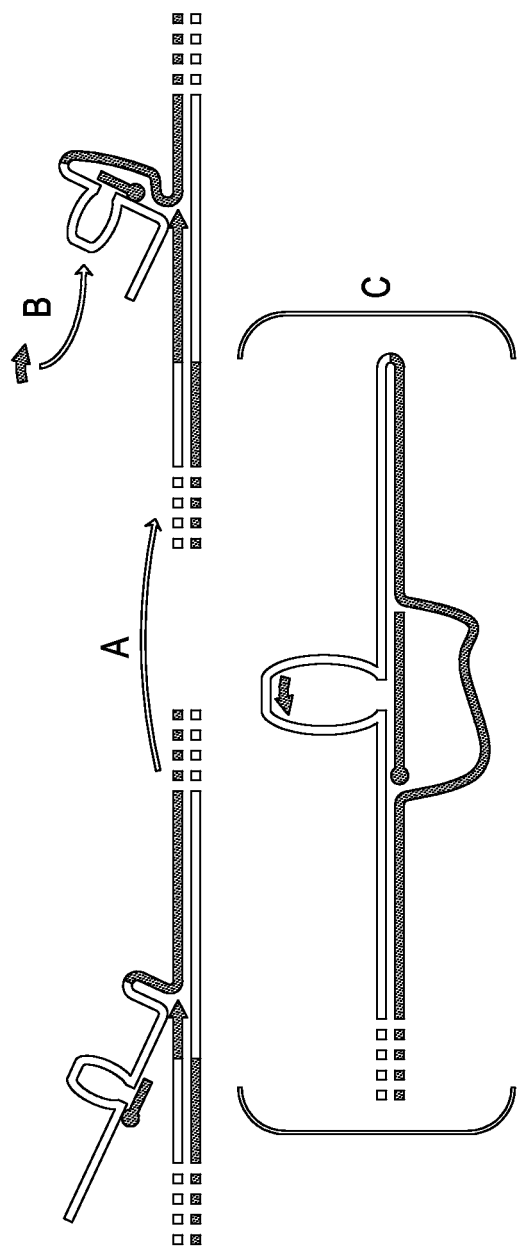
FIG. 8 depicts the use of a bridging oligonucleotide to hold the stem loop motif into an open loop structure. This is an alternative arrangement for the stem loop motif. The bridging oligonucleotide specifically binds to the flanking sequences of the stem loop motif, and forces out the central section into a loop of single stranded DNA. When such a structure is introduced during the process of the invention, it enables the central section of the stem loop motif to be single stranded, thus presenting the primer binding site for the primer to specifically anneal. A. The process of using a bridging oligonucleotide to create a loop within the stem loop motif. B. The binding of a primer to the primer binding site within the loop structure. C. The priming of the loop of the stem loop motif using a bridging oligonucleotide.

For the purposes of this invention, the covalently closed ends or hairpins contain internally complementary sequences, since they comprise a part or a portion of a protelomerase recognition sequence. The bases within the apex (end or turn) of the hairpin may not be able to form base pairs, due to the conformational stress put onto the DNA strand at this point. FIG. 3 shows that it is thought that at least the 2 base pairs at the apex of the portion of the protelomerase recognition sequence may not form basepairs, but the exact conformation is not yet known and likely to be subject to fluctuations depending on the conditions in which the DNA is maintained, and the exact sequences around the hairpin. Thus, 2 or more bases may not be able to form pairs given the structural distortion involved, despite their complementary nature. FIG. 2 showing the hairpins created by the action of the protelomerase TelN on the TelRL site. Some "wobbles" of non-complementary bases within the length of a hairpin may not affect the structure. A wobble may be a break in the palindrome, but the sequences may remain complementary. It is, however, preferred that the sequence of the hairpin is entirely self-complementary. Each protelomerase enzyme, working on its appropriate protelomerase recognition sequence, will generate two different hairpins at the end of the closed linear DNA if there are 'wobbles' in the palindrome. FIG. 2 illustrates this point with both an "R" and an "L" hairpin being generated.

Complementarity describes how the bases of each polynucleotide in a sequence (5' to 3') are in a hydrogen-bonded pair with a complementary base, A to T (or U) and C to G on the anti-parallel (3' to 5') strand, which may be the same strand (internal complementary sequences) or on a different strand. This definition applies to any aspect or embodiment of the invention. It is preferred that the sequences in the hairpin are 90% complementary, preferably 91%, 92%, 93%, 94%, 95%, 96%, 98%, 99% or 100% complementary.

Thus, the DNA template comprises a linear double stranded DNA closed at each end with a portion of a protelomerase recognition sequence. Each end may be formed of a portion of a protelomerase recognition sequence for the same or different protelomerase enzymes. These portions may be named as the first and second protelomerase recognition sequences, and these form the ends of the closed linear DNA template.

The DNA template may comprise further protelomerase recognition sequences, in addition to those at the closed ends (the first and second protelomerase recognition sequences). These further protelomerase recognition sequences are positioned in the double stranded section of the closed linear DNA. There may be one, two or more protelomerase recognition sequences present within the double stranded section. These sequences may be named the third, fourth, fifth, sixth, or "nth" protelomerase recognition sequences. Each may be a protelomerase recognition sequence for the same or different enzyme. It is preferred that the additional or further protelomerase recognition sequences are different to those used to cap the end of the closed linear DNA template (the first and second protelomerase recognition sequences which are independently the same or different—shown as both the same and labelled "A" in FIG. 12).

The additional protelomerase recognition sequences may be positioned at any point in the double stranded DNA segment of the closed linear DNA template. The additional protelomerase recognition sequences are distinct to the stem loop motif, they are not the same entity, since protelomerase recognition sequences cannot fold to form a stem loop as defined herein. It is preferred that, if additional protelomerase recognition sequences are present, that they are separated from the closed ends of the template by a stem loop motif. In this embodiment, it is preferred that there are two additional protelomerase recognition sequences, which are the same or different, and which are separated from the closed ends of the template DNA by a stem loop motif.

Figure 12:
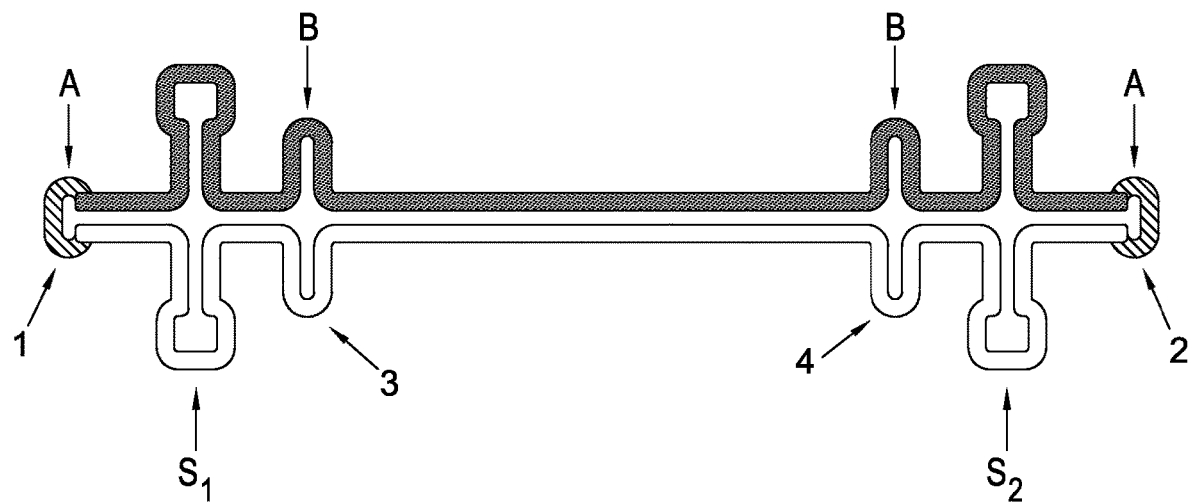
FIG. 12 depicts an exemplary structure of a closed linear DNA template comprising recognition sequences from two different protelomerases separated by a stem loop motif (S1 indicates the complementary stem loop pair that is created at one position due to the stem loop motif, and S2 indicates a second stem loop pair created at a different position due to a further stem loop motif that can be the same or different) incorporating a primer binding sequence. The primer can be designed to bind to either one of the pair. The closed ends of the linear DNA are formed by two portions of the same protelomerase recognition sequence, in this example, protelomerase A. An additional pair of protelomerase B recognition sequences is present within the double stranded section as a complete site capable of being cleaved and ligated by protelomerase B. It will be understood that sequences 1, 2, 3, and 4 could be protelomerase recognition sequences for the same or a mixture of different protelomerase enzymes.

Thus, an exemplary template comprises a linear, double stranded DNA molecule covalently closed at each end by a portion of a first and a second protelomerase recognition sequence; and comprising at least two stem loop motifs and at least a third and a fourth protelomerase recognition sequence, wherein the first of said stem loop motifs is between the first and third protelomerase recognition sequences and the second of said stem loop motifs is between the fourth and second protelomerase recognition sequences. In other words, each stem loop motif is positioned between the capped end of the closed linear DNA and the additional protelomerase recognition sequence. This is depicted in FIG. 12.

A protelomerase recognition sequence is any DNA sequence whose presence in a DNA sequence allows for its conversion into a closed linear DNA by the enzymatic activity of protelomerase. In other words, the protelomerase recognition sequence is required for the cleavage and re-ligation of double stranded DNA by protelomerase to form covalently closed linear DNA. Typically, a protelomerase recognition sequence comprises a palindromic sequence i.e. a double-stranded DNA sequence having two-fold rotational symmetry, also described herein as an inverted repeat. The length of the inverted repeat differs depending on the specific organism from which the protelomerase is derived. The palindrome or inverted repeat may be perfect or imperfect. A complete protelomerase recognition sequence preferably comprises a double stranded palindromic (inverted repeat) sequence of at least 14 base pairs in length.

In more detail, a complete protelomerase recognition sequence is recognised and cleaved by its cognate protelomerase, and can be presented as a duplex of a first DNA sequence comprising a forward (or sense) portion of a protelomerase recognition sequence and a complementary second DNA sequence containing the reverse (or antisense) portion of the protelomerase recognition sequence. Once the recognition sequence has been cleaved, what is left behind is a portion or part of the protelomerase recognition sequence. The portion or part is preferably a single strand of the entire sequence, which when paired with its complementary sequence, forms a complete recognition sequence in a double stranded format. Thus, the portion may be the forward (or sense) portion of the protelomerase recognition sequence or the reverse (or antisense) portion.

Figure 4:
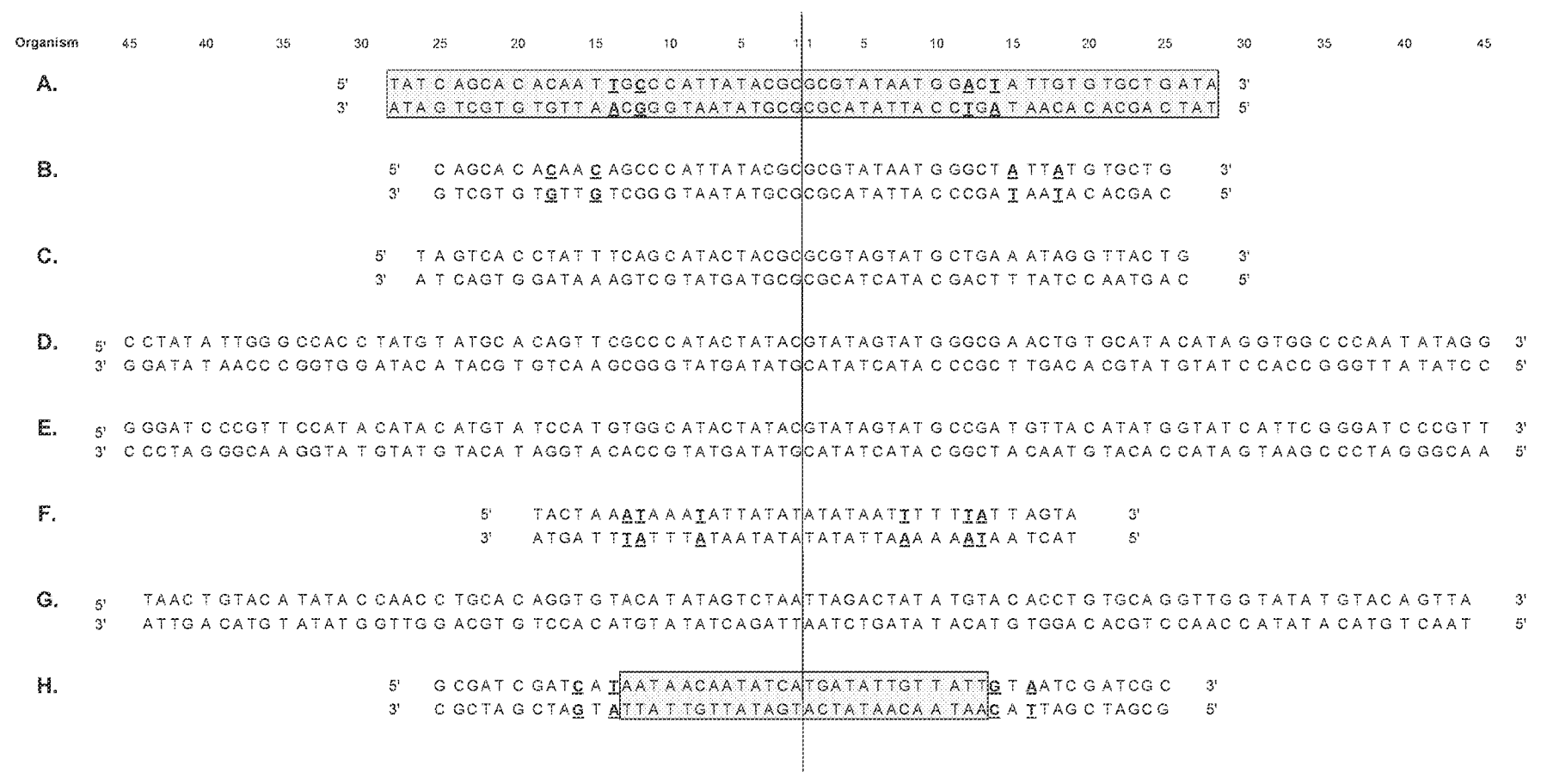

The length of the first or second portion of the protelomerase recognition sequence is determined by the minimum sequence recognised by the cognate protelomerase in order to bind, cleave and re-join the free ends. Several complete protelomerase recognition sequences are depicted in FIG. 4, and each strand represents a portion of the recognition sequence for the cognate protelomerase. The length of the portion of the protelomerase recognition sequence for a cognate protelomerase may be the same or nearly so, since they are capable of annealing to form a duplex. Each portion of a protelomerase recognition sequence may be 20 to 100 bases in length, more particularly 30 to 100 bases in length.

As shown in FIG. 1, despite the two portions (A and B) of the protelomerase recognition sequence (C) forming a duplex due to the complementary nature of the sequence of the portions, because of the palindromic nature of the protelomerase recognition sequence, each portion has the ability to fold into a hairpin due to internal self-complementary sequences within the portion of the recognition sequence. This is shown in FIG. 3.

The closed linear DNA template according to the present invention comprises a sequence for a stem loop motif within the linear double stranded DNA. As used herein, a stem loop motif is a sequence that allows for the formation of a stem loop structure, under the appropriate conditions. The sequence of the stem loop motif may comprise a central section flanked by two additional sequences.

The sequence for the stem loop motif may include a central section which forms the loop structure of the stem loop. This central section (loop) is thus designed to be single-stranded and not be complementary to any of the other bases within the motif. This central section may be any appropriate number of residues in length, but it is preferred that the central section (and hence the loop) is 5 to 50 residues, particularly 5 to 40 residues, more particularly 5 to 30 residues, even more particularly 10 to 25 residues in length. The central section, and thus the loop, may be 5, 6, 7, 8, 9, 10, 11, 12, 13, 14, 15, 16, 17, 18, 19, 20, 21, 22, 23, 24, 25, 26, 27, 28, 29 or 30 residues (bases) in length.

Preferably, the central section of the motif or loop includes a sequence for a primer binding site. A primer binding site is a region of a nucleotide sequence where a primer binds or anneals to start replication. The primer specifically anneals to the primer binding site due to the complementary nature of their sequences. The primer binding site may be designed such that primers can anneal which are complementary to a part or portion of the primer binding site, see for example FIG. 10A Alternatively, the primer binding site and primer may be the same length. Primer design, and thus the sequence of the primer binding site are discussed in more detail further below. The primer binding site is at least 5 residues in length, but can be 5 to 50 residues (bases) in length. Ideally, the primer binding site is 5 to 30 or 5 to 20 residues in length, optionally 5 to 16 residues in length. The primer binding site may be at least 5, 6, 7, 8, 9, 10, 11, 12, 13, 14, 15, 16, 17, 18, 19, 20, 21, 22, 23, 24, 25, 26, 27, 28, 29 or 30 residues in length. It is preferred that the primer binding site forms a part or portion of the central section, adjoined by at least one sequence which separates the primer binding site from the flanking sequences. The adjoining sequence may be present on the 3' or 5' side of the primer binding site, or be present on both sides of the primer binding site. The adjoining sequences may be of any suitable length, and each of the adjoining sequences is independent—i.e. the presence, length or nature of the adjoining sequence may be different on either side of the primer binding site, if present. Each adjoining sequence may be up to 50 residues in length, preferably up to 40, up to 30 or up to 20, most preferably, 15 residues in length. The adjoining sequences may therefore be at least 1, 2, 3, 4, 5, 6, 7, 8, 9, 10, 11, 12, 131, 14, 15, 16, 17, 18, 19 or 20 residues (bases) in length.

Figure 13:
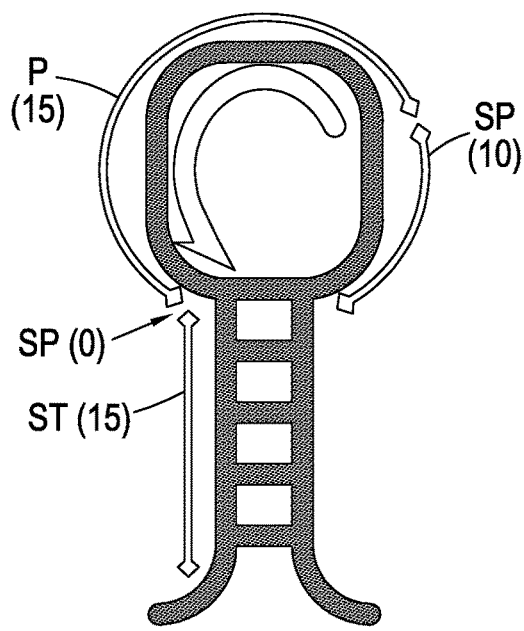
FIG. 13 shows the structure of an exemplary stem loop motif 15-0-15-10, with the priming site held in the open configuration. The naming scheme refers to the length of the stem (ST) (15), the length of the first spacer (SP) (0), the length of the priming site (P) (15), the length of the second spacer (SP) (10). The primer may bind to the top strand. A loop labelled 'reverse' is the same sequence on the opposite strand, with the primer binding to the bottom strand. The scheme could use any suitable length of sequence for any of the elements depicted.

FIG. 13 depicts an exemplary stem loop structure with the format 15-0-15-10, with the priming site held in the open configuration. The naming scheme refers to the length of the stem (15), the length of the first spacer (0), the length of the priming site (15), the length of the second spacer (10). It will be understood that this format could be followed using elements of different lengths to those depicted.

In one embodiment, a stem loop structure may occur due to intramolecular base pairing within a single strand of DNA. In this instance, the stem loop occurs when two regions of the same strand, usually complementary in nucleotide sequence when read in opposite directions, base-pair to form a double stranded section that ends in an unpaired loop. Alternatively, in a second embodiment, the stem loop motif may include sequences which are acted upon by oligonucleotide bridging molecules, which force a section of DNA into a single stranded loop.

The sequence for the stem loop motif may include two complementary regions flanking the central non-complementary loop section. Complementarity is defined previously. Thus, for example, a sequence for a stem loop motif reads (5' to 3'): 5' flanking sequence, central section, 3' flanking sequence. The 5' and 3' flanking sequences are complementary when the 3' flanking sequence is read 3' to 5'. This enables the flanking sequences to base pair to each other and form a duplex, with the central section looping out as a single strand between them. In this embodiment, the flanking sequences are of the same or very similar length. The flanking sequences are preferably at least 5 residues (bases) in length, or at least 6, 7, 8, 9 or 10 residues in length. The flanking sequences may be up to 10, 15, 20, 25, 30, 35, 40, 45 or 50 residues in length. Where the flanking sequences are designed to be self-complementary, it will be appreciated that the stability of double stranded section is determined by its length, the number of mismatches it contains (a small number are tolerable) and the base composition of the paired region. Pairings between guanine and cytosine have three hydrogen bonds and are more stable compared to adenine-thymine pairings, which have only two. Those skilled in the art will appreciate how to design a sequence for a stem loop motif such that the structure, when formed, is stable. The Integrated DNA Technologies Oligoanalyzer may be used in order to determine the suitability of stem loop structures. Version 3.1 is available at https://www.idtdna.com/calc/analyzer.

In an alternative embodiment, the sequences flanking the central section are designed such that they are at least partially complementary to a bridging oligonucleotide. Complementarity is as defined previously. In this embodiment, the flanking sequences are designed to be brought together as an essentially contiguous sequence bound to a bridging oligonucleotide, forcing the central section to loop out between the flanking sequences. Thus, in this embodiment, the flanking sequences are designed to be complementary in sequence to a bridging oligonucleotide. The flanking sequences are preferably at least 5 residues (bases) in length, or at least 6, 7, 8, 9 or 10 residues in length. The flanking sequences may be up to 10, 15, 20, 25, 30, 35, 40, 45 or 50 residues in length. Thus the sequence for a stem loop motif may enable the formation of a stem loop in that sequence, and/or the complementary sequence thereof, under appropriate conditions. Such conditions can include the presence of the sequence for the stem loop motif within a single strand of DNA, such as the single strand that is produced during replication of the template. Alternative conditions in which the stem loop may form is denaturation/renaturation conditions mediated by changes in pH, temperature and ionic environments. It is preferred that the conditions for the formation of the stem loop are those used for the amplification of the DNA template, such that the stem loop structures are formed immediately or shortly after they are incorporated into the synthesised single strand of DNA by the DNA polymerase.

It will be understood by those skilled in the art that the sequence for the stem loop motif, when present in the template, will be present on both the forward (sense) and reverse (antisense) strands (as mirror images/complementary sequences). In a closed linear DNA template the forward and reverse strands are formed of one circular strand of DNA.

When the template is replicated in the method of the invention, the sense sequence replicates to provide an antisense sequence, and the antisense sequence replicated to provide the sense sequence. Thus, there is always a sense and antisense version of the sequence for the stem loop motif in both the template and the replicated DNA. The replicated DNA is a single stranded concatamer, which will comprise both the sense and antisense sequence on the same strand of DNA.

Figure 9:
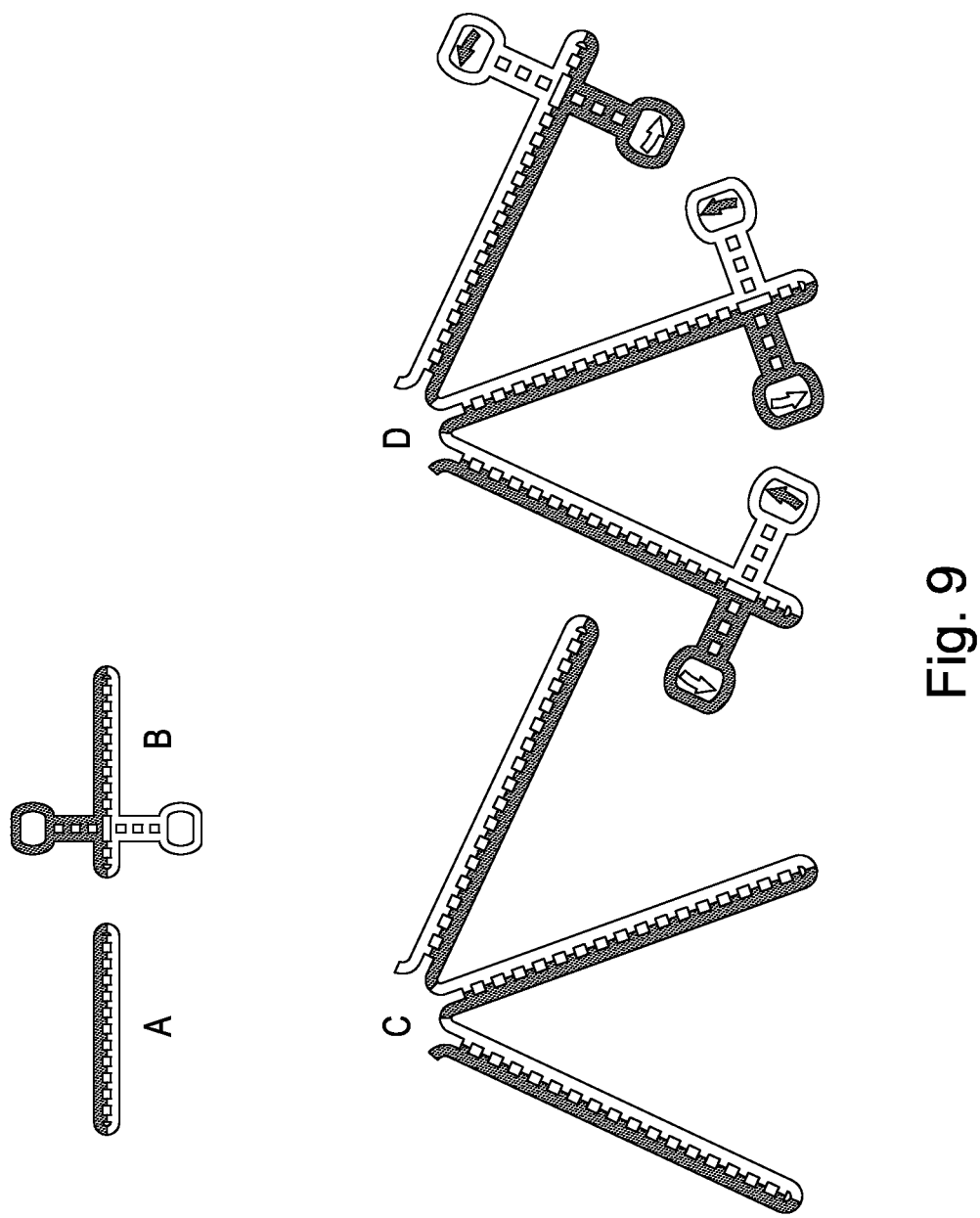
FIG. 9 (A to D) depict various structures discussed in this application depicted schematically.

Both the sense and antisense sequences may be capable of forming a stem loop structure. In the closed linear DNA template, this can result in a paired stem loop structure as shown in FIG. 9B, each of the pair being on opposite sides of the double stranded section of the closed linear DNA. In the replicated DNA, the single stranded concatamer, paired stem loops structures may also form as shown in FIG. 9D. These paired stem loops serve to maintain an open priming site within the DNA nanoflower that forms due to the nature of the DNA sequence being replicated.

A primer may be designed to bind to either the sense or antisense version of the "primer binding site". The method of the present invention requires at least one primer. Optionally, the sequence of the primer binding site is in the correct format (direction) in the sense version/sequence of the stem loop motif. Thus, one option is that the primer anneals to the primer binding site on the sense version of the sequence from the stem loop motif. Clearly, the system can be designed in reverse and the primer may be designed to be able to bind to the primer binding site on the antisense version of the sequence from the stem loop motif. Since both are present in both the template and the replicated DNA, either sequence is available for annealing. Thus, when the method of the invention is performed with sole species of primer it can be designed to anneal to either the sense or antisense version of the primer binding site. If the method of the invention is performed with two or more primers, each primer can be individually designed to bind to either the sense or the antisense version of the sequence for the stem loop motif.

The stem loop motif sequence includes a sequence to form a single stranded loop. As such, it should be noted that the stem loop motif is not a portion of a protelomerase recognition sequence, since this includes no sequence for a loop. Thus, the stem loop motif is distinct from said protelomerase recognition sequence or a portion thereof, and therefore distinct from the closed or capped ends of the closed linear DNA.

The closed linear DNA may comprise one or more sequences comprising a stem loop motif, thus may comprise 2, 3, 4, 5, 6, 7, 8, 9, or 10 such motifs. The stem loop motif may be included at any appropriate location in the closed linear DNA section. Optionally, the stem loop motif sequence is included adjacent to the portion of a protelomerase recognition sequence which forms a covalently closed end. Adjacent in this context can be within 1-100 residues of the end of the portion of the protelomerase recognition sequence, optionally within 1, 2, 3, 4, 5, 6, 7, 8, 9, 10 11, 12, 13, 14, 15, 16, 17, 18, 19 or 20 residues of the end of the protelomerase recognition sequence portion. Alternatively, the two entities may be near to each other, i.e. up to 25, 30, 35, 40, 45, 50, 55, 60, 65, 70, 75, 80, 85, 90, 95 or up to 100 residues apart (can be measured from the end of the protelomerase recognition sequence portion to the start of the stem loop motif, or vice versa).

The closed linear DNA template may further comprise any sequence within the double stranded sequence, either naturally derived or artificial. It may comprise at least one processing enzyme target sequence, such as one, two, three, four or more processing enzyme target sites. Such a target sequence is to allow for the DNA to be optionally processed further following synthesis. A processing enzyme is an enzyme that recognises its target site and processes the DNA. The processing enzyme target sequence may be a target sequence for a restriction enzyme. A restriction enzyme, i.e. a restriction endonuclease, binds to a target sequence and cleaves at a specific point. The processing enzyme target sequence may be a target for a recombinase. A recombinase directionally catalyses a DNA exchange reactions between short (30-40 nucleotides) target site sequences that are specific to each recombinase. Examples of recombinases include the Cre recombinase (with loxP as a target sequence) and FLP recombinase (with short flippase recognition target (FRT) sites). The processing enzyme target sequence may be a target for a site-specific integrase, such as the phiC31 integrase.

The processing enzyme target sequence may be a target sequence for a RNA polymerase, such that the DNA becomes a template for polypeptide synthesis. In this instance, the processing enzyme targeting site is a promoter, preferably a eukaryotic promoter.

The closed linear DNA template may comprise one or more further protelomerase recognition sequences, in addition to those present at the closed ends of the template. These sequences may be any protelomerase recognition sequences, but are preferably different to the first and second protelomerase recognition sequences used in the closed linear ends of the template. They may also be the same or different to each other. It is preferred that at least two additional protelomerase recognition sequences are present, and are included within the double stranded section of the closed linear DNA in a pair. This pair of protelomerase recognition sequences (the third and fourth sequences) may flank a desired sequence in the closed linear DNA template. It is preferred that this desired sequence does not include a stem loop motif as defined herein. The desired sequence may include an expression cassette, or any other sequence of interest. The desired sequence may be the sequence for a closed linear DNA to be produced using the methods of the invention. In this instance, the third and fourth protelomerase recognition sequences are necessary for the formation of the closed ends of the closed linear DNA, with the desired sequence forming the double stranded section. The third and fourth sequences may be sited adjacent to or near the stem loop motifs. In one embodiment, a stem loop motif separates a protelomerase recognition sequence from the nearest closed end. In another embodiment, there are a pair of additional protelomerase recognition sequences, and each are separated from a closed end by a stem loop motif.

The closed linear DNA template may comprise an expression cassette comprising, consisting or consisting essentially of a eukaryotic promoter operably linked to a sequence enclosing a protein of interest, and optionally a eukaryotic transcription termination sequence. A "promoter" is a nucleotide sequence which initiates and regulates transcription of a polynucleotide. "Operably linked" refers to an arrangement of elements wherein the components so described are configured so as to perform their usual function. Thus, a given promoter operably linked to a nucleic acid sequence is capable of effecting the expression of that sequence when the proper enzymes are present. The term "operably linked" is intended to encompass any spacing or orientation of the promoter element and the DNA sequence of interest which allows for initiation of transcription of the DNA sequence of interest upon recognition of the promoter element by a transcription complex.

The DNA template may be of any suitable length. Particularly, the DNA template may be up to 100 kilobases, or up to 50 kilobases, or up to 40 kilobases, or up to 30 kilobases. Preferably the DNA template may be 100 bases to 100 kilobases, 200 bases to 40 kilobases, more preferably 200 bases to 30 kilobases, most preferably 1 kilobases to 15 kilobases.

The closed linear DNA template as used in the method of the invention is unique. Thus, according to a third aspect, the invention relates to a double stranded DNA molecule covalently closed at each end by a portion of a protelomerase recognition sequence, wherein the sequence of said linear, double stranded DNA molecule includes at least one stem loop motif. All these elements have been defined above. Under appropriate conditions, the stem loop motif results in the presence of a pair of stem loop structures within the double stranded section of the closed linear DNA, such as the molecule schematically depicted in FIG. 9B. The closed linear DNA template may include additional protelomerase recognition sequences, as defined previously.

The DNA template as defined above may be provided in an amount sufficient for use in the process of the invention by any method known in the art. For example, the template may be produced by PCR, template extension or any synthetic means of making DNA.

Amplification and Processing

According to the present invention, there is provided a method of producing closed linear DNA from a closed linear DNA template. Said template may be defined as previously described herein.

According to a first aspect, the present invention relates to an in vitro, cell-free method of producing closed linear DNA molecules comprising:

(a) contacting a template comprising linear, double stranded DNA molecule covalently closed at each end by a portion of a first and a second protelomerase recognition sequence and comprising at least one stem loop motif with a strand-displacing polymerase under conditions promoting amplification of said template in the presence of at least one primer which is capable of binding specifically to a sequence within said stem loop motif;

(b) contacting the DNA produced in (a) with at least one protelomerase under conditions promoting production of closed linear DNA.

The DNA template may optionally comprise further protelomerase recognition sequences, additional to the first and second sequences. Preferably, these additional protelomerase recognition sequences are distinct to and separate from the at least one stem loop motif. The additional protelomerase recognition sequences may be separated from one or both of the closed ends of the closed linear DNA by the at least one stem loop motif. These may be identified as the third, fourth etc. protelomerase recognition sequences.

Optionally, each of the protelomerase recognition sequences or portions thereof may be the same sequence or different sequences, each independent of the other. Different recognition sequences will be acted upon by different protelomerase enzymes, and therefore the appropriate protelomerase enzymes will be required for the production of closed linear DNA.

The DNA template is contacted with at least one strand-displacing polymerase. One, two, three, four or five different strand-displacing polymerases may be used. The strand-displacing type polymerase may be any suitable polymerase, such that it synthesises polymers of DNA.

A polymerase may be highly stable, such that its activity is not substantially reduced by prolonged incubation under process conditions. Therefore, the enzyme preferably has a long half-life under a range of process conditions including but not limited to temperature and pH. It is also preferred that a polymerase has one or more characteristics suitable for a manufacturing process. The polymerase preferably has high fidelity, for example through having proofreading activity. Furthermore, it is preferred that a polymerase displays high processivity, high strand-displacement activity and a low Km for dNTPs and DNA. It is preferred that a polymerase does not display DNA exonuclease activity that is not related to its proofreading activity.

The skilled person can determine whether or not a given polymerase displays characteristics as defined above by comparison with the properties displayed by commercially available polymerases, e.g. Phi29 (New England Biolabs, Inc., Ipswich, Mass., US), Deep Vent® (New England Biolabs, Inc.) and *Bacillus stearothermophilus* (Bst) DNA polymerase I (New England Biolabs, Inc.). Where a high processivity is referred to, this typically denotes the average number of nucleotides added by a polymerase enzyme per association/dissociation with the template, i.e. the length of primer extension obtained from a single association event.

Preferred strand displacement-type polymerases are Phi 29, Deep Vent and Bst DNA polymerase I or variants of any thereof. "Strand displacement" describes the ability of a polymerase to displace complementary strands on encountering a region of double stranded DNA during synthesis. The template is thus amplified by displacing complementary strands and synthesizing a new complementary strand. Thus, during strand displacement replication, a newly replicated strand will be displaced to make way for the polymerase to replicate a further complementary strand. The amplification reaction initiates when a primer or the 3' free end of a single stranded template anneals to a complementary sequence on a template (both are priming events). When DNA synthesis proceeds and if it encounters a further primer or other strand annealed to the template, the polymerase displaces this and continues its strand elongation. The strand displacement generates newly synthesised single strands of DNA which can act as a template for more priming events. The priming of the newly synthesised DNA leads to hyper-branching, and a high yield of products. It should be understood that strand displacement amplification methods differ from PCR-based methods in that cycles of denaturation are not essential for efficient DNA amplification, as double-stranded DNA is not an obstacle to continued synthesis of new DNA strands. Strand displacement amplification may only require one initial round of heating, to denature the initial template if it is double stranded, to allow the primer to anneal to the primer binding site if used. Following this, the amplification may be described as isothermal, since no further heating or cooling is required. In contrast, PCR methods require cycles of denaturation (i.e. elevating temperature to 94 degrees centigrade or above) during the amplification process to melt double-stranded DNA and provide new single stranded templates. During strand displacement, the polymerase will displace strands of already synthesised DNA. Further, it will use newly synthesised DNA as a template, ensuring rapid amplification of DNA.

A strand displacement polymerase used in the process of the invention preferably has a processivity of at least 20 kb, more preferably, at least 30 kb, at least 50 kb, or at least 70 kb or greater. In one embodiment, the strand displacement DNA polymerase has a processivity that is comparable to, or greater than phi29 DNA polymerase.

Strand displacement replication occurs during the process of the invention. During strand displacement replication, the template is amplified by displacing already replicated strands, which have been synthesised by the action of the polymerase, in turn displacing another strand, which can be the original complementary strand of a double stranded template, or a newly synthesised complementary strand, the latter synthesised by the action of a polymerase on an earlier primer annealed to the template. Thus, the amplification of the template may occur by displacement of replicated strands through strand displacement replication of another strand. This process may be described as strand displacement amplification or strand displacement replication.

A preferred strand displacement replication process is rolling circle amplification/replication (RCA). The term RCA describes the ability of RCA-type polymerases to continuously progress around a circular DNA template strand whilst extending a hybridised primer. A closed linear DNA template can be denatured to form a single stranded circular DNA. Amplification from such a circle leads to formation of linear products which are single strands of DNA with multiple repeats of amplified DNA linked in series. Further replication from these strands directly may result in hyperbranching. The sequence of the DNA template (a single unit) is multiply repeated within a linear product. Each of these multiple repeat units are identical, and are linked in a series. The initial product of strand displacement amplification from a closed linear DNA is a concatameric single strand of DNA, which is considered to be in the opposite polarity to the original polarity of the closed linear DNA template. However, since each closed linear template includes both the plus and minus strands side by side, the concatameric single strand of DNA produced via amplification includes alternate minus and plus strand sequences in each individual unit. These linear single strands of DNA produced can serve as the basis for multiple hybridisation, primer extension and strand displacement events, resulting in formation of concatameric double stranded DNA products (2 separate complementary strands), again comprising multiple repeats of the individual units (templates) amplified by the polymerase. There are thus multiple copies of each amplified "single unit" DNA in the concatameric double stranded DNA products. RCA polymerases are particularly preferred for use in the process of the present invention. The products of RCA-type strand displacement replication processes may require processing to release single unit DNAs. This is desirable if single units of DNA are required.

In order to allow for amplification, the DNA template is also contacted with one or more primers. The primers are specific for one or more sequences comprised within the DNA template, notably the primer binding site situated in the central section (or loop) of the stem loop motif. The primers are thus specific, meaning that they have a sequence which is complementary to the primer binding site. Complementarity is as defined previously. A single specific primer may be used in the method of the invention due to the complementary nature of the closed linear DNA template. This means that each template comprises both a forward (sense) and reverse (antisense) sequence for the stem loop motif, ensuring that the DNA product produced will also have a reverse (antisense) and a forward (sense) version of the stem loop motif. As mentioned previously, the correct orientation could be in either the sense or the antisense version of the stem loop motif sequence.

Primers may be unlabelled, or may comprise one or more labels, for example radionuclides or fluorescent dyes. Primers may also comprise chemical modifications, typically such that the primer has improved resistance to hydrolysis. For example the primer may preferably comprise one or more phosphorothioate linkages. The primer may be any suitable oligonucleotide, including a DNA primer, ribonucleic acid (RNA) primer or locked nucleic acid (LNA) primer, or any suitable hybrid thereof. Primer lengths/sequences may typically be selected based on temperature considerations i.e. as being able to bind to the template at the temperature used in the amplification step. Analogously, the primer binding site is designed with these considerations in mind.

Additionally, the primer can be synthesized in situ using a primase enzyme. In this version, a primase enzyme can be supplied to build a primer at the open central section of the stem loop motif. Thus, it is also possible to indirectly supply a primer to the template and polymerase.

The contacting of the DNA template with the polymerase and one or more primers may take place under conditions promoting annealing of primers to the DNA template. The conditions include the presence of single-stranded DNA allowing for hybridisation of the primers. The conditions also include a temperature and buffer allowing for annealing of the primer to the template. Appropriate annealing/hybridisation conditions may be selected depending on the nature of the primer. An example of preferred annealing conditions used in the present invention include a buffer, 30 mM Tris-HCl pH 7.5, 20 mM KCl, 8 mM $MgCl_2$. The annealing may be carried out following denaturation using heat by gradual cooling to the desired reaction temperature. Alternative denaturation events include the use of specific concentrations of ions.

Typically, a primer of the invention binds or specifically binds to only the primer binding site within the closed linear DNA template. Primer lengths may vary from, for example, 12, 15, 18, 20 or 30 residues in length. A primer may be of 6 to 30, 12 to 30, 18 to 30 or 25 to 30 residues in length.

Routine methods of primer design and manufacture may be applied to the production of a primer capable of specifically binding to any included primer binding site. Primer lengths/sequences may typically be selected based on temperature considerations such as being able to bind to the template at the temperature used in the amplification step.

Optimally, a primer of the invention binds efficiently to the DNA template following its denaturation to separate the complementary sequences. Denaturation in standard amplification methods typically involves a high temperature "melting" step. Thus a primer can be defined by its melting temperature, or Tm, which is the temperature at which a double-stranded nucleotide separates into single strands. Alternative methods of denaturation may however be used, and these are as discussed below.

Once the primer has annealed or bound to the primer binding site, it is available to start amplification of the DNA template. The primer annealed to the template is incubated under conditions promoting amplification of said template by displacement of replicated strands through strand displacement replication of another strand. The conditions comprise use of any temperature allowing for amplification of DNA, commonly in the range of 20 to 90 degrees centigrade. A preferred temperature range may be about 20 to about 40 or about 25 to about 35 degrees centigrade.

Typically, an appropriate temperature is selected based on the temperature at which a specific polymerase has optimal activity. This information is commonly available and forms part of the general knowledge of the skilled person. For example, where phi29 DNA polymerase is used, a suitable temperature range would be about 25 to about 35 degrees centigrade, preferably about 30 degrees centigrade. The skilled person would routinely be able to identify a suitable temperature for efficient amplification according to the process of the invention. For example, the process could be carried out at a range of temperatures, and yields of amplified DNA could be monitored to identify an optimal temperature range for a given polymerase. The amplification may be carried out at a constant temperature, and it is preferred that the process is isothermal. Since strand displacement amplification is preferred there is no requirement to alter the temperature to separate DNA strands. Thus, the process may be an isothermal process.

Typically, in order to synthesise DNA, the polymerase requires a supply of nucleotides. A nucleotide is a monomer, or single unit, of nucleic acids, and nucleotides are composed of a nitrogenous base, a five-carbon sugar (ribose or deoxyribose), and at least one phosphate group. Any suitable nucleotide may be used. The nitrogenous base may be adenine (A), guanine (G), thymine (T), cytosine (C), and uracil (U). The nitrogenous base may also be modified bases, such as 5-methylcytosine (m5C), pseudouridine (ψ), dihydrouridine (D), inosine (I), and 7-methylguanosine (m7G).

It is preferred that the five-carbon sugar is a deoxyribose, such that the nucleotide is a deoxynucleotide. The nucleotide may be in the form of deoxynucleoside triphosphate, denoted dNTP. This is a preferred embodiment of the present invention. Suitable dNTPs may include dATP (deoxyadenosine triphosphate), dGTP (deoxyguanosine triphosphate), dTTP (deoxythymidine triphosphate), dUTP (deoxyuridine triphosphate), dCTP (deoxycytidine triphosphate), dITP (deoxyinosine triphosphate), dXTP (deoxyxanthosine triphosphate), and derivatives and modified versions thereof. It is preferred that the dNTPs comprise one or more of dATP, dGTP, dTTP or dCTP, or modified versions or derivatives thereof. It is preferred to use a mixture of dATP, dGTP, dTTP and dCTP or modified version thereof.

Other conditions promoting amplification of the closed linear DNA template comprise the presence of metal ions, suitable buffering agents/pH and other factors which are required for enzyme performance or stability. Suitable conditions include any conditions used to provide for activity of polymerase enzymes known in the art.

For example, the pH of the reaction mixture may be within the range of 3 to 12, preferably 5 to 9 or about 7, such as about 7.9. pH may be maintained in this range by use of one or more buffering agents. Such buffers include, but are not restricted to MES, Bis-Tris, ADA, ACES, PIPES, MOBS, MOPS, MOPSO, Bis-Tris Propane, BES, TES, HEPES, DIPSO, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, CABS, phosphate, citric acid-sodium hydrogen phosphate, citric acid-sodium citrate, sodium acetate-acetic acid, imidazole and sodium carbonate-sodium bicarbonate.

While the application of heat (exposure to 95° C. for several minutes) is used to denature double stranded DNA other approaches may be used which are more suitable for DNA synthesis. Double stranded DNA can be readily denatured by exposure to a high or low pH environment or where cations are absent or present in very low concentrations, such as in deionised water. The polymerase requires the binding of a short oligonucleotide primer sequence to a single stranded region of the DNA template to initiate its replication. The stability of this interaction and therefore the efficiency of DNA amplification may particularly be influenced by the concentration of metal cations and particularly divalent cations such as $Mg^{2+}$ ions which may be seen as an integral part of the process.

The amplification conditions may also comprise metal ions. The reaction mixture may also comprise salts of metals such as, but not limited to, salts of divalent metal ions: magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), or salts of monovalent metal ions, including but not limited to lithium ($Li^+$), sodium ($Na^+$) or potassium ($K^+$). The salts may include chlorides, acetates and sulphates. Other salts that may be included are ammonium salts, in particular ammonium sulphate.

Detergents may also be included in the amplification conditions. Examples of suitable detergents include Triton X-100, Tween 20 and derivatives of either thereof. Stabilising agents may also be included in the reaction mixture. Any suitable stabilising agent may be used, in particular, bovine serum albumin (BSA) and other stabilising proteins. Reaction conditions may also be improved by adding agents that relax DNA and make template denaturation easier. Such agents include, for example, dimethyl sulphoxide (DMSO), formamide, glycerol and betaine. DNA condensing agents may also be included in the reaction mixture. Such agents include, for example, polyethylene glycol or cationic lipid or cationic polymers.

It should be understood that the skilled person is able to modify and optimise amplification and incubation conditions for the process of the invention using these additional components and conditions on the basis of their general knowledge. Likewise the specific concentrations of particular agents may be selected on the basis of previous examples in the art and further optimised on the basis of general knowledge. As an example, the amount of polymerase present in the reaction mixture may be optimised. This may involve making further addition of polymerase enzyme to the reaction mixture during the DNA synthesis. As a further example, the amount of DNA template may be optimised. This may involve making further addition of DNA template to the reaction mixture during DNA synthesis.

As an example, a suitable reaction buffer used in rolling circle amplification-based methods in the art is 50 mM Tris HCl, pH 7.5, 10 mM $MgCl_2$, 20 mM $(NH_4)_2SO_4$, 5% glycerol, 0.2 mM BSA, 1 mM dNTPs. A preferred reaction buffer used in the RCA amplification of the invention is 30 mM Tris-HCl pH 7.4, 30 mM KCl, 7.5 mM $MgCl_2$, 10 mM $(NH_4)_2SO_4$, 4 mM DTT, 2 mM dNTPs. This buffer is particularly suitable for use with Phi29 RCA polymerase.

The amplification conditions may also comprise use of one or more additional proteins. The DNA template may be amplified in the presence of at least one pyrophosphatase, such as Yeast Inorganic pyrophosphatase. Two, three, four, five or more different pyrophosphatases may be used. These enzymes are able to degrade pyrophosphate generated by the polymerase from dNTPs during strand replication. Build-up of pyrophosphate in the reaction can cause inhibition of DNA polymerases and reduce speed and efficiency of DNA amplification. Pyrophosphatases can break down pyrophosphate into non-inhibitory phosphate. An example of a suitable pyrophosphatase for use in the process of the present invention is Saccharomyces cerevisiae pyrophosphatase, available commercially from New England Biolabs, Inc.

Any single-stranded binding protein (SSBP) may be used in the process of the invention, to stabilise single-stranded DNA. SSBPs are essential components of living cells and participate in all processes that involve ssDNA, such as DNA replication, repair and recombination. In these processes, SSBPs bind to transiently formed ssDNA and may help stabilise ssDNA structure. An example of a suitable SSBP for use in the process of the present invention is T4 gene 32 protein, available commercially from New England Biolabs, Inc.

Acting upon the primer bound to the template, the polymerase acts to produce multiple repeated and identical units of said DNA template linked in series, otherwise described as a concatameric single strand of DNA. This concatamer comprises multiple identical repeats of the template linked in series. The strand may extend to 100 kb. This concatamer is a single strand, but it will be appreciated that the concatamer may well form secondary structures via intra-strand base pairing, forming sections of duplexed sequence. Given that the preferred template (closed linear DNA) includes side-by-side complementary sequences, the formation of intra-strand base pairs is likely. These complementary sequences within the same strand may anneal to one another, forming duplexes of sequence. However, the stem loop motif prevents the internal base pairing of the loop or central section. It is under the conditions used for amplification as defined herein that it is preferred that the sequence of the stem loop motif forms the secondary structure permitting looping out of the central section as single stranded DNA, preventing this sequence from base pairing to internal complementary sequences. This concatamer with stem loop structures allows for the further replication of the template, since it allows for the one or more primers to anneal to the initial product of amplification, and enables a complementary strand of DNA to be synthesised. The single strand of concatameric DNA may still form a DNA nanoflower, but retains single stranded sequences within the loops. These loops thus provide a suitable structure or site within which to place a primer binding site, allowing for DNA polymerase to use the single strand of concatameric DNA as a template. It is central to the method of the invention that concatamers which are comprised of two distinct complementary strands of DNA are produced, since this is the final intermediate product before closed linear DNA is produced.

The concatameric single strand of DNA with stem loop structures forms a third aspect of the invention. Thus, the invention also provides a concatameric single strand of DNA comprising two or more identical units of DNA sequence covalently linked together in a series, each unit comprising at least one portion of a protelomerase recognition sequence and at least one stem loop structure.

The concatameric single strand of DNA as described herein may comprise multiple repeat units, each unit being the sequence for a linear double stranded DNA as defined herein. Each unit may thus comprise two portions of a protelomerase recognition sequence (which may be the same or different sequences) and at least one stem loop motif to form a stem loop structure. If additional protelomerase recognition sequences are present in the template, these will also be present in the concatameric single strand of DNA in each unit, as set out in the template. It is preferred that the single stranded concatamer will include a stem loop motif flanked on either side by a portion of a protelomerase recognition sequence. It will be understood that each protelomerase recognition sequence is present as a portion as the concatamer is single stranded. In one embodiment, the stem loop motif is flanked by portions of protelomerase recognition sequences that are different. It will be understood that these flanking sequences may indeed be separated by spacer sequences of any appropriate length.

It is preferred that the stem loop structure formed is within the stem loop motif from the template closed linear DNA, as previously defined. Optionally, the stem loop structure may be formed by the complementary flanking sequences annealing to form a stem structure. The central section then loops out between the ends of the stem as a single stranded DNA. It is preferred that the stem loop structure includes a primer binding site, optionally in the central section. The loop structure is critical, since it maintains a portion of sequence in single stranded format and prevents the primer binding site forming inter-strand base pairs with its complementary sequence within the single strand of concatameric DNA. Thus, the primer binding site within the loop or central section is kept open and free for primer binding.

The stem loop structure predominates as a result of amplification of a stem loop motif containing closed linear DNA template since it is formed before its reverse complementary sequence is synthesized. This can be enhanced by carefully selecting the sequence of the residues in the stem to ensure strong base pairing is present. Those skilled in the art are aware of techniques for ensuring the presence of particular secondary structures in single stranded DNA. The design of such sequences is as discussed previously for the template itself.

The presence of the single stranded loop within the concatameric single strand of DNA, (which strand is produced by the action of the polymerase on the template) allows the one or more primers to anneal to the primer binding site and permits the generation of a complementary DNA strand to the initial strand and thus a DNA concatamer with two distinct complementary strands (double stranded concatameric DNA). Either strand could then be used as a further template or double stranded concatameric DNA could be used as a substrate for the one or more protelomerase enzymes.

It is preferred that the amplification step is performed under conditions which promote the formation of a stem loop structure within the concatameric single strand of DNA. Such conditions may simply be those that are optimised for amplification, since these tend to favour the maintenance of single-stranded structure. Under such conditions, stem loops structures that are derived from the stem loop motif including complementary flanking regions form due to base pairing. Alternatively, these conditions may include the addition of one or more agents that promote the formation of loop structures within the single stranded DNA concatamer. This includes the addition of bridging oligonucleotides. These are short (1 to 100, preferably 1 to 90, 1 to 80, 1 to 70, 1 to 60, 1 to 50, 1 to 40, 1 to 30, 1 to 20 or 1 to 10 residues in length) oligonucleotides that are complementary in sequence to the flanking regions within the sequence of the stem loop motif. Ideally, the bridging oligonucleotide is formed of two parts, the first that is complementary to the first flanking sequence, and the second which is complementary to the second flanking sequence. Optionally, there is no gap between these two parts, but in an alternative embodiment, they are separated by 1-50 residues, or alternatively 1 to 40, 1 to 30, 1 to 20, 1 to 10 or 1 to 5 residues. The bridging oligonucleotide can therefore bring the two flanking sequences of the stem loop motif together or nearly so, forcing the central section out into a single stranded loop. Complementarity is as defined previously.

The bridging oligonucleotide may be any suitable nucleic acid. It is preferred that the bridging oligonucleotide is non-extensible by the DNA polymerase, for example, it includes modified residues which prevent extension. Optionally, the bridging oligonucleotide comprises a type of nucleic acid that anneals more strongly to DNA than DNA itself, for example a locked nucleic acid (LNA) or an RNA.

Those skilled in the art are capable of utilising complementarity between residues to design appropriate nucleotides and oligonucleotides for use in the present invention. Thus, it will be routine to design various primer binding site and primer pairs, using this to design a sequence for a stem loop motif or stem loop structure. Further bridging oligonucleotides and flanking sequences can be appropriately designed. Those skilled in the art will be aware routine textbooks such as Molecular Biology of the Gene, 7th Edition, Watson et al, 2014, hereby incorporated by reference.

In addition to the amplification step, a process of the invention for amplification of closed linear DNA also comprises a processing step for production of closed linear DNA. Amplified DNA is contacted with at least one protelomerase under conditions promoting production of closed linear DNA. This simple processing step based on protelomerase is advantageous over other methods used for production of closed linear DNA molecules. The amplification and processing steps can be carried out simultaneously or concurrently. However, preferably, the amplification and processing steps are carried out sequentially with the processing step being carried out subsequent to the amplification step (i.e. on amplified DNA).

A protelomerase is any polypeptide capable of cleaving and re-joining a template comprising a protelomerase recognition sequence in order to produce a covalently closed linear DNA molecule. Thus, the protelomerase has DNA cleavage and ligation functions. Enzymes having protelomerase-type activity have also been described as telomere resolvases (for example in *Borrelia burgdorferi*). A typical substrate for protelomerase is circular double stranded DNA. If this DNA contains a complete protelomerase recognition sequence, the enzyme can cut the DNA at this sequence and ligate the ends to create a linear double stranded covalently closed DNA molecule. The requirements for protelomerase recognition sequences are discussed above. As also outlined above, the ability of a given polypeptide to catalyse the production of closed linear DNA from a template comprising a protelomerase recognition sequence can be determined using any suitable assay described in the art.

Figure 14:
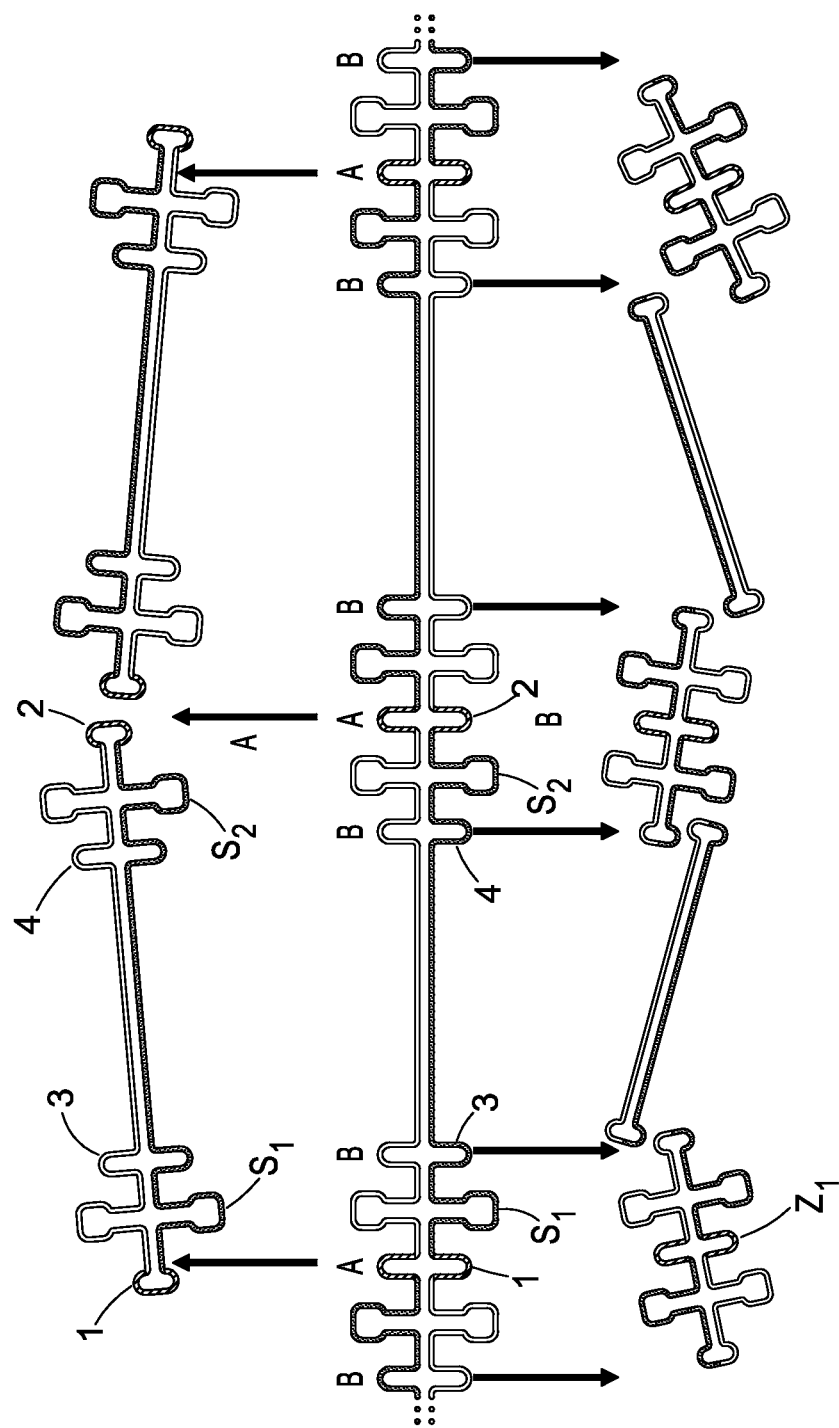
FIG. 14 depicts a process according to one aspect of the present invention when the template of FIG. 12 is used. The central molecule of the figure shows a section of double stranded concatameric product produced by rolling circle amplification of template depicted in FIG. 12. In this instance, the single strand that rolls off the template depicted in FIG. 12 has been converted into a double stranded concatamer through synthesis of a complementary strand, which has been enabled due to the use of the stem loop motifs. This figure depicts the stem loop motifs as complementary stem sequences supporting open single stranded sections that are available for primer binding and further amplification by a strand displacing DNA polymerase. In this instance, protelomerase recognition sequences 1 and 2 are both sequences for Protelomerase A, and protelomerase recognition sequences 3 and 4 are both sequences for Protelomerase B. Both protelomerase recognition sequences A and B are capable of being cleaved and ligated by their respective protelomerases. Cleavage with protelomerase A (top of figure) yields a closed linear DNA identical to the template as depicted in FIG. 12. Cleavage and ligation with protelomerase B (bottom of figure) yields a closed linear DNA capped by protelomerase B recognition sequences and free from protelomerase A recognition sequences and stem loop motifs. Additionally a very short waste closed linear DNA (Z1) is produced also capped by protelomerase B recognition sequences and incorporating the stem loop motifs and a single protelomerase A recognition sequence. Therefore, the skilled person can select which product is produced by varying the protelomerase added to the process. S1 indicates the complementary stem loop pair that is created at one position due to the stem loop motif, and S2 indicates a second stem loop pair created at a different position due to a further stem loop motif that can be the same or different.
Figure 15:
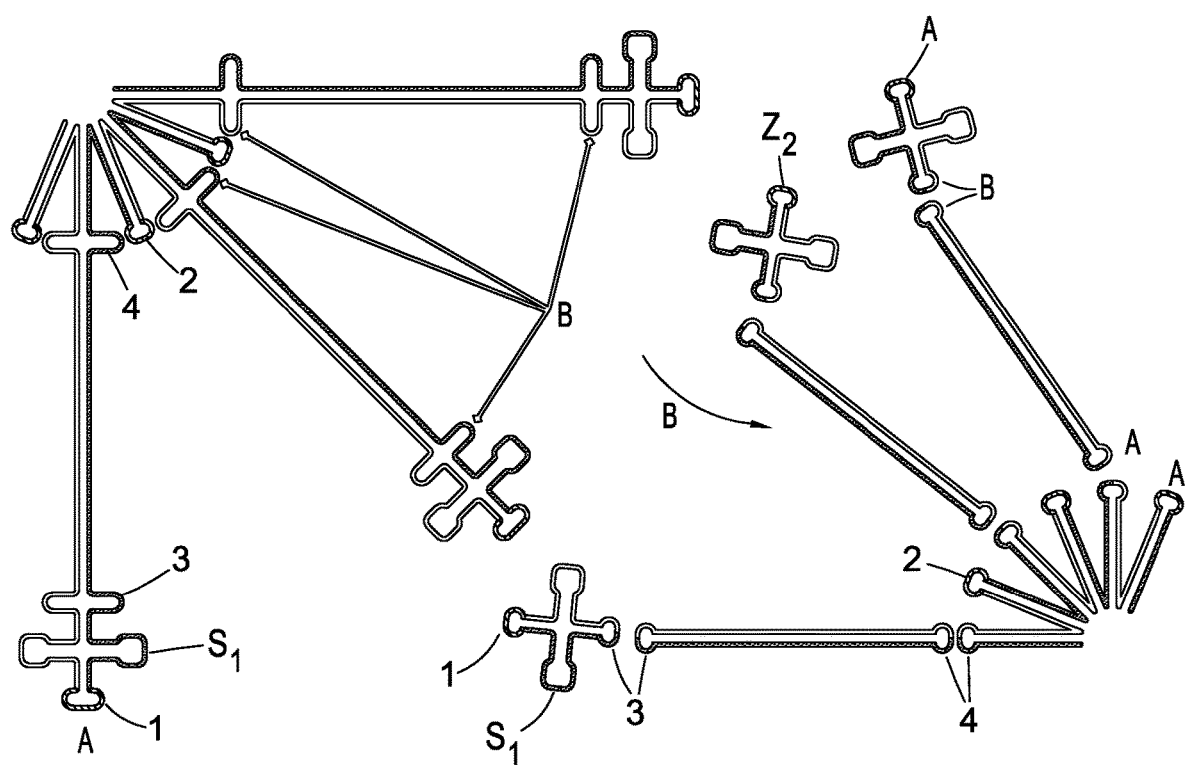
FIG. 15 shows a section of a single stranded concatameric product produced by rolling circle amplification of the closed linear DNA template depicted in FIG. 12. This figure shows how single stranded concatamers are able to fold internally to form nanoflowers if they are not immediately converted into double strands through synthesis of a complementary DNA strand. DNA nanoflowers formed in this way from a closed linear DNA template with additional protelomerase recognition sequences can be directly converted into closed linear DNA including a target sequence by treatment with protelomerase B. Such a closed linear DNA product does not contain any stem loop sequences or protelomerase A recognition sequences (sequences 1 and 2). It should be noted that the second stem-loop structure is not depicted in this figure, since it is thought that these will not form at the nested end, as the inventors assume that adjacent complementary sequences hybridise before separated ones. A small percentage of ends may allow for the formation of stem loops, but the structure depicted is more likely and energetically favourable. This Figure shows one embodiment where a sole primer is used. If an alternative primer is used (i.e. for a different stem loop) then alternative side products (Z2 in this embodiment) may be formed.

The production of closed linear DNA may require the use of at least one protelomerase. The process of the invention may comprise use of more than one protelomerase, such as two different protelomerases, one for each end of the closed linear DNA molecule. If additional protelomerase recognition sequences are used within the DNA template, then more protelomerase enzymes will be required for processing, and the skilled person can make an appropriate selection, depending on the required result. Variations of the process and various potential products are depicted in FIGS. 14 and 15. Processing can take place from double-stranded duplexes or single stranded concatamers folded into nanoflowers.

Examples of suitable protelomerases include those from bacteriophages such as phiHAP-1 from *Halomonas aquamarina* (SEQ ID NO: 1 and 2), PY54 from *Yersinia enterocolytica* (SEQ ID NO: 3 and 4), phiK02 from *Klebsiella oxytoca* (SEQ ID NO: 5 and 6), VP882 from *Vibrio* sp. (SEQ ID NO: 7 and 8), Vp58.5 from *Vibrio parahaemolyticus* (SEQ ID NO: 13 and 14) and N15 from *Escherichia coli* (SEQ ID NO: 9 and 10), or variants of any thereof. Use of bacteriophage N15 protelomerase or a variant thereof is particularly preferred. This enzyme is also referred to as TelN. These enzymes are further described in WO2012/017210, incorporated herein by reference.

The processes of the present invention may be performed with a closed linear DNA template that comprises portions of protelomerase recognition sequence only at the closed ends of the template. In this instance, a cognate protelomerase for each end will be required to convert the double stranded concatameric DNA produced using the methods of the invention into closed linear DNA products. In some instances, the same protelomerase will be sufficient for this task, since each end is a portion of the same protelomerase recognition sequence.

In an alternative embodiment, the process of the invention may be performed with a closed linear DNA template that not only has portions of protelomerase recognition sequences capping the ends of the template (first and second sequences), but also has additional protelomerase recognition sequences. (such as third and fourth sequences). As previously discussed, it is preferred that at least two additional protelomerase recognition sequences are included in the DNA template. These are preferably separated in the closed linear DNA template from the capped ends of the template by at least one stem loop motif. Thus, an exemplary closed linear DNA template may have the sequence (see also FIG. 12):

CAP1-STEM LOOP1-PTS 3-SEQUENCE-PTS4-STEM LOOP2-CAP2

Wherein the CAP1 is a portion of a first protelomerase sequence;

The first and second stem loop motifs are the same or different;

PTS3 and PTS4 are the third and fourth protelomerase recognition sequences which are the same or different;

CAP2 is a portion of a second protelomerase sequence; and

SEQUENCE is the target sequence for inclusion into a closed linear DNA product.

Protelomerase recognition sequences 1 and 2 may be the same or different, but are preferably different to protelomerase recognition sequences 3 and 4.

These sequences may be adjacent to each other, near to each other or separated by intervening sequences.

The single stranded DNA concatamer that results from the amplification of a closed linear DNA template with additional protelomerase recognition sequences may also form DNA nanoflowers. This is depicted in FIG. 15, along with the method to process these nanoflowers.

Thus DNA nanoflowers produced by amplification of a template with additional protelomerase recognition sequences, will also contain these sequences. The present inventors have devised a method that allows the direct release of closed linear DNA products from the single stranded DNA concatamer, which has preferably formed intra-strand base pairs and duplexes, and folded into a nanoflower. This method does not rely upon the formation of a separate complementary strand of DNA to form a DNA duplex prior to processing, and it is therefore not necessary to try to re-prime a folded single strand of DNA. Thus, if additional protelomerase recognition sequences are included in the template, these are replicated in the folded single stranded concatamer, and a whole duplex protelomerase recognition sequence is present as a target for a protelomerase. In this instance, it is possible to contact the amplified DNA with a cognate protelomerase for the additional protelomerase recognition sequences, and liberate a closed linear DNA. The by-products of such a process is a mini closed linear DNA with a stem loop motif contained in the linear DNA section (see FIG. 15).

Such a method to liberate closed linear DNA from the DNA nanoflowers is attractive, because it allows for a "clean-up" of any nanoflowers that are left at the end of the reaction, in case reaction components such as primers, polymerase or nucleotides have been exhausted. It also allows for the production of a closed linear DNA molecule with only the target sequence present, with the removal of the stem loop motif, which may be undesirable for certain indications. Moreover, the additional protelomerase sequences may be used to process double-stranded concatamers as depicted in FIG. 14, this releasing the same product, but with different by-products.

The inventors envisage that the method of the invention may be performed such that closed linear DNA is produced from both double stranded DNA concatamers and single stranded DNA concatamers, both of which have been amplified from a closed linear DNA template, and thus a combination of FIGS. 14 and 15 will operate in practice, depending on the template and enzyme selection. It allows for a selection of the desired product by varying which protelomerase enzyme is added to the amplified DNA, and thus alters which product is obtained. The skilled person will appreciate that a selection can be made simply to add the protelomerase enzyme(s) for the first and second protelomerase recognition sequences that form the caps of the template, and/or to add the protelomerase enzyme(s) for the additional (for example, third and fourth) protelomerase recognition sequences that form part of the duplex section of the closed linear DNA.

The DNA amplified from the DNA template is thus preferably incubated with at least one protelomerase under conditions promoting production of closed linear DNA. In other words, the conditions promote the cleavage and re-ligation of a duplex DNA comprising a protelomerase recognition sequence to form a covalently closed linear DNA with hairpin ends. Conditions promoting production of closed linear DNA comprise use of any temperature allowing for production of closed linear DNA, commonly in the range of 20 to 90 degrees centigrade. The temperature may preferably be in a range of 25 to 40 degrees centigrade, such as about 25 to about 35 degrees centigrade, or about 30 degrees centigrade. Appropriate temperatures for a specific protelomerase may be selected according to the principles outlined above in relation to temperature conditions for DNA polymerases. A suitable temperature for use with *E. coli* bacteriophage TelN protelomerase of SEQ ID NO: 15 is about 25 to about 35 degrees centigrade, such as about 30 degrees centigrade. Conditions promoting the production of closed linear DNA also include the presence of double stranded DNA concatamers, with both portions of the protelomerase recognition sequence forming a complete site upon which the protelomerase may act.

Conditions promoting production of closed linear DNA also comprise the presence of a protelomerase and suitable buffering agents/pH and other factors which are required for enzyme performance or stability. Suitable conditions include any conditions used to provide for activity of protelomerase enzymes known in the art. For example, where *E. coli* bacteriophage TelN protelomerase is used, a suitable buffer may be 20 mM Tris HCl, pH 7.6; 5 mM $CaCl_2$; 50 mM potassium glutamate; 0.1 mM EDTA; 1 mM dithiothreitol (DTT). Agents and conditions to maintain optimal activity and stability may also be selected from those listed for DNA polymerases.

In some embodiments, it may be possible to use the same conditions for activity of protelomerase as are used for DNA amplification and/or stem loop structure formation. In particular, use of the same conditions is described where DNA amplification and processing by protelomerase are carried out simultaneously or concurrently. In other embodiments, it may be necessary to change reaction conditions where conditions used to provide optimal DNA polymerase activity lead to sub-optimal protelomerase activity. Removal of specific agents and change in reaction conditions may be achievable by filtration, dialysis and other methods known in the art. The skilled person would readily be able to identify conditions allowing for optimal DNA polymerase activity and/or protelomerase activity.

In a particularly preferred embodiment, for use in amplification of DNA by a strand-displacing polymerase, preferably phi29, the DNA amplification is carried out under buffer conditions substantially identical to or consisting essentially of 35 mM Tris-HCl, 50 mM KCl, 14 mM $MgCl_2$, 10 mM $(NH_4)_2 SO_4$, 4 mM DTT, 1 mM dNTP at a temperature of 25 to 35 degrees centigrade, such as about 30 degrees centigrade. The processing step with protelomerase may then preferably be carried out with TelN, and/or preferably under buffer conditions substantially identical to or consisting essentially of 20 mM Tris HCl, pH 7.6; 5 mM $CaCl_2$; 50 mM potassium glutamate; 0.1 mM EDTA; 1 mM dithiothreitol (DTT) at a temperature of 25 to 35 degrees centigrade, such as about 30 degrees centigrade.

Following production of closed linear DNA by the action of protelomerase, the process of the invention for amplification of closed linear DNA may further comprise a step of purifying the linear covalently closed DNA product. Similarly, DNA amplified according to other processes of the invention may also be purified. The purification referred to above will typically be performed to remove any undesired products. Purification may be carried out by any suitable means known in the art. For example, processing of amplified DNA or linear covalently closed DNA may comprise phenol/chloroform nucleic acid purification or the use of a column which selectively binds nucleic acid, such as those commercially available from Qiagen. The skilled person can routinely identify suitable purification techniques for use in isolation of amplified DNA.

The invention further relates to a kit suitable for performing the method of any aspect or embodiment, said kit comprising:
 (a) a linear, double stranded DNA molecule covalently closed at each end by a portion of a protelomerase recognition sequence, wherein the sequence of said linear, double stranded DNA molecule includes at least one stem loop motif;
 (b) one or more protelomerase enzymes; and optionally;
 (c) a bridging oligonucleotide.

The kit may contain a template closed linear DNA as hereinbefore described, including those with additional protelomerase recognition sequences.

The kit may further comprise one or more of the following components: a DNA polymerase, a primer, appropriate buffers, nucleotides, metal cations, pyrophosphatase and/or nucleases. The linear, double stranded DNA molecule can be any such molecule as described herein.

Figures 10A, 10B:
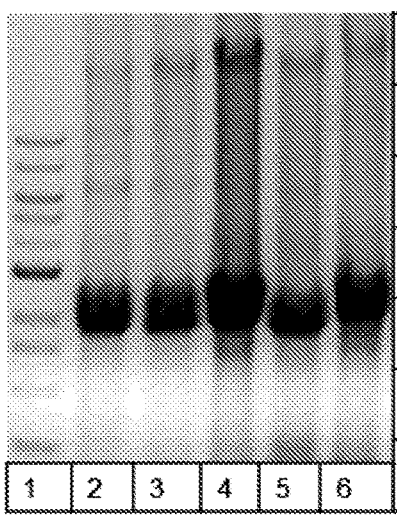
FIG. 10A shows the linear sequence of introduced stem loop used in Example 1 (SEQ ID NO: 31). This also shows the primers used in Example 1 (SEQ ID NO: 32, SEQ ID NO: 33, SEQ ID NO: 34, SEQ ID NO: 35, SEQ ID NO: 36, SEQ ID NO: 37) and the binding position in the loop is shown.
FIG. 10B is a photograph of an 0.8% agarose gel of TelN digest of amplified products produced from different priming strategies.

Sequences of the Invention:
 *Halomonas* phage phiHAP-1 protelomerase nucleic acid sequence (SEQ ID NO:1)
 *Halomonas* phage phiHAP-1 protelomerase amino acid sequence (SEQ ID NO: 2)
 *Yersinia* phage PY54 protelomerase nucleic acid sequence (SEQ ID NO: 3)
 *Yersinia* phage PY54 protelomerase amino acid sequence (SEQ ID NO: 4)
 *Klebsiella* phage phiKO2 protelomerase nucleic acid sequence (SEQ ID NO:5)
 *Klebsiella* phage phiKO2 protelomerase amino acid sequence (SEQ ID NO: 6)
 *Vibrio* phage VP882 protelomerase nucleic acid sequence (SEQ ID NO: 7)
 *Vibrio* phage VP882 protelomerase amino acid sequence (SEQ ID NO: 8)
 *Escherichia coli* bacteriophage N15 telomerase (telN) and Secondary immunity repressor (cA) nucleic acid sequence (SEQ ID NO: 9)
 *Escherichia coli* bacteriophage N15 telomerase amino acid sequence (SEQ ID NO: 10)
 Protelomerase TelA from *Agrobacterium tumefaciens* Strain C58 Native Gene Sequence TelA (1329 bp) (SEQ ID NO: 11)
 TelA Protein Sequence (SEQ ID NO: 12)
 Gp40 VP58.5 nucleotide sequence (SEQ ID NO: 13)
 *Vibrio*: gp40 protein [*Vibrio* phage VP58.5] amino acid (SEQ ID NO 14)
 *Escherichia coli* phage N15 protelomerase recognition sequence (SEQ ID NO 15)
 *Klebsiella* phage phiK02 protelomerase recognition sequence (SEQ ID NO 16)
 *Yersinia enterolytica* phage PY54 protelomerase recognition sequence (SEQ ID NO 17)
 *Vibrio* sp. phage VP882 protelomerase recognition sequence (SEQ ID NO 18)
 *Borrelia burgdorferi* protelomerase recognition sequence (SEQ ID NO 19)
 *Agrobacterium tumefaciens* strain C58 protelomerase recognition sequence (SEQ ID NO 20)
 GP40 VP58.5 recognition sequence: (SEQ ID NO 21)
 *Agrobacterium tumefaciens* strain C58 protelomerase core recognition sequence (SEQ ID NO 22):

Stem-loop sequences: in the format of nucleotide length of each part: stem, spacer, primer binding site, spacer, stem (i.e. for SEQ ID 25, the stem is 25 base pairs in length and there is no spacer to the 15 bases forming the primer binding site):
 SEQ ID 23:25-0-15-0-25
 SEQ ID NO. 24: 25-5-15-5-25
 SEQ ID NO. 25: 25-10-15-0-25
 SEQ ID NO. 26:25-0-15-10-25
 SEQ ID NO 27: 15-0-15-0-15
 SEQ ID NO. 28:15-5-15-5-15
 SEQ ID NO. 29:15-10-15-0-15
 SEQ ID NO 30: 15-0-15-10-15
 SEQ ID NO 31: FIG. 10*a* stem loop
 SEQ ID NO:32: 4 to 11 primer FIG. 10*a*
 SEQ ID NO:33: 3 to 12 primer FIG. 10*a*
 SEQ ID NO:34: 2 to 13 primer FIG. 10*a*
 SEQ ID NO:35: 1 to 14 primer FIG. 10*a*
 SEQ ID NO:36: 0 to 15 primer FIG. 10*a*
 SEQ ID NO: 37: NO-11/short1 primer The invention will now be described with reference to several non-limiting examples:

EXAMPLES

Materials and Methods

Qubit™ fluorometer—Uses fluorescent dyes to detect single stranded (SS)/double stranded (ds) DNA, RNA or protein in a sample. Used in the broad-range dsDNA assay mode, it gives an accurate quantification of dsDNA in a sample without interference from ssDNA such as primers or dNTPs Polyethylene glycol 8000 (PEG8000)—ThermoFisher Scientific, Water—Sigma Aldrich, nuclease-free, deionised and sterilised (molecular biology grade) dNTPs (lithium salt)—Bioline, stock concentration 100 mM, Primers various—Oligofactory, TelN—Enzymatics, ϕ029 DNA—Enzymatics, XbaI—NEB, ApaLI—NEB, T5 exonuclease—NEB, Exonuclease III—Enzymatics, Pyrophosphatase—Enzymatics, Proteinase K-Sigma Aldrich, 10×TLG buffer composition: 300 mM Tris (pH 7.9); 300 mM KCl; 20 mM DTT; 50 mM $(NH_4)_2SO_4$; 75 mM $MgCl_2$—Sigma Aldrich.

Example 1

Figure 11:
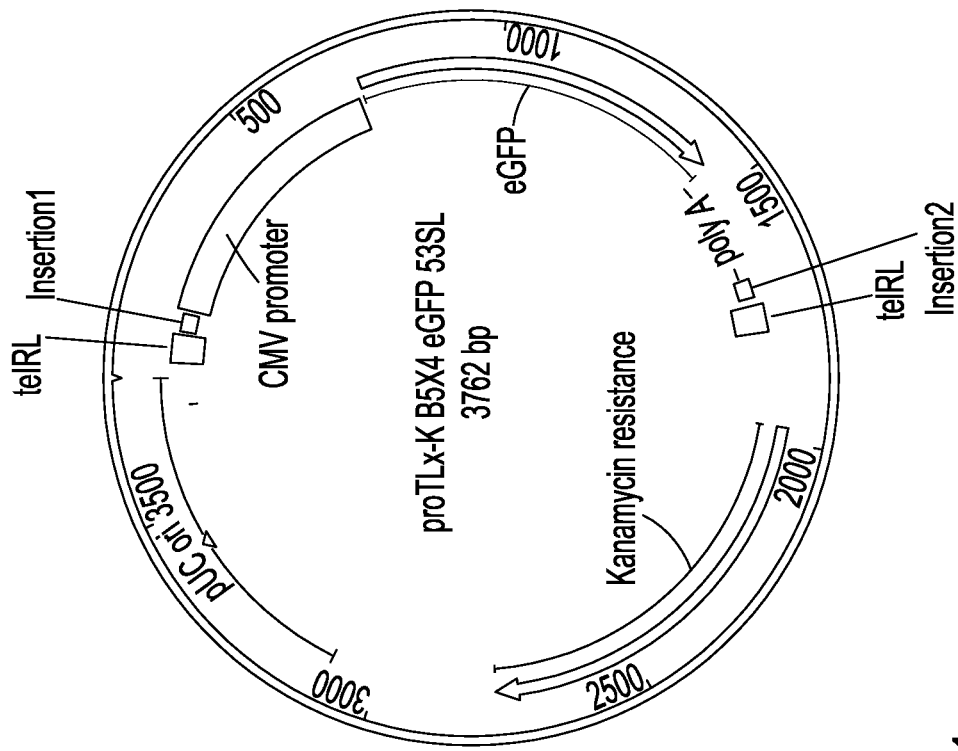
FIG. 11 depicts a plasmid map for the vectors used in Example 1. Various components are depicted.
Figure 11:
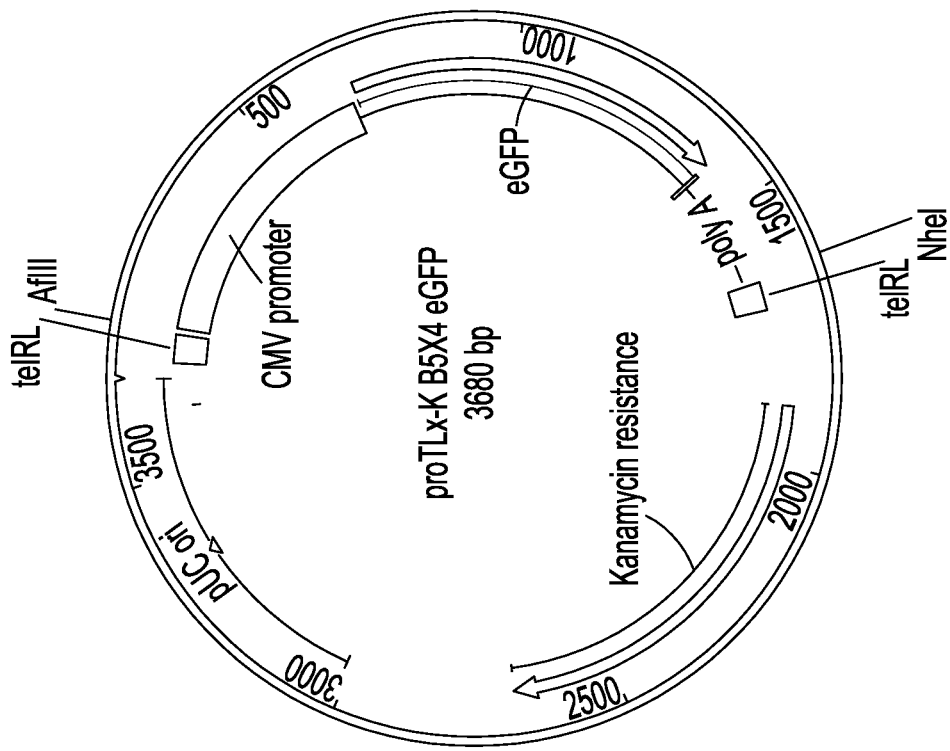

Production of stem loop closed linear DNA from a plasmid template. Table 1 below shows the conditions under which plasmid proTLx-K B5X4 eGFP 53SL (see FIG. 11) was amplified. RCA reactions were setup at room temperature and reagents added in the order indicated. Reactions were carried out in polypropylene tubes and incubated overnight at 30° C.

TABLE 1

Setup conditions for plasmid amplification

| | Reaction Component | Stock concentration | Reaction concentration | Volume added |
|---|---|---|---|---|
| 1 | Template proTLx-K B5X4 eGFP 53SL (see FIG. 11) | 1000 µg/ml | 2 ng/µl | 10 µl |
| 2 | NaOH | 1M | 5 mM | 25 µl |
| 3 | 10 × TLG pH 7.9 buffer (300 mM Tris-HCl), 300 mM KCl, 75 mM MgCl$_2$, 50 mM (NH$_4$)$_2$SO$_4$, 20 mM DTT) | 10x | 1x | 500 µl |
| 4 | Water | n/a | n/a | 4200 µl |
| 5 | dNTPs | 100 mM | 4 mM | 200 µl |
| 6 | Phi29 DNA polymerase | 100,000 U/ml | 200 U/ml | 10 µl |
| 7 | N0-11 primer (SEQ ID NO: 37) (primer binding site is within the palindromic sequence of the protelomerase recognition sequence) | 5 mM | 50 µM | 50 µl |
| 8 | Pyrophosphatase | 2 U/ml | 0.0002 U/ml | 0.5 µl |

Raw concatameric products of amplification of the plasmid template were incubated with 3 µM protelomerase TelN at 30° C. for 10 mins. 750 U/ml of XbaI (NEB) was then added and DNA was incubated at 37° C. for 3 hrs before addition of 500 U/ml of Exonuclease III (Enzymatics) and incubation for a further 2 hours at 37° C. The reaction was then diluted 2 fold in 500 mM NaCl/100 mM MgCl$_2$ buffer, and 2.5% (w/v) polyethylene glycol 8000 (PEG8000) was added. This was centrifuged at 4,500 g for 10 mins and the supernatant recovered. Following addition of 2.5% PEG8000 (final concentration 5%) to the supernatant and a further centrifugation step, the resulting supernatant was discarded and the pellet washed with 5 ml of 100% ethanol. The DNA was re-pelleted by centrifugation, the ethanol discarded and the DNA re-suspended in water. The stem loop containing closed linear DNA (db_eGFP 53SL) was stored at −20° C. and used for the experiments described below Amplification of Stem Loop Closed Linear DNA Experiments indicate that for closed linear DNA amplification using a single primer that binds in the palindromic protelomerase TelN target sequence, no yield increase is possible with dNTP supplementation (see Table 2). This is due to the formation of highly folded concatameric DNA (nanoflowers) as the single strand rolls off the DNA template. This highly folded structure makes priming and further dNTP incorporation more difficult, preventing conversion of DNA nanoflowers into double stranded concatamers.

TABLE 2 dsDNA yield results from feeding of a standard closed linear DNA (db_eGFP)amplification

| No of 2 mM dNTP feeds | None | 1 | 2 |
|---|---|---|---|
| Total [dNTP] | 3.5 mM | 5.5 mM | 7.5 mM |
| [dsDNA] µg/ml | 248 | 270 | 258 |

In order to determine if stem loop priming is beneficial for closed linear DNA amplification, reactions were performed on a dbDNA template with introduced stem loops (db_eGFP 53SL) and primers specific for this region. Table 3 shows the conditions under which stem loop dbDNA amplification was performed.

TABLE 3

Setup conditions for stem loop closed linear DNA amplification

| | Reaction Component | Stock concentration | Reaction concentration | Volume added |
|---|---|---|---|---|
| 1 | Template db_eGFP 53SL | 200 µg/ml | 2 ng/µl | 10 µl |
| 2 | NaOH | 1M | 5 mM | 5 ul |
| 3 | Primer (see FIG. 10a) | 1 mM | 35 µM | 35 µl |
| 4 | 10 × TLG pH 7.9 buffer (300 mM Tris-HCl, 300 mM KCl, 75 mM MgCl$_2$, 50 mM (NH$_4$)$_2$SO$_4$, 20 mM DTT) | 10x | 1x | 100 µl |
| 5 | Water | n/a | n/a | 825 µl |
| 6 | Phi29 DNA polymerase | 100,000 U/ml | 200 U/ml | 2 µl |
| 7 | dNTPs | 100 mM | 2.5 mM | 25 µl |
| 8 | Pyrophosphatase | 2 U/ml | 0.0002 U/ml | 0.1 µl |

Reactions were setup at room temperature and reagents added in the order indicated followed by incubation at 30° C. overnight. 5 different primers specific for the introduced stem loop were tested (see FIG. 10b) in order to determine if priming (and subsequent DNA amplification) in the concatamer stem loops was possible after the initial loop priming in the closed linear DNA template. Reactions were supplemented with 2.5 mM dNTPs at 16 hrs, 40 hrs, 64 hrs and DNA concentrations determined at 15.5 hrs, 39.5 hrs, 63.5 hrs and 87.5 hrs using the Qubit™ fluorometric quantification according to manufacturer's instructions (values for dsDNA are tabulated in Table 4). 8 µl samples of each reaction was also taken for gel analysis on Day 3 and digested with 10 µM protelomerase TelN. For gel analysis, samples were heated to 75° C. for 2 mins before separation on a 0.8% agarose gel using standard procedures.

Table 3 show the dsDNA reaction yield of amplified closed linear DNA after feeding of reactions with dNTPs. In contrast to a standard closed linear DNA amplification (Table 2), it can be seen that for all primers tested, the yield of dsDNA product increases with dNTP additions. This indicates that the concatameric product produced by amplification of the closed linear DNA template (db_eGFP 53SL) is primable and is further amplified to produce more dsDNA product. FIG. 1013 shows that the dsDNA product is converted to a closed linear DNA (db_eGFP 53SL) by treatment with TelN protelomerase. This show that all the primers are specific and are capable of producing the desired closed linear DNA end-product (with included stem loop motif)

TABLE 4 dsDNA yield results from feeding of a stem loop closed linear DNA (db_eGFP) primed with different stem loop specific primers

| No of 2.5 mM dNTP feeds | None | 1 | 2 | 3 |
|---|---|---|---|---|
| Total [dNTP] | 2.5 mM | 5.0 mM | 7.5 mM | 10 mM |
| [dsDNA] µg/ml from 4to11 primer | 208 | 356 | 430 | 810 |
| [dsDNA] µg/ml from 3to12 primer | 193 | 364 | 430 | 890 |
| [dsDNA] µg/ml from 2to13 primer | 382 | 672 | 754 | 2400 |
| [dsDNA] µg/ml from 1to14 primer | 382 | 734 | 664 | 4620 |
| [dsDNA] µg/ml from 0to15 primer | 300 | 426 | 552 | 2560 |

Example 2

Figure 17:
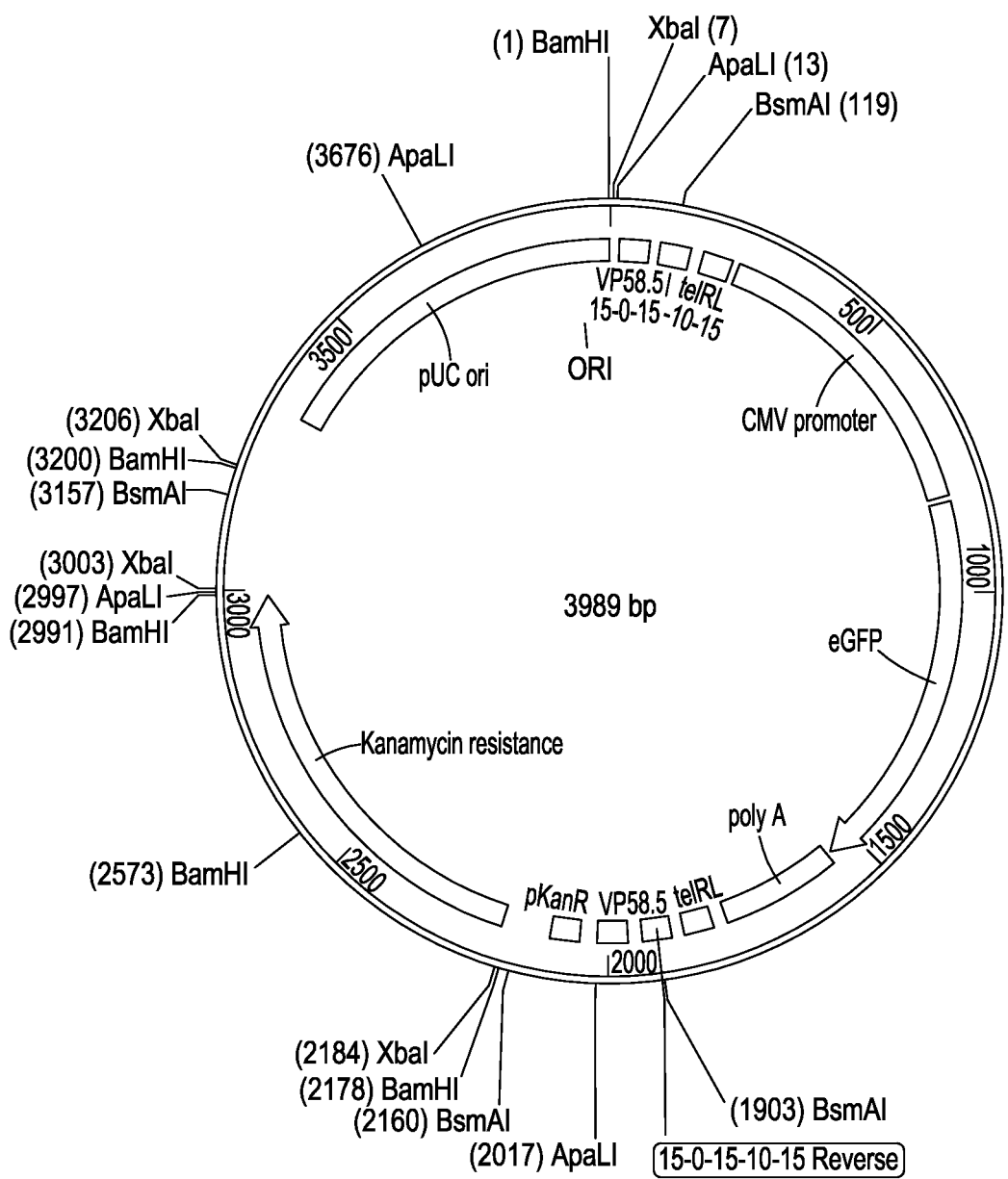
FIG. 17 depicts a map of the plasmid used in Example 2 (proTLx-K B5X4A4 eGFP 15-0-15-10) with the key components depicted. TelRL and VP58.5 represent the recognition sequences for protelomerases TelN and VP58.5 respectively. The sequence depicted as 15-0-15-10-15 and located between telRL and VP58.5 represents the stem loop motif containing an open primer binding site (see FIG. 13).

Production of a Closed Linear DNA with Additional Protelomerase Recognition Sequences from a Plasmid Template Table 4 below shows the conditions under which the plasmid proTLx-K B5X4A4 eGFP 15-0-15-10 (see FIG. 17) was amplified. RCA reactions were setup at room temperature and reagents added in the order indicated. Reactions were carried out in polypropylene tubes and incubated overnight at 30° C.

TABLE 5

Setup conditions for plasmid amplification

| | Reaction Component | Stock concentration | Reaction concentration | Volume added |
|---|---|---|---|---|
| 1 | Template proTLx-K B5X4A4 eGFP 15-0-15-10 (see FIG. 17) | 1000 mg/l | 0.5 mg/l | 2.5 µl |
| 2 | NaOH | 1M | 5 mM | 25 µl |
| 3 | 10 × TLG pH 7.9 buffer (300 mM Tris-HCl), 300 mM KCl, 75 mM MgCl$_2$, 50 mM (NH$_4$)$_2$SO$_4$, 20 mM DTT) | 10x | 1x | 500 µl |
| 4 | Water | n/a | n/a | 4247 µl |
| 5 | dNTPs | 100 mM | 3.5 mM | 175 µl |
| 6 | Phi29 DNA polymerase | 100,000 U/ml | 200 U/ml | 10 µl |
| 7 | 2-13 primer FIG. 10A (2 to 13) | 5 mM | 40 µM | 40 µl |
| 8 | Pyrophosphatase | 2 U/ml | 0.0002 U/ml | 0.5 µl |

Raw concatameric products of amplification of the plasmid template proTLx-K B5X4A4 eGFP 15-0-15-10-15 were incubated with 4 µM protelomerase VP58.5 at 30° C. for 10 mins. 200 U/ml of ApaLI (NEB) was then added and DNA was incubated at 37° C. for 3 hrs before addition of 200 U/ml of Exonuclease III (Enzymatics) and 50 U/ml T5 exonuclease (NEB) and incubation for a further 3 hours at 37° C. 2 µl/ml Proteinase K (Sigma) was added, and the reaction incubated at 37° C. overnight. The reaction was then diluted 2 fold in 500 mM NaCl/100 mM MgCl$_2$ buffer, and 2.5% (w/v) polyethylene glycol 8000 (PEG8000) was added. This was centrifuged at 4,500 g for 10 mins and the supernatant recovered. Following addition of 2.5% PEG8000 (final concentration 5%) to the supernatant and a further centrifugation step, the resulting supernatant was discarded and the pellet washed with 5 ml of 100% ethanol. The DNA was re-pelleted by centrifugation, the ethanol discarded and the DNA re-suspended in water. The closed linear DNA template was stored at −20° C. and used for the experiments described below Example 3

Amplification of a Closed Linear DNA which includes Additional Protelomerase Recognition Sequences.

Essentially, the closed linear DNA template used in this example comprises the generic structure illustrated in FIG. 12. The protelomerase A recognition sequence caps the closed linear DNA while a different protelomerase B recognition sequence is present as a complete site within the double stranded section and is capable of being cleaved and ligated by a cognate protelomerase. The two protelomerase recognition sites are in close proximity but separated by a stem loop motif containing an open single stranded region for binding an oligonucleotide primer to initiate amplification of the template. Amplification of this template by a rolling circle, strand displacing DNA polymerase yields two types of concatameric DNA products: single stranded concatamers that because of their internal sequence complementarity, can fold into nanoflowers as depicted in FIG. 15 and double stranded concatamers where the complementary DNA strand is synthesised following priming and amplification from the nanoflower stem loop motifs. This is similar to the standard stem loop closed linear DNA described in Example 1. However, the use of a closed linear DNA with additional protelomerase recognition sequences (FIG. 12) over a standard stem loop closed linear DNA template (FIG. 9B) has a number of advantages. With reference to FIGS. 14 and 15, treatment with protelomerase B will excise a closed linear DNA (capped with portions of a protelomerase B recognition site) from both a single stranded and double stranded concatamer. In standard rolling circle amplification reactions of closed linear DNA, including the stem loop variant described in Example 1, single stranded concatamer that can be produced in significant amounts is normally a waste product. Thus, use of a closed linear DNA template with additional protelomerase recognition sequences allows a more efficient production of a standard closed linear DNA and allows for the removal of the stem loop motif and the first and second protelomerase recognition sequences, which previously formed the closed ends of the template.

In this embodiment, protelomerases A and B can be any protelomerase or other enzyme capable of cutting and ligating DNA as long as they are two distinct enzymes with different recognition sequences. In the experimental data described below, protelomerase A is VP58.5 and protelomerase B is TelN.

Experimental description: Amplification was carried out as for Example 2, with the exception that template concentration was 1 mg/l. The reaction was also processed as above, minus the ApaLI addition and incubation. The reaction was split in half, with one half processed with VP58.5 and the other, TelN substituted.

Figure 16:
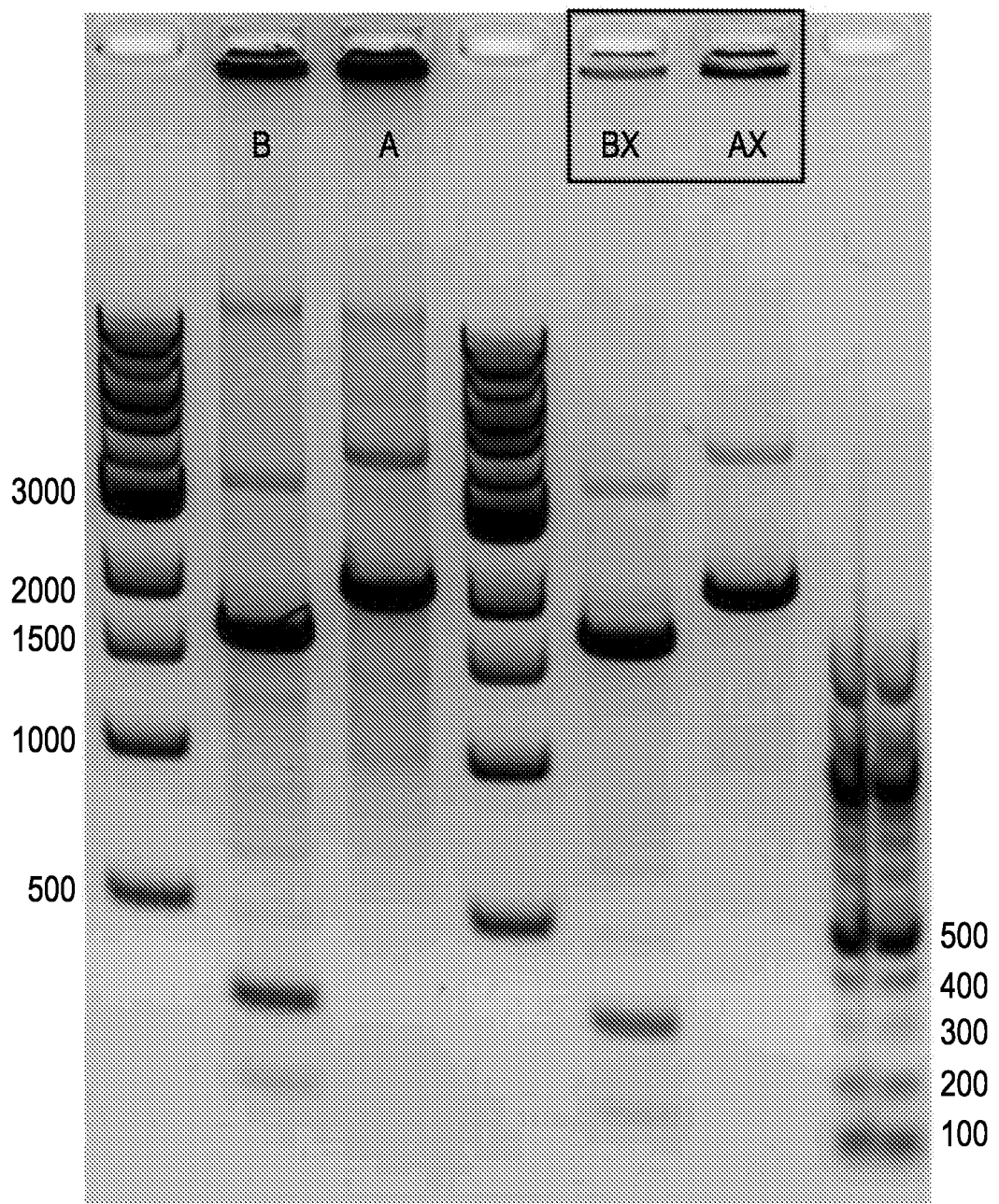
FIG. 16 depicts a gel showing successful cleavage of nanoflowers formed from single stranded concatamers and the cleavage of double stranded concatamers. Lane 'B' is the product of rolling circle amplification cleaved with TelN, showing waste products from cleavage of double stranded concatamers (~300 bp and Z1 on FIG. 14) and nanoflowers (~150 bp and Z2 on FIG. 15) as well as closed linear DNA product (~1600 bp). Lane 'A' shows cleavage of the same reaction with VP58.5, showing full-length template product (~1900 bp) and more uncleaved DNA in wells. Lanes BX and AX show the results of incubation with an exonuclease.

The products were run on a 0.8% agarose gel to check sizes; FIG. 16 shows the protelomerase digest stage showing expected product and sub-products for TelN (lane B) and VP58.5 (lane A) cleavage and joining, and the exonuclease stage (lanes BX and AX respectively) showing progression of the digestion of "open" side products with closed linear DNA constructs remaining intact. As expected from the reaction schematics illustrated in FIGS. 14 and 15 there is less nanoflower DNA left in the wells of TelN treated concatameric DNA than with VP58.5 treated material. This is because TelN converts both double stranded and singled stranded (nanoflower) DNA into desired closed linear DNA product. This closed linear DNA product has no stem loop or VP58.5 recognition sequences, because the action of the TelN removes these entities as it cleaves the "internal" protelomerase target sites, marked as "B" on the figures, or "3" and "4". This result is also reflected in lane BX compared to lane AX following exonuclease treatment.

The invention claimed is:

1. A linear, double stranded DNA molecule covalently closed at each of its ends by a portion of a protelomerase recognition sequence, wherein the portion comprises at least 14 nucleotides of a double stranded palindromic sequence, the linear, double stranded DNA molecule comprises at least one eukaryotic promoter, and wherein the linear, double stranded DNA molecule includes at least one stem loop motif comprising a central non-complementary loop section flanked by two complementary sequences.

2. The linear double stranded DNA molecule as claimed in claim 1, wherein said molecule comprises one or more additional protelomerase recognition sequences.

3. The linear double stranded DNA molecule as claimed in claim 2, wherein said additional protelomerase recognition sequences are separated from the closed ends by the at least one stem loop motif.

* * * * *

SEQUENCE LISTING

<160> NUMBER OF SEQ ID NOS: 37

<210> SEQ ID NO 1
<211> LENGTH: 1563
<212> TYPE: DNA
<213> ORGANISM: Halomonas aquamarina phage phiHAP-1
<220> FEATURE:
<221> NAME/KEY: misc_feature
<223> OTHER INFORMATION: Protelomerase

<400> SEQUENCE: 1

```
atgagcggtg agtcacgtag aaaggtcgat ttagcggaat tgatagagtg gttgctcagc      60
gagatcaaag agatcgacgc cgatgatgag atgccacgta aagagaaaac caagcgcatg     120
gcgcggctgg cacgtagctt caaaacgcgc ctgcatgatg acaagcgccg caaggattct     180
gagcggatcg cggtcacgac ctttcgccgc tacatgacag aagcgcgcaa ggcggtgact     240
gcgcagaact ggcgccatca cagcttcgac cagcagatcg agcggctggc cagccgctac     300
ccggcttatg ccagcaagct ggaagcgctc ggcaagctga ccgatatcag cgccattcgt     360
atggcccacc gcgagctgct cgaccagatc cgcaacgatg acgacgctta tgaggacatc     420
cgggcgatga agctggacca tgaaatcatg cgccacctga cgttgagctc tgcacagaaa     480
agcacgctgg ctgaagaggc cagcgagacg ctggaagagc gcgcggtgaa cacggtcgag     540
atcaactacc actggttgat ggagacggtt tacgagctgc tgagtaaccg ggagagaatg     600
gtcgatgggg agtatcgcgg cttttcagt tacctagcgc ttgggctggc gctggccacc     660
gggcgtcgct cgatcgaggt gctgaagacc ggacggatca cgaaggtggg cgagtatgag     720
ctggagttca gcggccaggc gaaaaagcgc ggcggcgtcg actatagcga ggcttaccac     780
atttataccc tggtgaaagc tgacctggtg atcgaagcgt gggatgagct tcgctcgctg     840
ccggaagctg ctgagctgca gggcatggac aacagcgatg tgaaccgccg cacggcgaag     900
acgctcaaca cgctcactaa gcggatcttt aacaacgatg agcgcgtttt caaggacagc     960
cgggcgatct gggcgcggct ggtgtttgag ctgcacttct cgcgcgacaa gcgctggaag    1020
aaagtcaccg aggacgtgtt ctggcgtgag atgctggggc atgaggacat ggatacacag    1080
cgcagctacc gcgcctttaa aatcgactac gacgagccgg atcaagccga ccaggaagat    1140
tacgaacacg ctagccgcct cgccgcgctg caggcgctgg acggccatga gcagcttgag    1200
agcagcgacg cccaggcgcg tgtgcatgcc tgggtgaaag cgcagatcga gcaggagcct    1260
gacgcgaaaa ttacgcagtc tctgatcagc cgggagctgg gcgtttatcg ccctgccata    1320
aaagcgtacc tggagctggc gcgagaggcg ctcgacgcgc cgaacgtcga tctgacaag    1380 gtcgcggcgg cagtgccgaa ggaagtagcc gaggcgaagc cccggctgaa cgcccaccca    1440
```

```
caaggggatg gcaggtgggt cgggtggct tcaatcaacg ggtggaagt tgcacgggtg   1500 ggcaaccagg caggccggat cgaagcgatg aaagcggcct ataaagcggc gggtgggcgc   1560
tga                                                                 1563
```

<210> SEQ ID NO 2
<211> LENGTH: 520
<212> TYPE: PRT
<213> ORGANISM: Halomonas aquamarina phage phiHAP-1
<220> FEATURE:
<221> NAME/KEY: MISC_FEATURE
<223> OTHER INFORMATION: Protelomerase

<400> SEQUENCE: 2

```
Met Ser Gly Glu Ser Arg Arg Lys Val Asp Leu Ala Glu Leu Ile Glu
1               5                   10                  15

Trp Leu Leu Ser Glu Ile Lys Glu Ile Asp Ala Asp Asp Glu Met Pro
            20                  25                  30

Arg Lys Glu Lys Thr Lys Arg Met Ala Arg Leu Ala Arg Ser Phe Lys
        35                  40                  45

Thr Arg Leu His Asp Asp Lys Arg Lys Asp Ser Glu Arg Ile Ala
    50                  55                  60

Val Thr Thr Phe Arg Arg Tyr Met Thr Glu Ala Arg Lys Ala Val Thr
65                  70                  75                  80

Ala Gln Asn Trp Arg His His Ser Phe Asp Gln Gln Ile Glu Arg Leu
                85                  90                  95

Ala Ser Arg Tyr Pro Ala Tyr Ala Ser Lys Leu Glu Ala Leu Gly Lys
            100                 105                 110

Leu Thr Asp Ile Ser Ala Ile Arg Met Ala His Arg Glu Leu Leu Asp
        115                 120                 125

Gln Ile Arg Asn Asp Asp Ala Tyr Glu Asp Ile Arg Ala Met Lys
    130                 135                 140

Leu Asp His Glu Ile Met Arg His Leu Thr Leu Ser Ser Ala Gln Lys
145                 150                 155                 160

Ser Thr Leu Ala Glu Glu Ala Ser Glu Thr Leu Glu Glu Arg Ala Val
                165                 170                 175

Asn Thr Val Glu Ile Asn Tyr His Trp Leu Met Glu Thr Val Tyr Glu
            180                 185                 190

Leu Leu Ser Asn Arg Glu Arg Met Val Asp Gly Glu Tyr Arg Gly Phe
        195                 200                 205

Phe Ser Tyr Leu Ala Leu Gly Leu Ala Leu Ala Thr Gly Arg Arg Ser
    210                 215                 220

Ile Glu Val Leu Lys Thr Gly Arg Ile Thr Lys Val Gly Glu Tyr Glu
225                 230                 235                 240

Leu Glu Phe Ser Gly Gln Ala Lys Lys Arg Gly Val Asp Tyr Ser
                245                 250                 255

Glu Ala Tyr His Ile Tyr Thr Leu Val Lys Ala Asp Leu Val Ile Glu
            260                 265                 270

Ala Trp Asp Glu Leu Arg Ser Leu Pro Glu Ala Ala Glu Leu Gln Gly
        275                 280                 285

Met Asp Asn Ser Asp Val Asn Arg Arg Thr Ala Lys Thr Leu Asn Thr
    290                 295                 300

Leu Thr Lys Arg Ile Phe Asn Asn Asp Glu Arg Val Phe Lys Asp Ser
305                 310                 315                 320

Arg Ala Ile Trp Ala Arg Leu Val Phe Glu Leu His Phe Ser Arg Asp
                325                 330                 335
```

-continued

```
Lys Arg Trp Lys Lys Val Thr Glu Asp Val Phe Trp Arg Glu Met Leu
                340                 345                 350
Gly His Glu Asp Met Asp Thr Gln Arg Ser Tyr Arg Ala Phe Lys Ile
            355                 360                 365
Asp Tyr Asp Glu Pro Asp Gln Ala Asp Gln Gly Asp Tyr Glu His Ala
        370                 375                 380
Ser Arg Leu Ala Ala Leu Gln Ala Leu Asp Gly His Glu Gln Leu Glu
385                 390                 395                 400
Ser Ser Asp Ala Gln Ala Arg Val His Ala Trp Val Lys Ala Gln Ile
                405                 410                 415
Glu Gln Glu Pro Asp Ala Lys Ile Thr Gln Ser Leu Ile Ser Arg Glu
            420                 425                 430
Leu Gly Val Tyr Arg Pro Ala Ile Lys Ala Tyr Leu Glu Leu Ala Arg
        435                 440                 445
Glu Ala Leu Asp Ala Pro Asn Val Asp Leu Asp Lys Val Ala Ala Ala
450                 455                 460
Val Pro Lys Glu Val Ala Glu Ala Lys Pro Arg Leu Asn Ala His Pro
465                 470                 475                 480
Gln Gly Asp Gly Arg Trp Val Gly Val Ala Ser Ile Asn Gly Val Glu
                485                 490                 495
Val Ala Arg Val Gly Asn Gln Ala Gly Arg Ile Glu Ala Met Lys Ala
            500                 505                 510
Ala Tyr Lys Ala Ala Gly Gly Arg
        515                 520

<210> SEQ ID NO 3
<211> LENGTH: 1854
<212> TYPE: DNA
<213> ORGANISM: Yersinia enterolytica phage PY54
<220> FEATURE:
<221> NAME/KEY: misc_feature
<223> OTHER INFORMATION: Protelomerase

<400> SEQUENCE: 3
atgaaaatcc attttcgcga tttagttagt ggtttagtta agagatcga tgaaatagaa      60 aaatcagacc gggcgcaggg tgacaaaact cggcgttatc agggcgcggc cagaaagttc     120
aaaaatgccg tgtttatgga taacggaaa tatcgcggta acggtatgaa gaatagaata     180
tcgttaacaa catttaataa atatttaagt cgagcacgtt ctcggtttga agaaaggctt     240
caccatagtt ttcctcaatc tatagcaact atctcaaata atatcctgc attcagcgaa     300 ataataaaag atctggataa tagacccgct catgaagtta aataaaact aaagaatta     360 ataactcatc ttgaatccgg tgttaattta ttagaaaaaa taggtagctt agggaaaata     420
aaaccatcta cagctaaaaa aatagttagc ttaaaaaaaa tgtacccatc atgggctaat     480
gatctagata cttaattag tactgaagat gctacagaat acaacaaaa gttagagcaa     540 gggaccgacc tacttaacgc attacattct ctaaaagtaa accatgaagt tatgtatgca     600
ttaacgatgc agccttctga cagagctgca ttaaaagcta ggcatgacgc tgccttcac     660 tttaaaaagc gtaacatcgt acctatcgat tatcccggct atatgcaacg aatgacggac     720
atactacatc ttccagatat agcttttgaa gattcgatgg catcacttgc ccctttagca     780
tttgctctag cagctgctag cggtcgcaga caaattgaaa tactaattac tggtgagttt     840
gacgccaaaa ataaaagcat cattaaattt tctggacaag caaaaaaaag aatggccgtt     900
tcaggtggac attatgaaat atacagtcta attgactcag agctattcat tcaacggtta     960
```

-continued

```
gagtttttac gttctcatag ctcaatactt cgattacaaa atttggaaat agcacatgat    1020
gaacatcgta ctgaactatc tgttattaac ggttttgtag ccaaacccttt aaatgatgca    1080 gcaaaacagt tctttgtcga tgacagaaga gtatttaaag atacccgtgc aatttacgct    1140
cgcatagcat atgaaaaatg gtttagaaca gatcctcgct gggcgaagtg cgacgaagat    1200
gttttcttct ctgaattatt aggccatgac gacccagata ctcagctggc atataaacaa    1260
ttcaagctgg taaatttcaa tccaaaatgg acacctaata tatcagatga aaaccctcgg    1320
ttagctgcac ttcaagagct tgacaatgat atgcccggcc tagcacgtgg cgatgcggca    1380
gttcgcatac atgagtgggt taaagagcaa ctggcgcaga ccctgcggc aaaaataact    1440 gcataccaaa tcaagaaaaa tttaaattgt cgaaatgact tggccagccg atacatggca    1500
tggtgtgctg acgcgctagg ggttgttatt ggtgatgatg acaggcaag gccagaagaa    1560 ctcccaccat cgctcgtgct tgatattaac gctgatgaca ctgacgctga agaagatgaa    1620
atagaggaag actttactga tgaggaaata gacgacaccg aattcgacgt atcagataac    1680
gccagtgatg aagataagcc cgaagataaa cctcgctttg cagcaccaat tcgtagaagt    1740
gaggactctt ggctgattaa atttgaattt gctggcaagc aatatagctg ggagggtaat    1800
gccgaaagtg ttatcgatgc gatgaaacaa gcatggactg aaaatatgga gtaa         1854
```

<210> SEQ ID NO 4
<211> LENGTH: 617
<212> TYPE: PRT
<213> ORGANISM: Yersinia enterolytica phage PY54
<220> FEATURE:
<221> NAME/KEY: MISC_FEATURE
<223> OTHER INFORMATION: Protelomerase

<400> SEQUENCE: 4

```
Met Lys Ile His Phe Arg Asp Leu Val Ser Gly Leu Val Lys Glu Ile
1               5                   10                  15

Asp Glu Ile Glu Lys Ser Asp Arg Ala Gln Gly Asp Lys Thr Arg Arg
            20                  25                  30

Tyr Gln Gly Ala Ala Arg Lys Phe Lys Asn Ala Val Phe Met Asp Lys
        35                  40                  45

Arg Lys Tyr Arg Gly Asn Gly Met Lys Asn Arg Ile Ser Leu Thr Thr
    50                  55                  60

Phe Asn Lys Tyr Leu Ser Arg Ala Arg Ser Arg Phe Glu Glu Arg Leu
65                  70                  75                  80

His His Ser Phe Pro Gln Ser Ile Ala Thr Ile Ser Asn Lys Tyr Pro
                85                  90                  95

Ala Phe Ser Glu Ile Ile Lys Asp Leu Asp Asn Arg Pro Ala His Glu
            100                 105                 110

Val Arg Ile Lys Leu Lys Glu Leu Ile Thr His Leu Glu Ser Gly Val
        115                 120                 125

Asn Leu Leu Glu Lys Ile Gly Ser Leu Gly Lys Ile Lys Pro Ser Thr
    130                 135                 140

Ala Lys Lys Ile Val Ser Leu Lys Lys Met Tyr Pro Ser Trp Ala Asn
145                 150                 155                 160

Asp Leu Asp Thr Leu Ile Ser Thr Glu Asp Ala Thr Glu Leu Gln Gln
                165                 170                 175

Lys Leu Glu Gln Gly Thr Asp Leu Leu Asn Ala Leu His Ser Leu Lys
            180                 185                 190

Val Asn His Glu Val Met Tyr Ala Leu Thr Met Gln Pro Ser Asp Arg
```

```
            195                 200                 205
Ala Ala Leu Lys Ala Arg His Asp Ala Ala Leu His Phe Lys Lys Arg
210                 215                 220

Asn Ile Val Pro Ile Asp Tyr Pro Gly Tyr Met Gln Arg Met Thr Asp
225                 230                 235                 240

Ile Leu His Leu Pro Asp Ile Ala Phe Glu Asp Ser Met Ala Ser Leu
                    245                 250                 255

Ala Pro Leu Ala Phe Ala Leu Ala Ala Ser Gly Arg Arg Gln Ile
            260                 265                 270

Glu Ile Leu Ile Thr Gly Glu Phe Asp Ala Lys Asn Lys Ser Ile Ile
        275                 280                 285

Lys Phe Ser Gly Gln Ala Lys Lys Arg Met Ala Val Ser Gly Gly His
290                 295                 300

Tyr Glu Ile Tyr Ser Leu Ile Asp Ser Glu Leu Phe Ile Gln Arg Leu
305                 310                 315                 320

Glu Phe Leu Arg Ser His Ser Ser Ile Leu Arg Leu Gln Asn Leu Glu
                325                 330                 335

Ile Ala His Asp Glu His Arg Thr Glu Leu Ser Val Ile Asn Gly Phe
            340                 345                 350

Val Ala Lys Pro Leu Asn Asp Ala Ala Lys Gln Phe Phe Val Asp Asp
        355                 360                 365

Arg Arg Val Phe Lys Asp Thr Arg Ala Ile Tyr Ala Arg Ile Ala Tyr
370                 375                 380

Glu Lys Trp Phe Arg Thr Asp Pro Arg Trp Ala Lys Cys Asp Glu Asp
385                 390                 395                 400

Val Phe Phe Ser Glu Leu Leu Gly His Asp Asp Pro Asp Thr Gln Leu
                405                 410                 415

Ala Tyr Lys Gln Phe Lys Leu Val Asn Phe Asn Pro Lys Trp Thr Pro
            420                 425                 430

Asn Ile Ser Asp Glu Asn Pro Arg Leu Ala Ala Leu Gln Glu Leu Asp
        435                 440                 445

Asn Asp Met Pro Gly Leu Ala Arg Gly Asp Ala Ala Val Arg Ile His
    450                 455                 460

Glu Trp Val Lys Glu Gln Leu Ala Gln Asn Pro Ala Ala Lys Ile Thr
465                 470                 475                 480

Ala Tyr Gln Ile Lys Lys Asn Leu Asn Cys Arg Asn Asp Leu Ala Ser
                485                 490                 495

Arg Tyr Met Ala Trp Cys Ala Asp Ala Leu Gly Val Val Ile Gly Asp
            500                 505                 510

Asp Gly Gln Ala Arg Pro Glu Glu Leu Pro Pro Ser Leu Val Leu Asp
        515                 520                 525

Ile Asn Ala Asp Asp Thr Asp Ala Glu Glu Asp Ile Glu Glu Asp
    530                 535                 540

Phe Thr Asp Glu Glu Ile Asp Asp Thr Glu Phe Asp Val Ser Asp Asn
545                 550                 555                 560

Ala Ser Asp Glu Asp Lys Pro Glu Asp Lys Pro Arg Phe Ala Ala Pro
                565                 570                 575

Ile Arg Arg Ser Glu Asp Ser Trp Leu Ile Lys Phe Glu Phe Ala Gly
            580                 585                 590

Lys Gln Tyr Ser Trp Glu Gly Asn Ala Glu Ser Val Ile Asp Ala Met
        595                 600                 605

Lys Gln Ala Trp Thr Glu Asn Met Glu
    610                 615
```

<210> SEQ ID NO 5
<211> LENGTH: 1923
<212> TYPE: DNA
<213> ORGANISM: Klebsiella phage phiKO2
<220> FEATURE:
<221> NAME/KEY: misc_feature
<223> OTHER INFORMATION: Protelomerase

<400> SEQUENCE: 5

| | | | | | |
|---|---|---|---|---|---|
| atgcgtaagg | tgaaaattgg | tgagctaatc | aattcgcttg | tgagcgaggt | cgaggcaatc | 60 |
| gatgcctctg | atcgtccgca | aggcgataaa | acgaagaaaa | ttaaagccgc | agcattaaaa | 120 |
| tataagaatg | cattatttaa | tgacaaaaga | aagtttcgcg | gtaaaggttt | agaaaaaaga | 180 |
| atttctgcca | acacgttcaa | ctcgtatatg | agtcgggcaa | ggaaaagatt | tgatgataga | 240 |
| ttgcatcata | actttgaaaa | gaatgtaatt | aaactatcag | aaaaatatcc | tttatatagt | 300 |
| gaagaattat | cttcgtggct | ttctatgcct | gcggcatcaa | ttagacagca | tatgtcaaga | 360 |
| ttgcaagcca | agctaaaaga | gataatgcca | ttggcagaag | acttatccaa | tataaagatt | 420 |
| ggtacaaaaa | atagcgaagc | aaaaataaat | aaactcgcta | ataaatatcc | tgaatggcaa | 480 |
| ttcgctatta | gtgattttaa | atagcgaagat | tggaaggata | aaagagatta | tctttataaa | 540 |
| ctattccaac | aaggttcttc | gctcctggaa | gacttgaata | acctgaaagt | aaaccatgag | 600 |
| gttctctatc | atctgcagct | tagttctgcc | gagcgaacct | ctatccagca | gcgctgggcc | 660 |
| aacgtcctca | gcgagaaaaa | gcgcaacgtt | gtcgtgattg | actatccgcg | ctatatgcag | 720 |
| gccatctacg | atataatcaa | caagcctata | gtttcgttcg | atttgactac | tcgtcgtggt | 780 |
| atggccccgc | tggcgttcgc | ccttccgcg | ctatctggtc | gccgaatgat | tgaaatcatg | 840 |
| ctccaggtg | aattttccgt | cgcaggtaaa | tatacagtaa | cattcctggg | gcaagctaaa | 900 |
| aaacgctcgg | aagataaagg | tatatcaagg | aaaatatata | ccttatgcga | cgctacttta | 960 |
| tttgttagtt | tggtaaatga | acttcgctca | tgccccgctg | ctgcggattt | tgatgaagta | 1020 |
| ataaaaggat | atggcgaaaa | tgacactcgc | tcagaaaatg | ggcgtattaa | tgcaattctc | 1080 |
| gctacagctt | ttaatccgtg | ggtaaaaact | ttcttaggcg | atgaccgccg | cgtttataaa | 1140 |
| gatagccgcg | ctatttacgc | ccgtattgcc | tatgaaatgt | tcttccgcgt | tgaccctcgg | 1200 |
| tggaagaatg | ttgatgagga | tgtattcttc | atggagattc | tcggccatga | cgatgaaaac | 1260 |
| acccaactgc | actataagca | gtttaaattg | gctaacttct | ccagaacatg | gcgaccaaat | 1320 |
| gtcggcgagg | agaatgcccg | cctagcggcg | ctgcaaaagc | tggatagcat | gatgccagat | 1380 |
| tttgccaggg | gcgacgccgg | ggttcgtatt | catgagaccg | tgaagcagct | ggtggagcag | 1440 |
| gacccatcga | taaaaatcac | aaacagcacc | ctgcgaccgt | ttaacttcag | taccaggctg | 1500 |
| attcctcgct | acctggagtt | tgccgccgat | gcattgggcc | agttcgtcgg | tgaaaatggg | 1560 |
| caatggcaac | tgaaggatga | ggcgcctgca | atagtcctgc | ctgatgagga | aattcttgag | 1620 |
| cctatggacg | acgtcgatct | cgatgacgaa | accatgatga | tgaaacgct | ggatgacgat | 1680 |
| gagatcgaag | tggacgaaag | cgaaggagag | gaactggagg | aagcgggcga | cgctgaagag | 1740 |
| gccgaggtgg | ctgaacagga | agagaagcac | cctggcaagc | caaactttaa | agcgccgagg | 1800 |
| gataatggcg | atggtaccta | catggtggaa | tttgaattcg | gtggccgtca | ttacgcctgg | 1860 |
| tccggtgccg | ccggtaatcg | ggtagaggca | atgcaatctg | cctggagtgc | ctacttcaag | 1920 |
| tga | | | | | 1923 |

<210> SEQ ID NO 6
<211> LENGTH: 640
<212> TYPE: PRT
<213> ORGANISM: Klebsiella phage phiKO2
<220> FEATURE:
<221> NAME/KEY: MISC_FEATURE
<223> OTHER INFORMATION: Protelomerase

<400> SEQUENCE: 6

```
Met Arg Lys Val Lys Ile Gly Glu Leu Ile Asn Ser Leu Val Ser Glu
1               5                   10                  15

Val Glu Ala Ile Asp Ala Ser Asp Arg Pro Gln Gly Asp Lys Thr Lys
            20                  25                  30

Lys Ile Lys Ala Ala Ala Leu Lys Tyr Lys Asn Ala Leu Phe Asn Asp
        35                  40                  45

Lys Arg Lys Phe Arg Gly Lys Gly Leu Glu Lys Arg Ile Ser Ala Asn
    50                  55                  60

Thr Phe Asn Ser Tyr Met Ser Arg Ala Arg Lys Arg Phe Asp Asp Arg
65                  70                  75                  80

Leu His His Asn Phe Glu Lys Asn Val Ile Lys Leu Ser Glu Lys Tyr
                85                  90                  95

Pro Leu Tyr Ser Glu Glu Leu Ser Ser Trp Leu Ser Met Pro Ala Ala
            100                 105                 110

Ser Ile Arg Gln His Met Ser Arg Leu Gln Ala Lys Leu Lys Glu Ile
        115                 120                 125

Met Pro Leu Ala Glu Asp Leu Ser Asn Ile Lys Ile Gly Thr Lys Asn
    130                 135                 140

Ser Glu Ala Lys Ile Asn Lys Leu Ala Asn Lys Tyr Pro Glu Trp Gln
145                 150                 155                 160

Phe Ala Ile Ser Asp Leu Asn Ser Glu Asp Trp Lys Asp Lys Arg Asp
                165                 170                 175

Tyr Leu Tyr Lys Leu Phe Gln Gln Gly Ser Ser Leu Leu Glu Asp Leu
            180                 185                 190

Asn Asn Leu Lys Val Asn His Glu Val Leu Tyr His Leu Gln Leu Ser
        195                 200                 205

Ser Ala Glu Arg Thr Ser Ile Gln Gln Arg Trp Ala Asn Val Leu Ser
    210                 215                 220

Glu Lys Lys Arg Asn Val Val Ile Asp Tyr Pro Arg Tyr Met Gln
225                 230                 235                 240

Ala Ile Tyr Asp Ile Ile Asn Lys Pro Ile Val Ser Phe Asp Leu Thr
                245                 250                 255

Thr Arg Arg Gly Met Ala Pro Leu Ala Phe Ala Leu Ala Ala Leu Ser
            260                 265                 270

Gly Arg Arg Met Ile Glu Ile Met Leu Gln Gly Glu Phe Ser Val Ala
        275                 280                 285

Gly Lys Tyr Thr Val Thr Phe Leu Gly Gln Ala Lys Lys Arg Ser Glu
    290                 295                 300

Asp Lys Gly Ile Ser Arg Lys Ile Tyr Thr Leu Cys Asp Ala Thr Leu
305                 310                 315                 320

Phe Val Ser Leu Val Asn Glu Leu Arg Ser Cys Pro Ala Ala Ala Asp
                325                 330                 335

Phe Asp Glu Val Ile Lys Gly Tyr Gly Glu Asn Asp Thr Arg Ser Glu
            340                 345                 350

Asn Gly Arg Ile Asn Ala Ile Leu Ala Thr Ala Phe Asn Pro Trp Val
        355                 360                 365
```

| Lys | Thr | Phe | Leu | Gly | Asp | Asp | Arg | Arg | Val | Tyr | Lys | Asp | Ser | Arg | Ala |
|---|---|---|---|---|---|---|---|---|---|---|---|---|---|---|---|
| 370 | | | | | 375 | | | | | 380 | | | | | |

Ile Tyr Ala Arg Ile Ala Tyr Glu Met Phe Phe Arg Val Asp Pro Arg
385                 390                 395                 400

Trp Lys Asn Val Asp Glu Asp Val Phe Phe Met Glu Ile Leu Gly His
            405                 410                 415

Asp Asp Glu Asn Thr Gln Leu His Tyr Lys Gln Phe Lys Leu Ala Asn
        420                 425                 430

Phe Ser Arg Thr Trp Arg Pro Asn Val Gly Glu Asn Ala Arg Leu
    435                 440                 445

Ala Ala Leu Gln Lys Leu Asp Ser Met Met Pro Asp Phe Ala Arg Gly
450                 455                 460

Asp Ala Gly Val Arg Ile His Glu Thr Val Lys Gln Leu Val Glu Gln
465             470                 475                 480

Asp Pro Ser Ile Lys Ile Thr Asn Ser Thr Leu Arg Pro Phe Asn Phe
                485             490                 495

Ser Thr Arg Leu Ile Pro Arg Tyr Leu Glu Phe Ala Ala Asp Ala Leu
            500                 505                 510

Gly Gln Phe Val Gly Glu Asn Gly Gln Trp Gln Leu Lys Asp Glu Ala
        515                 520                 525

Pro Ala Ile Val Leu Pro Asp Glu Glu Ile Leu Glu Pro Met Asp Asp
    530                 535                 540

Val Asp Leu Asp Asp Glu Asn His Asp Asp Glu Thr Leu Asp Asp Asp
545                 550                 555                 560

Glu Ile Glu Val Asp Glu Ser Glu Gly Glu Glu Leu Glu Glu Ala Gly
            565                 570                 575

Asp Ala Glu Glu Ala Glu Val Ala Glu Gln Glu Glu Lys His Pro Gly
        580                 585                 590

Lys Pro Asn Phe Lys Ala Pro Arg Asp Asn Gly Asp Gly Thr Tyr Met
    595                 600                 605

Val Glu Phe Glu Phe Gly Gly Arg His Tyr Ala Trp Ser Gly Ala Ala
610                 615                 620

Gly Asn Arg Val Glu Ala Met Gln Ser Ala Trp Ser Ala Tyr Phe Lys
625                 630                 635                 640

<210> SEQ ID NO 7
<211> LENGTH: 1617
<212> TYPE: DNA
<213> ORGANISM: Vibrio sp. phage VP882
<220> FEATURE:
<221> NAME/KEY: misc_feature
<223> OTHER INFORMATION: Protelomerase

<400> SEQUENCE: 7

```
atgagcggcg aaagtagaca aaaggtaaac ctcgaggagt taataaatga gctcgtcgag      60
gaggtgaaaa ccatcgatga caatgaggcg attactcggt ctgaaaaaac caagttgatc     120
accagggcgg cgactaaatt caagaccaag ctgcacgacg ataagcgccg gaaggatgcg     180
accagaatcg ctctgagcac ctatcgtaag tacatgacaa tggccagggc agcagttact     240
gagcagaact ggaaacacca cagtctcgag cagcagatag agcggctggc caaaaagcac     300
ccgcaatacg ctgagcagct ggtggccatc ggggccatgg ataacatcac cgagttgcgc     360
ctggcgcatc gcgacctcct gaagagcatc aaggacaacg atgaagcctt cgaggatatc     420
cgcagcatga agttagacca cgaggtaatg cgccatctga cgctaccagt gcgcaaaag      480
gcgagactgg cagaggaagc cgccgaggcg ttgaccgaga agaaaaccgc cacggtcgac     540
```

```
atcaactatc acgagctgat ggccggcgtg gtggagctgt tgaccaagaa gaccaagacg    600
gtcggcagcg acagcaccta cagcttcagc cggctggcgc ttggtattgg cctggctacc    660
ggtcgtcgtt ctatcgagat actgaagcag ggcgagttca aaaggtgga tgagcagcgg    720
ctcgagttct ctggccaagc gaaaaagcgc ggcggtgccg actattcaga gacctatacc    780
atttacaccc tggtcgactc cgacctggta ctgatggcgc tgaagaacct gcgagagttg    840
ccagaagttc gcgcactgga tgagtacgac caactgggcg agattaagcg gaacgacgcc    900
atcaataaac gctgtgcaaa acgctcaac caaaccgcca agcagttctt tggcagcgac     960
gagcgcgtgt tcaaagatag tcgtgccatc tgggcgcgtc tggcttatga gttgtttttt   1020
caacgtgatc cgcgctggaa aaagaaagac gaggacgttt tctggcagga gatgctgggc   1080
cacgaggaca tcgagactca gaaagcctat aagcaattca aggtcgacta cagcgaacct   1140
gagcagccgg tgcacaagcc tggcaaattt aagagcagag ctgaagccct cgcggcgctc   1200
gactcaaatg aggacattac cacccgctca tccatggcca agatccacga ctgggtgaaa   1260
gagcgtattg cggaagaccc cgaggcgaac atcacacagt cactcatcac ccgggaactg   1320
ggctcaggcc gtaaggtgat caaggactac ctcgacctgg ctgacgatgc ccttgctgtg   1380
gtgaatactc ctgtcgatga cgcagtcgtc gaggttccag ctgatgtgcc ggcagcagaa   1440
aaacagccga agaaagcgca gaagcccaga ctcgtggctc accaggttga tgatgagcac   1500
tgggaagcct gggcgctggt ggaaggcgag gaggtggcca gggtgaaaat caagggcacc   1560
cgcgttgagg caatgacagc cgcatgggag gccagccaaa aggcactcga tgactaa     1617
```

<210> SEQ ID NO 8
<211> LENGTH: 538
<212> TYPE: PRT
<213> ORGANISM: Vibrio sp. phage VP882
<220> FEATURE:
<221> NAME/KEY: MISC_FEATURE
<223> OTHER INFORMATION: Protelomerase

<400> SEQUENCE: 8

Met Ser Gly Glu Ser Arg Gln Lys Val Asn Leu Glu Glu Leu Ile Asn
1               5                   10                  15

Glu Leu Val Glu Val Lys Thr Ile Asp Asp Asn Glu Ala Ile Thr
            20                  25                  30

Arg Ser Glu Lys Thr Lys Leu Ile Thr Arg Ala Ala Thr Lys Phe Lys
        35                  40                  45

Thr Lys Leu His Asp Asp Lys Arg Arg Lys Asp Ala Thr Arg Ile Ala
    50                  55                  60

Leu Ser Thr Tyr Arg Lys Tyr Met Thr Met Ala Arg Ala Ala Val Thr
65                  70                  75                  80

Glu Gln Asn Trp Lys His His Ser Leu Glu Gln Gln Ile Glu Arg Leu
                85                  90                  95

Ala Lys Lys His Pro Gln Tyr Ala Glu Gln Leu Val Ala Ile Gly Ala
            100                 105                 110

Met Asp Asn Ile Thr Glu Leu Arg Leu Ala His Arg Asp Leu Leu Lys
        115                 120                 125

Ser Ile Lys Asp Asn Asp Glu Ala Phe Glu Asp Ile Arg Ser Met Lys
    130                 135                 140

Leu Asp His Glu Val Met Arg His Leu Thr Leu Pro Ser Ala Gln Lys
145                 150                 155                 160

Ala Arg Leu Ala Glu Glu Ala Ala Glu Ala Leu Thr Glu Lys Lys Thr 165                 170                 175
Ala Thr Val Asp Ile Asn Tyr His Glu Leu Met Ala Gly Val Val Glu
            180                 185                 190
Leu Leu Thr Lys Lys Thr Lys Thr Val Gly Ser Asp Ser Thr Tyr Ser
        195                 200                 205
Phe Ser Arg Leu Ala Leu Gly Ile Gly Leu Ala Thr Gly Arg Arg Ser
    210                 215                 220
Ile Glu Ile Leu Lys Gln Gly Glu Phe Lys Lys Val Asp Glu Gln Arg
225                 230                 235                 240
Leu Glu Phe Ser Gly Gln Ala Lys Lys Arg Gly Gly Ala Asp Tyr Ser
                245                 250                 255
Glu Thr Tyr Thr Ile Tyr Thr Leu Val Asp Ser Asp Leu Val Leu Met
            260                 265                 270
Ala Leu Lys Asn Leu Arg Glu Leu Pro Glu Val Arg Ala Leu Asp Glu
        275                 280                 285
Tyr Asp Gln Leu Gly Glu Ile Lys Arg Asn Asp Ala Ile Asn Lys Arg
    290                 295                 300
Cys Ala Lys Thr Leu Asn Gln Thr Ala Lys Gln Phe Phe Gly Ser Asp
305                 310                 315                 320
Glu Arg Val Phe Lys Asp Ser Arg Ala Ile Trp Ala Arg Leu Ala Tyr
                325                 330                 335
Glu Leu Phe Phe Gln Arg Asp Pro Arg Trp Lys Lys Lys Asp Glu Asp
            340                 345                 350
Val Phe Trp Gln Glu Met Leu Gly His Glu Asp Ile Glu Thr Gln Lys
        355                 360                 365
Ala Tyr Lys Gln Phe Lys Val Asp Tyr Ser Glu Pro Glu Gln Pro Val
    370                 375                 380
His Lys Pro Gly Lys Phe Lys Ser Arg Ala Glu Ala Leu Ala Ala Leu
385                 390                 395                 400
Asp Ser Asn Glu Asp Ile Thr Thr Arg Ser Ser Met Ala Lys Ile His
                405                 410                 415
Asp Trp Val Lys Glu Arg Ile Ala Glu Asp Pro Glu Ala Asn Ile Thr
            420                 425                 430
Gln Ser Leu Ile Thr Arg Glu Leu Gly Ser Gly Arg Lys Val Ile Lys
        435                 440                 445
Asp Tyr Leu Asp Leu Ala Asp Asp Ala Leu Ala Val Asn Thr Pro
    450                 455                 460
Val Asp Asp Ala Val Val Glu Val Pro Ala Asp Val Pro Ala Ala Glu
465                 470                 475                 480
Lys Gln Pro Lys Lys Ala Gln Lys Pro Arg Leu Val Ala His Gln Val
                485                 490                 495
Asp Asp Glu His Trp Glu Ala Trp Ala Leu Val Glu Gly Glu Val
            500                 505                 510
Ala Arg Val Lys Ile Lys Gly Thr Arg Val Glu Ala Met Thr Ala Ala
        515                 520                 525
Trp Glu Ala Ser Gln Lys Ala Leu Asp Asp
    530                 535

<210> SEQ ID NO 9
<211> LENGTH: 4055
<212> TYPE: DNA
<213> ORGANISM: Escherichia coli bacteriophage N15
<220> FEATURE:
<221> NAME/KEY: misc_feature
<223> OTHER INFORMATION: Proteolomerase TelN

<400> SEQUENCE: 9

```
catatgcact atatcatatc tcaattacgg aacatatcag cacacaattg cccattatac    60
gcgcgtataa tggactattg tgtgctgata aggagaacat aagcgcagaa caatatgtat   120
ctattccggt gttgtgttcc tttgttattc tgctattatg ttctcttata gtgtgacgaa   180
agcagcataa ttaatcgtca cttgttcttt gattgtgtta cgatatccag agacttagaa   240
acgggggaac cggatgagc aaggtaaaaa tcggtgagtt gatcaacacg cttgtgaatg    300
aggtagaggc aattgatgcc tcagaccgcc cacaaggcga caaaacgaag agaattaaag   360
ccgcagccgc acgtataag aacgcgttat ttaatgataa agaaagttc cgtgggaaag     420
gattgcagaa aagaataacc gcgaatactt ttaacgccta tatgagcagg gcaagaaagc   480
ggtttgatga taaattacat catagctttg ataaaaatat taataaatta tcggaaaagt   540
atcctcttta cagcgaagaa ttatcttcat ggctttctat gcctacggct aatattcgcc   600
agcacatgtc atcgttacaa tctaaattga agaaataat gccgcttgcc gaagagttat    660
caaatgtaag aataggctct aaaggcagtg atgcaaaaat agcaagacta ataaaaaat    720
atccagattg gagttttgct cttagtgatt taaacagtga tgattggaag gagcgccgtg   780
actatcttta taagttattc caacaaggct ctgcgttgtt agaagaacta caccagctca   840
aggtcaacca tgaggttctg taccatctgc agctaagccc tgcggagcgt acatctatac   900
agcaacgatg ggccgatgtt ctgcgcgaga agaagcgtaa tgttgtggtt attgactacc   960
caacatacat gcagtctatc tatgatattt tgaataatcc tgcgacttta tttagtttaa  1020
acactcgttc tggaatggca cctttggcct ttgctctggc tgcggtatca gggcgaagaa  1080
tgattgagat aatgtttcag ggtgaatttg ccgtttcagg aaagtatacg gttaatttct  1140
cagggcaagc taaaaaacgc tctgaagata aaagcgtaac cagaacgatt tatactttat  1200
gcgaagcaaa attattcgtt gaattattaa cagaattgcg ttcttgctct gctgcatctg  1260
atttcgatga ggttgttaaa ggatatggaa aggatgatac aaggtctgag aacggcagga  1320
taaatgctat tttagcaaaa gcatttaacc cttgggttaa atcatttttc ggcgatgacc  1380
gtcgtgttta taaagatagc cgcgctattt acgctcgcat cgcttatgag atgttcttcc  1440
gcgtcgatcc acggtggaaa aacgtcgacg aggatgtgtt cttcatggag attctcggac  1500
acgacgatga gaacacccag ctgcactata agcagttcaa gctggccaac ttctccagaa  1560
cctggcgacc tgaagttggg gatgaaaaca ccaggctggt ggctctgcag aaactggacg  1620
atgaaatgcc aggctttgcc agaggtgacg ctggcgtccg tctccatgaa accgttaagc  1680
agctggtgga gcaggaccca tcagcaaaaa taaccaacag cactctccgg gcctttaaat  1740
ttagcccgac gatgattagc cggtacctgg agtttgccgc tgatgcattg gggcagttcg  1800
ttggcgagaa cgggcagtgg cagctgaaga tagagacacc tgcaatcgtc ctgcctgatg  1860
aagaatccgt tgagaccatc gacgaaccgg atgatgagtc caagacgac gagctggatg   1920
aagatgaaat tgagctcgac gagggtggcg gcgatgaacc aaccgaagag gaagggccag  1980
aagaacatca gccaactgct ctaaaacccg tcttcaagcc tgcaaaaaat aacggggacg  2040
gaacgtacaa gatagagttt gaatacgatg gaaagcatta tgcctggtcc ggccccgccg  2100
atagccctat ggccgcaatg cgatccgcat gggaaacgta ctacagctaa agaaaagcc   2160
accggtgtta atcggtggct tttttattga ggcctgtccc tacccatccc tgcaagggga  2220
cggaaggatt aggcggaaac tgcagctgca actacggaca tcgccgtccc gactgcaggg  2280
```

```
acttccccgc gtaaagcggg gcttaaattc gggctggcca accctatttt tctgcaatcg    2340
ctggcgatgt tagtttcgtg gatagcgttt ccagcttttc aatggccagc tcaaaatgtg    2400
ctggcagcac cttctccagt tccgtatcaa tatcggtgat cggcagctct ccacaagaca    2460
tactccggcg accgcacga actacatcgc gcagcagctc ccgttcgtag acacgcatgt    2520
tgcccagagc cgtttctgca gccgttaata tccggcgcac gtcggcgatg attgccggga    2580
gatcatccac ggttattggg ttcggtgatg ggttcctgca ggcgcggcgg agagccatcc    2640
agacgccgct aacccatgcg ttacggtact gaaaactttg tgctatgtcg tttatcaggc    2700
ccgaagttct tctttctgcc gccagtccag tggttcaccg gcgttcttag gctcaggctc    2760
gacaaaagca tactcgccgt ttttccggat agctggcaga acctcgttcg tcacccactt    2820
gcggaaccgc caggctgtcg tccctgttt caccgcgtcg cggcagcgga ggattatggt    2880
gtagagacca gattccgata ccacatttac ttccctggcc atccgatcaa gttttttgtgc   2940 ctcggttaaa ccgagggtca attttcatc atgatccagc ttacgcaatg catcagaagg    3000
gttggctata ttcaatgcag cacagatatc cagcgccaca aaccacgggt caccaccgac    3060
aagaaccacc cgtatagggt ggctttcctg aaatgaaaag acggagagag ccttcattgc    3120
gcctccccgg atttcagctg ctcagaaagg gacagggagc agccgcgagc ttcctgcgtg    3180
agttcgcgcg cgacctgcag aagttccgca gcttcctgca aatacagcgt ggcctcataa    3240
ctggagatag tgcggtgagc agagcccaca agcgcttcaa cctgcagcag gcgttcctca    3300
atcgtctcca gcaggccctg ggcgtttaac tgaatctggt tcatgcgatc acctcgctga    3360
ccgggatacg ggctgacaga acgaggacaa aacggctggc gaactggcga cgagcttctc    3420
gctcggatga tgcaatggtg gaaggcggt ggatatggga ttttttgtcc gtgcggacga    3480
cagctgcaaa tttgaatttg aacatggtat gcattcctat cttgtatagg gtgctaccac    3540
cagagttgag aatctctata ggggtggtag cccagacagg gttctcaaca ccggtacaag    3600
aagaaaccgg cccaaccgaa gttggccca tctgagccac cataattcag gtatgcgcag    3660
atttaacaca caaaaaaaca cgctggcgcg tgttgtgcgc ttcttgtcat tcggggttga    3720
gaggcccggc tgcagatttt gctgcagcgg ggtaactcta ccgccaaagc agaacgcacg    3780
tcaataattt aggtggatat tttaccccgt gaccagtcac gtgcacaggt gtttttatag    3840
tttgctttac tgactgatca gaacctgatc agttattgga gtccggtaat cttattgatg    3900
accgcagcca ccttagatgt tgtctcaaac cccatacggc cacgaatgag ccactggaac    3960
ggaatagtca gcaggtacag cggaacgaac cacaaacggt tcagacgctg ccagaacgtc    4020
gcatcacgac gttccatcca ttcggtattg tcgac                              4055
```

<210> SEQ ID NO 10
<211> LENGTH: 631
<212> TYPE: PRT
<213> ORGANISM: Escherichia coli bacteriophage N15
<220> FEATURE:
<221> NAME/KEY: misc_feature
<223> OTHER INFORMATION: Proteolmerase sequence Tel N

<400> SEQUENCE: 10

Met Ser Lys Val Lys Ile Gly Glu Leu Ile Asn Thr Leu Val Asn Glu
1               5                   10                  15

Val Glu Ala Ile Asp Ala Ser Asp Arg Pro Gln Gly Asp Lys Thr Lys
            20                  25                  30

Arg Ile Lys Ala Ala Ala Ala Arg Tyr Lys Asn Ala Leu Phe Asn Asp
        35                  40                  45

```
Lys Arg Lys Phe Arg Gly Lys Gly Leu Gln Lys Arg Ile Thr Ala Asn
         50                  55                  60

Thr Phe Asn Ala Tyr Met Ser Arg Ala Arg Lys Arg Phe Asp Asp Lys
 65              70                  75                  80

Leu His His Ser Phe Asp Lys Asn Ile Asn Lys Leu Ser Glu Lys Tyr
                 85                  90                  95

Pro Leu Tyr Ser Glu Glu Leu Ser Ser Trp Leu Ser Met Pro Thr Ala
            100                 105                 110

Asn Ile Arg Gln His Met Ser Ser Leu Gln Ser Lys Leu Lys Glu Ile
            115                 120                 125

Met Pro Leu Ala Glu Glu Leu Ser Asn Val Arg Ile Gly Ser Lys Gly
    130                 135                 140

Ser Asp Ala Lys Ile Ala Arg Leu Ile Lys Lys Tyr Pro Asp Trp Ser
145             150                 155                 160

Phe Ala Leu Ser Asp Leu Asn Ser Asp Trp Lys Glu Arg Arg Asp
                165                 170                 175

Tyr Leu Tyr Lys Leu Phe Gln Gln Gly Ser Ala Leu Leu Glu Glu Leu
            180                 185                 190

His Gln Leu Lys Val Asn His Glu Val Leu Tyr His Leu Gln Leu Ser
        195                 200                 205

Pro Ala Glu Arg Thr Ser Ile Gln Gln Arg Trp Ala Asp Val Leu Arg
    210                 215                 220

Glu Lys Lys Arg Asn Val Val Ile Asp Tyr Pro Thr Tyr Met Gln
225             230                 235                 240

Ser Ile Tyr Asp Ile Leu Asn Asn Pro Ala Thr Leu Phe Ser Leu Asn
                245                 250                 255

Thr Arg Ser Gly Met Ala Pro Leu Ala Phe Ala Leu Ala Ala Val Ser
            260                 265                 270

Gly Arg Arg Met Ile Glu Ile Met Phe Gln Gly Glu Phe Ala Val Ser
        275                 280                 285

Gly Lys Tyr Thr Val Asn Phe Ser Gly Gln Ala Lys Lys Arg Ser Glu
    290                 295                 300

Asp Lys Ser Val Thr Arg Thr Ile Tyr Thr Leu Cys Glu Ala Lys Leu
305             310                 315                 320

Phe Val Glu Leu Leu Thr Glu Leu Arg Ser Cys Ser Ala Ala Ser Asp
                325                 330                 335

Phe Asp Glu Val Val Lys Gly Tyr Gly Lys Asp Asp Thr Arg Ser Glu
            340                 345                 350

Asn Gly Arg Ile Asn Ala Ile Leu Ala Lys Ala Phe Asn Pro Trp Val
        355                 360                 365

Lys Ser Phe Phe Gly Asp Asp Arg Arg Val Tyr Lys Asp Ser Arg Ala
    370                 375                 380

Ile Tyr Ala Arg Ile Ala Tyr Glu Met Phe Phe Arg Val Asp Pro Arg
385             390                 395                 400

Trp Lys Asn Val Asp Glu Val Phe Phe Met Glu Ile Leu Gly His
                405                 410                 415

Asp Asp Glu Asn Thr Gln Leu His Tyr Lys Gln Phe Lys Leu Ala Asn
            420                 425                 430

Phe Ser Arg Thr Trp Arg Pro Glu Val Gly Asp Glu Asn Thr Arg Leu
        435                 440                 445

Val Ala Leu Gln Lys Leu Asp Asp Glu Met Pro Gly Phe Ala Arg Gly
    450                 455                 460
```

```
Asp Ala Gly Val Arg Leu His Glu Thr Val Lys Gln Leu Val Glu Gln
465                 470                 475                 480

Asp Pro Ser Ala Lys Ile Thr Asn Ser Thr Leu Arg Ala Phe Lys Phe
                485                 490                 495

Ser Pro Thr Met Ile Ser Arg Tyr Leu Glu Phe Ala Ala Asp Ala Leu
            500                 505                 510

Gly Gln Phe Val Gly Glu Asn Gly Gln Trp Gln Leu Lys Ile Glu Thr
        515                 520                 525

Pro Ala Ile Val Leu Pro Asp Glu Glu Ser Val Glu Thr Ile Asp Glu
    530                 535                 540

Pro Asp Asp Glu Ser Gln Asp Glu Leu Asp Glu Asp Glu Ile Glu
545                 550                 555                 560

Leu Asp Glu Gly Gly Gly Asp Glu Pro Thr Glu Glu Glu Gly Pro Glu
                565                 570                 575

Glu His Gln Pro Thr Ala Leu Lys Pro Val Phe Lys Pro Ala Lys Asn
                580                 585                 590

Asn Gly Asp Gly Thr Tyr Lys Ile Glu Phe Glu Tyr Asp Gly Lys His
            595                 600                 605

Tyr Ala Trp Ser Gly Pro Ala Asp Ser Pro Met Ala Ala Met Arg Ser
    610                 615                 620

Ala Trp Glu Thr Tyr Tyr Ser
625                 630
```

```
<210> SEQ ID NO 11
<211> LENGTH: 1329
<212> TYPE: DNA
<213> ORGANISM: Agrobacterium tumefaciens strain C58
<220> FEATURE:
<221> NAME/KEY: misc_feature
<223> OTHER INFORMATION: Protelomerase TelA

<400> SEQUENCE: 11
atgctcgccg caaaacgaaa aacaaaaaca ccggtcctcg tggaacgcat cgatcaattc     60
gtcggccaga tcaaagaggc gatgaaaagc gacgacgctt cgcgaaacag gaaaatccgc    120
gatctgtggg atgccgaggt ccgctatcat ttcgataatg ccgcacggga aaagacgctc    180
gaactttaca tcatgaaaat acgcaatgcg ctgaaggccg aattcggccc gaagagcacc    240
ccgctagcca tctgcaacat gaagaagctg cgcgagcgcc tgaacaccta tattgcccgg    300
ggcgattatc ccaagacagg cgtggcgacg tcgattgtcg aaaaaatcga gcgggcggag    360
ttcaacaccg ccgccgcaa acccacggtt ctccttcgca tagccgattt cattgccgcg    420
atgaacggca tggacgcgaa gcaggacatg caggctctgt gggacgcaga aatcgccatc    480
atgaacggcc gcgcccagac gacgatcatt tcctacatca ccaaatatcg caacgccatc    540
cgggaagcct tcggtgacga ccatccgatg ctgaagatcg ccaccggcga tgccgcgatg    600
tatgacgagg cccgccgggt gaagatggag aagatcgcca acaagcatgg cgcgctcatc    660
acattcgaga actaccggca ggttctgaaa atctgcgagg attgtctcaa gtccagcgat    720
cccctgatga tcggcatcgg cctcatcggc atgacgggac gccgacccta tgaagtcttc    780
acccaggcgg aattttcacc tgcacccctat ggcaagggag tttccaaatg gagcatcctg    840
ttcaacggtc aggccaagac gaaacagggc gagggcacga aattcgggat taccatgaa     900 attcctgtcc tgacgcgctc cgaaaccgtg ctggctgcct ataagcgcct gcgcgaaagc    960
ggacagggaa aattatggca tggcatgtcg atcgacgatt tttcctcgga aacccgcctg   1020
ctgctgcgcg acacggtttt taacctgttc gaggatgtct ggccaaagga agagcttccc   1080
```

```
aagccctatg gcctcagaca cctctatgcc gaagtggcct atcacaattt cgcgccaccc    1140
catgtcacca agaacagcta tttcgccgcc attcttggcc acaacaataa cgacctcgaa    1200
acgtcgctgt cctatatgac ctatacgctg ccggaagacc gcgacaatgc gctggcgcgc    1260
ctgaagcgga ccaatgagcg gacattgcag caaatggcga cgatcgcgcc cgtgtcccgc    1320
aagggatga                                                           1329
```

<210> SEQ ID NO 12
<211> LENGTH: 442
<212> TYPE: PRT
<213> ORGANISM: Agrobacterium tumefaciens strain C58
<220> FEATURE:
<221> NAME/KEY: MISC_FEATURE
<223> OTHER INFORMATION: Protelomerase TelA

<400> SEQUENCE: 12

```
Met Leu Ala Ala Lys Arg Lys Thr Lys Thr Pro Val Leu Val Glu Arg
1               5                   10                  15

Ile Asp Gln Phe Val Gly Gln Ile Lys Glu Ala Met Lys Ser Asp Asp
            20                  25                  30

Ala Ser Arg Asn Arg Lys Ile Arg Asp Leu Trp Asp Ala Glu Val Arg
        35                  40                  45

Tyr His Phe Asp Asn Gly Arg Thr Glu Lys Thr Leu Glu Leu Tyr Ile
    50                  55                  60

Met Lys Tyr Arg Asn Ala Leu Lys Ala Glu Phe Gly Pro Lys Ser Thr
65                  70                  75                  80

Pro Leu Ala Ile Cys Asn Met Lys Lys Leu Arg Glu Arg Leu Asn Thr
                85                  90                  95

Tyr Ile Ala Arg Gly Asp Tyr Pro Lys Thr Gly Val Ala Thr Ser Ile
            100                 105                 110

Val Glu Lys Ile Glu Arg Ala Glu Phe Asn Thr Ala Gly Arg Lys Pro
        115                 120                 125

Thr Val Leu Leu Arg Ile Ala Asp Phe Ile Ala Ala Met Asn Gly Met
    130                 135                 140

Asp Ala Lys Gln Asp Met Gln Ala Leu Trp Asp Ala Glu Ile Ala Ile
145                 150                 155                 160

Met Asn Gly Arg Ala Gln Thr Thr Ile Ile Ser Tyr Ile Thr Lys Tyr
                165                 170                 175

Arg Asn Ala Ile Arg Glu Ala Phe Gly Asp Asp His Pro Met Leu Lys
            180                 185                 190

Ile Ala Thr Gly Asp Ala Ala Met Tyr Asp Glu Ala Arg Arg Val Lys
        195                 200                 205

Met Glu Lys Ile Ala Asn Lys His Gly Ala Leu Ile Thr Phe Glu Asn
    210                 215                 220

Tyr Arg Gln Val Leu Lys Ile Cys Glu Asp Cys Leu Lys Ser Ser Asp
225                 230                 235                 240

Pro Leu Met Ile Gly Ile Gly Leu Ile Gly Met Thr Gly Arg Arg Pro
                245                 250                 255

Tyr Glu Val Phe Thr Gln Ala Glu Phe Ser Pro Ala Pro Tyr Gly Lys
            260                 265                 270

Gly Val Ser Lys Trp Ser Ile Leu Phe Asn Gly Gln Ala Lys Thr Lys
        275                 280                 285

Gln Gly Glu Gly Thr Lys Phe Gly Ile Thr Tyr Glu Ile Pro Val Leu
    290                 295                 300
```

Thr Arg Ser Glu Thr Val Leu Ala Ala Tyr Lys Arg Leu Arg Glu Ser
305                 310                 315                 320

Gly Gln Gly Lys Leu Trp His Gly Met Ser Ile Asp Asp Phe Ser Ser
            325                 330                 335

Glu Thr Arg Leu Leu Leu Arg Asp Thr Val Phe Asn Leu Phe Glu Asp
            340                 345                 350

Val Trp Pro Lys Glu Leu Pro Lys Pro Tyr Gly Leu Arg His Leu
        355                 360                 365

Tyr Ala Glu Val Ala Tyr His Asn Phe Ala Pro His Val Thr Lys
    370                 375                 380

Asn Ser Tyr Phe Ala Ala Ile Leu Gly His Asn Asn Asp Leu Glu
385                 390                 395                 400

Thr Ser Leu Ser Tyr Met Thr Tyr Leu Pro Glu Asp Arg Asp Asn
            405                 410                 415

Ala Leu Ala Arg Leu Lys Arg Thr Asn Glu Arg Thr Leu Gln Gln Met
            420                 425                 430

Ala Thr Ile Ala Pro Val Ser Arg Lys Gly
            435                 440

<210> SEQ ID NO 13
<211> LENGTH: 1668
<212> TYPE: DNA
<213> ORGANISM: Vibrio parahaemolyticus phage Vp58.5 Gp40
<220> FEATURE:
<221> NAME/KEY: misc_feature
<223> OTHER INFORMATION: Protelomerase

<400> SEQUENCE: 13

```
atgaaactaa ctgacggaat ggaccgcaca aagtacatcg ttaaagcggc caaacatatc      60
caagaagaag gtcaagaaaa gggacctaaa tacatcactg accgctgcgg tcgtgtcgct     120
aaggatgagc acaaacgtct tggctgggtt gtggaccagg tgtcaggtga gctggccagc     180
aatccacaaa tcagccataa ccactatatc aatcttatga ataattaccg tagagccatc     240
aaggccctag gtataagca tcaccaaata gaaaagacat tagtaacttt tatcaataaa     300
tatcaagaat atagacctga atagcagag atgctggacc catctttgcc aattgatacc     360
ttgagagaga atgtgatcct tctgaaatca caggccaggt caaaaagtga atttcgtagt     420
gacctgcttg tcttcgcat tgagtttcac ctctactatc tgtttgaacc aaagggcatt     480
gcaaccgata gcgcaaaga gcaagtaaaa gaagcgttga tgaaaagca tgagaacgtc     540
atcaagataa atggcgatca catcaaggaa ctggccacaa aaattctgtc agaaaaggac     600
ccgtcatata cagaccttgc agttggcctt gctcttgcga ctggccgtcg agctaatgag     660
attatgaaga ctgccagctt taagaaatca ggtgaacggt cgcttatgtt tgagggacag     720
ctaaaaaccc ataaccgata cctgtttgaa gaaattggag catacgagat accttgtatt     780
gttgattcag acttagtaat taaggattg aaattattaa gaaaaaaaac aggagcggaa     840
atcctggaat atactgatgt cactggacgt acagttaaaa aggctgttgc tgacggcgac     900
actaaggacc tgagacacaa tgatgcagtc aaccttcggt tcactgcatc acttaaccag     960
agagtcaagg ccatactagg ccatggagag tttagtttca ggacctgtcg ggccatctat    1020
gtcgaaatag cattccatga gttcagacat aacggagaat cgaaagcggc cttccgtagc    1080
agagttcttg gccactcagg tggtgataaa tcaacacaga accactatga ggggtttgag    1140
cttgattcca aggtggaaac catcggtgtg gttgatatgg ccaaaacga ggctgacaag    1200
tcatacaaca agcaactgct gaagcacctg gagcaatacg atgcaacaat tgcagcctat    1260
```

-continued

```
ctgagagcgc ctaactggaa acacattcat gattggctaa aagaccaggt gaaaaacggc    1320
ctgcagcttg accaaataac cacaagctat ctgagaaaaa tgtgcatcat caacaacaaa    1380
agcctcaatg caaacaccat cgccaagtac ctggaaacat tgaacctaga taaggttcca    1440
gcagagcaag aggaaagcca tcaggaagaa ctggagcagg aagaagatca gaaagtgtca    1500
tggccaaaag ctaaagacat taaggtccag tctaaaaaag aaggtgatat gtggcatgtc    1560
tggactgagg ttaacggaat gcggtgggaa aattggtcta aggtagaaa acagaagct     1620 gtgaaggcat tgcgacaaca atatgagagg gaatcagcgg aaatgtaa                 1668
```

<210> SEQ ID NO 14
<211> LENGTH: 555
<212> TYPE: PRT
<213> ORGANISM: Vibrio parahaemolyticus phage Vp58.5 Gp40
<220> FEATURE:
<221> NAME/KEY: MISC_FEATURE
<223> OTHER INFORMATION: Protelomerase

<400> SEQUENCE: 14

```
Met Lys Leu Thr Asp Gly Met Asp Arg Thr Lys Tyr Ile Val Lys Ala
1               5                   10                  15

Ala Lys His Ile Gln Glu Glu Gly Gln Glu Lys Gly Pro Lys Tyr Ile
            20                  25                  30

Thr Asp Arg Cys Gly Arg Val Ala Lys Asp Glu His Lys Arg Leu Gly
        35                  40                  45

Trp Val Val Asp Gln Val Ser Gly Glu Leu Ala Ser Asn Pro Gln Ile
    50                  55                  60

Ser His Asn His Tyr Ile Asn Leu Met Asn Asn Tyr Arg Arg Ala Ile
65                  70                  75                  80

Lys Ala Leu Gly Tyr Lys His His Gln Ile Glu Lys Thr Leu Val Thr
                85                  90                  95

Phe Ile Asn Lys Tyr Gln Glu Tyr Arg Pro Glu Ile Ala Glu Met Leu
            100                 105                 110

Asp Pro Ser Leu Pro Ile Asp Thr Leu Arg Glu Asn Val Ile Leu Leu
        115                 120                 125

Lys Ser Gln Ala Arg Ser Lys Ser Glu Phe Arg Ser Asp Leu Leu Gly
    130                 135                 140

Leu Arg Ile Glu Phe His Leu Tyr Tyr Leu Phe Glu Pro Lys Gly Ile
145                 150                 155                 160

Ala Thr Asp Lys Arg Lys Glu Gln Val Lys Glu Ala Leu Asn Glu Lys
                165                 170                 175

His Glu Asn Val Ile Lys Ile Asn Gly Asp His Ile Lys Glu Leu Ala
            180                 185                 190

Thr Lys Ile Leu Ser Glu Lys Asp Pro Ser Tyr Thr Asp Leu Ala Val
        195                 200                 205

Gly Leu Ala Leu Ala Thr Gly Arg Arg Ala Asn Glu Ile Met Lys Thr
    210                 215                 220

Ala Ser Phe Lys Lys Ser Gly Glu Arg Ser Leu Met Phe Glu Gly Gln
225                 230                 235                 240

Leu Lys Thr His Asn Arg Tyr Leu Phe Glu Glu Ile Gly Ala Tyr Glu
                245                 250                 255

Ile Pro Cys Ile Val Asp Ser Asp Leu Val Ile Lys Gly Leu Lys Leu
            260                 265                 270

Leu Arg Lys Lys Thr Gly Ala Glu Ile Leu Glu Tyr Thr Asp Val Thr
        275                 280                 285
```

```
Gly Arg Thr Val Lys Lys Ala Val Ala Asp Gly Asp Thr Lys Asp Leu
    290                 295                 300

Arg His Asn Asp Ala Val Asn Leu Arg Phe Thr Ala Ser Leu Asn Gln
305                 310                 315                 320

Arg Val Lys Ala Ile Leu Gly His Gly Glu Phe Ser Phe Arg Thr Cys
                325                 330                 335

Arg Ala Ile Tyr Val Glu Ile Ala Phe His Glu Phe Arg His Asn Gly
            340                 345                 350

Glu Ser Lys Ala Ala Phe Arg Ser Arg Val Leu Gly His Ser Gly Gly
        355                 360                 365

Asp Lys Ser Thr Gln Asn His Tyr Glu Gly Phe Glu Leu Asp Ser Lys
    370                 375                 380

Val Glu Thr Ile Gly Val Val Asp Met Gly Gln Asn Glu Ala Asp Lys
385                 390                 395                 400

Ser Tyr Asn Lys Gln Leu Leu Lys His Leu Glu Gln Tyr Asp Ala Thr
                405                 410                 415

Ile Ala Ala Tyr Leu Arg Ala Pro Asn Trp Lys His Ile His Asp Trp
            420                 425                 430

Leu Lys Asp Gln Val Lys Asn Gly Leu Gln Leu Asp Gln Ile Thr Thr
        435                 440                 445

Ser Tyr Leu Arg Lys Met Cys Ile Ile Asn Asn Lys Ser Leu Asn Ala
    450                 455                 460

Asn Thr Ile Ala Lys Tyr Leu Glu Thr Leu Asn Leu Asp Lys Val Pro
465                 470                 475                 480

Ala Glu Gln Glu Glu Ser His Gln Glu Gly Leu Glu Gln Glu Glu Asp
                485                 490                 495

Gln Lys Val Ser Trp Pro Lys Ala Lys Asp Ile Lys Val Gln Ser Lys
            500                 505                 510

Lys Glu Gly Asp Met Trp His Val Trp Thr Glu Val Asn Gly Met Arg
        515                 520                 525

Trp Glu Asn Trp Ser Lys Gly Arg Lys Thr Glu Ala Val Lys Ala Leu
    530                 535                 540

Arg Gln Gln Tyr Glu Arg Glu Ser Ala Glu Met
545                 550                 555

<210> SEQ ID NO 15
<211> LENGTH: 56
<212> TYPE: DNA
<213> ORGANISM: Escherichia coli phage N15
<220> FEATURE:
<221> NAME/KEY: misc_feature
<223> OTHER INFORMATION: protelomerase target sequence

<400> SEQUENCE: 15
tatcagcaca caattgccca ttatacgcgc gtataatgga ctattgtgtg ctgata          56

<210> SEQ ID NO 16
<211> LENGTH: 50
<212> TYPE: DNA
<213> ORGANISM: Klebsiella phage phiK02
<220> FEATURE:
<221> NAME/KEY: misc_feature
<223> OTHER INFORMATION: protelomerase target sequence

<400> SEQUENCE: 16
cagcacacaa cagcccatta tacgcgcgta taatgggcta ttatgtgctg              50
```

```
<210> SEQ ID NO 17
<211> LENGTH: 52
<212> TYPE: DNA
<213> ORGANISM: Yersinia enterolytica phage PY54
<220> FEATURE:
<221> NAME/KEY: misc_feature
<223> OTHER INFORMATION: protelomerase target sequence

<400> SEQUENCE: 17
tagtcaccta tttcagcata ctacgcgcgt agtatgctga aataggttac tg          52

<210> SEQ ID NO 18
<211> LENGTH: 90
<212> TYPE: DNA
<213> ORGANISM: Vibrio sp. phage VP882
<220> FEATURE:
<221> NAME/KEY: misc_feature
<223> OTHER INFORMATION: protelomerase target sequence

<400> SEQUENCE: 18
gggatcccgt tccatacata catgtatcca tgtggcatac tatacgtata gtatgccgat     60
gttacatatg gtatcattcg ggatcccgtt                                    90

<210> SEQ ID NO 19
<211> LENGTH: 38
<212> TYPE: DNA
<213> ORGANISM: Borrelia burgdorferi
<220> FEATURE:
<221> NAME/KEY: misc_feature
<223> OTHER INFORMATION: protelomerase target sequence

<400> SEQUENCE: 19
tactaaataa atattatata taaattttt tattagta                             38

<210> SEQ ID NO 20
<211> LENGTH: 50
<212> TYPE: DNA
<213> ORGANISM: Agrobacterium tumefaciens strain C58
<220> FEATURE:
<221> NAME/KEY: misc_feature
<223> OTHER INFORMATION: protelomerase target sequence

<400> SEQUENCE: 20
gcgatcgatc ataataacaa tatcatgata ttgttattgt aatcgatcgc               50

<210> SEQ ID NO 21
<211> LENGTH: 56
<212> TYPE: DNA
<213> ORGANISM: Vibrio parahaemolyticus phage Vp58.5 Gp40
<220> FEATURE:
<221> NAME/KEY: misc_feature
<223> OTHER INFORMATION: protelomerase target sequence

<400> SEQUENCE: 21
aacctgcaca ggtgtacata tagtctaatt agactatatg tacacctgtg caggtt        56

<210> SEQ ID NO 22
<211> LENGTH: 26
<212> TYPE: DNA
<213> ORGANISM: Agrobacterium tumefaciens strain C58
<220> FEATURE:
<221> NAME/KEY: misc_feature
<223> OTHER INFORMATION: protelomerase target sequence

<400> SEQUENCE: 22
aataacaata tcatgatatt gttatt                                        26
```

```
<210> SEQ ID NO 23
<211> LENGTH: 65
<212> TYPE: DNA
<213> ORGANISM: Artificial
<220> FEATURE:
<223> OTHER INFORMATION: stem loop motif

<400> SEQUENCE: 23
gggcggtcgg ctgcgcgcgt gggccaagtc tccctacaag ggcccacgcg cgcagccgac    60
cgccc                                                                65

<210> SEQ ID NO 24
<211> LENGTH: 75
<212> TYPE: DNA
<213> ORGANISM: Artificial
<220> FEATURE:
<223> OTHER INFORMATION: stem loop motif

<400> SEQUENCE: 24
gggcggtcgg ctgcgcgcgt gggccaaaaa aagtctccct acaagaaaaa ggcccacgcg    60
cgcagccgac cgccc                                                     75

<210> SEQ ID NO 25
<211> LENGTH: 75
<212> TYPE: DNA
<213> ORGANISM: Artificial
<220> FEATURE:
<223> OTHER INFORMATION: stem loop motif

<400> SEQUENCE: 25
gggcggtcgg ctgcgcgcgt gggccaaaaa aaaaaagtc tccctacaag ggcccacgcg    60
cgcagccgac cgccc                                                     75

<210> SEQ ID NO 26
<211> LENGTH: 75
<212> TYPE: DNA
<213> ORGANISM: Artificial
<220> FEATURE:
<223> OTHER INFORMATION: stem loop motif

<400> SEQUENCE: 26
gggcggtcgg ctgcgcgcgt gggccaagtc tccctacaag aaaaaaaaaa ggcccacgcg    60
cgcagccgac cgccc                                                     75

<210> SEQ ID NO 27
<211> LENGTH: 45
<212> TYPE: DNA
<213> ORGANISM: Artificial
<220> FEATURE:
<223> OTHER INFORMATION: stem loop motif

<400> SEQUENCE: 27
gggcggtcgg gtgcgaagtc tccctacaag cgcacccgac cgccc                    45

<210> SEQ ID NO 28
<211> LENGTH: 55
<212> TYPE: DNA
<213> ORGANISM: Artificial
<220> FEATURE:
<223> OTHER INFORMATION: stem loop motif

<400> SEQUENCE: 28
gggcggtcgg gtgcgaaaaa aagtctccct acaagaaaaa cgcacccgac cgccc         55
```

<210> SEQ ID NO 29
<211> LENGTH: 55
<212> TYPE: DNA
<213> ORGANISM: Artificial
<220> FEATURE:
<223> OTHER INFORMATION: stem loop motif

<400> SEQUENCE: 29
gggcggtcgg gtgcgaaaaa aaaaaaagtc tccctacaag cgcacccgac cgccc    55

<210> SEQ ID NO 30
<211> LENGTH: 55
<212> TYPE: DNA
<213> ORGANISM: Artificial
<220> FEATURE:
<223> OTHER INFORMATION: stem loop motif

<400> SEQUENCE: 30
gggcggtcgg gtgcgaagtc tccctacaag aaaaaaaaaa cgcacccgac cgccc    55

<210> SEQ ID NO 31
<211> LENGTH: 41
<212> TYPE: DNA
<213> ORGANISM: Artificial
<220> FEATURE:
<223> OTHER INFORMATION: stem loop motif figure 10a

<400> SEQUENCE: 31
aaatataaac ctaaagtctc cctacaagta agtttatatt t    41

<210> SEQ ID NO 32
<211> LENGTH: 7
<212> TYPE: DNA
<213> ORGANISM: Artificial
<220> FEATURE:
<223> OTHER INFORMATION: primer

<400> SEQUENCE: 32 tagggag    7

<210> SEQ ID NO 33
<211> LENGTH: 9
<212> TYPE: DNA
<213> ORGANISM: Artificial
<220> FEATURE:
<223> OTHER INFORMATION: primer

<400> SEQUENCE: 33 gtagggaga    9

<210> SEQ ID NO 34
<211> LENGTH: 11
<212> TYPE: DNA
<213> ORGANISM: Artificial
<220> FEATURE:
<223> OTHER INFORMATION: primer

<400> SEQUENCE: 34
tgtagggaga c    11

<210> SEQ ID NO 35
<211> LENGTH: 13
<212> TYPE: DNA
<213> ORGANISM: Artificial
<220> FEATURE:

```
<223> OTHER INFORMATION: primer

<400> SEQUENCE: 35
ttgtagggag act                                                          13

<210> SEQ ID NO 36
<211> LENGTH: 15
<212> TYPE: DNA
<213> ORGANISM: Artificial
<220> FEATURE:
<223> OTHER INFORMATION: primer

<400> SEQUENCE: 36
cttgtaggga gactt                                                        15

<210> SEQ ID NO 37
<211> LENGTH: 11
<212> TYPE: DNA
<213> ORGANISM: Artificial
<220> FEATURE:
<223> OTHER INFORMATION: primer

<400> SEQUENCE: 37
gcgtataatg g                                                            11
```